(12) United States Patent
Zhang et al.

(10) Patent No.: US 8,999,641 B2
(45) Date of Patent: *Apr. 7, 2015

(54) ENGINEERING AND OPTIMIZATION OF SYSTEMS, METHODS AND COMPOSITIONS FOR SEQUENCE MANIPULATION WITH FUNCTIONAL DOMAINS

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Feng Zhang, Cambridge, MA (US); Le Cong, Cambridge, MA (US); Randall Jeffrey Platt, Cambridge, MA (US); Neville Espi Sanjana, Cambridge, MA (US)

(73) Assignees: The Broad Institute Inc., Cambridge, MA (US); Maassachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/226,274

(22) Filed: Mar. 26, 2014

(65) Prior Publication Data

US 2014/0256046 A1    Sep. 11, 2014

Related U.S. Application Data

(63) Continuation of application No. PCT/US2013/074736, filed on Dec. 12, 2013.

(60) Provisional application No. 61/748,427, filed on Jan. 2, 2013, provisional application No. 61/758,468, filed on Jan. 30, 2013, provisional application No. 61/769,046, filed on Feb. 25, 2013, provisional application No. 61/791,409, filed on Mar. 15, 2013, provisional application No. 61/802,174, filed on Mar. 15, 2013, provisional application No. 61/806,375, filed on Mar. 28, 2013, provisional application No. 61/814,263, filed on Apr. 20, 2013, provisional application No. 61/819,803, filed on May 6, 2013, provisional application No. 61/828,130, filed on May 28, 2013, provisional application No. 61/835,931, filed on Jun. 17, 2013, provisional application No. 61/835,936, filed on Jun. 17, 2013, provisional application No. 61/736,527, filed on Dec. 12, 2012.

(51) Int. Cl.
| | |
|---|---|
| C12Q 1/68 | (2006.01) |
| C12N 15/85 | (2006.01) |
| C12N 15/63 | (2006.01) |
| C12N 15/01 | (2006.01) |
| C12N 15/86 | (2006.01) |
| C12N 9/14 | (2006.01) |
| C12N 9/22 | (2006.01) |
| C12N 9/52 | (2006.01) |
| C12N 15/00 | (2006.01) |
| C07H 21/02 | (2006.01) |
| C07H 21/04 | (2006.01) |
| A61K 38/43 | (2006.01) |
| A61K 38/46 | (2006.01) |
| A61K 38/47 | (2006.01) |
| C12N 15/10 | (2006.01) |

(52) U.S. Cl.
CPC . *C12N 15/85* (2013.01); *C12N 9/22* (2013.01); *C12N 15/1082* (2013.01); *C12N 15/63* (2013.01); *C12N 15/01* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 2010/0076057 A1† | 3/2010 | Sontheimer | |
| 2011/0189776 A1 | 8/2011 | Terns et al. | |
| 2011/0223638 A1 | 9/2011 | Wiedenheft et al. | |
| 2013/0130248 A1 | 5/2013 | Haurwitz et al. | |
| 2014/0068797 A1 | 3/2014 | Doudna et al. | |

FOREIGN PATENT DOCUMENTS

| | | |
|---|---|---|
| WO | WO/2008/108989 | 9/2008 |
| WO | WO/2010/054108 | 5/2010 |
| WO | 2011146121 A1 † | 11/2011 |
| WO | WO/2012/164565 | 12/2012 |
| WO | WO/2013/098244 | 7/2013 |

(Continued)

OTHER PUBLICATIONS

U.S. Appl. No. 61/613,373, filed Mar. 20, 2012 51 pages.*

(Continued)

*Primary Examiner* — Anne Gussow
*Assistant Examiner* — Nancy J Leith
(74) *Attorney, Agent, or Firm* — Vedder Price P.C.; Thomas J. Kowalski; Deborah L. Lu

(57) ABSTRACT

The invention provides for engineering and optimization of systems, methods, and compositions for manipulation of sequences and/or activities of target sequences. Provided are vectors and vector systems, some of which encode one or more components of a CRISPR complex, as well as methods for the design and use of such vectors with additional functional domains. Also provided are methods of directing CRISPR complex formation in prokaryotic and eukaryotic cells to ensure enhanced specificity for target recognition and avoidance of toxicity.

28 Claims, 49 Drawing Sheets

(56) References Cited

FOREIGN PATENT DOCUMENTS

| WO | 2013/141680 A1 * | 9/2013 | ............ C12N 15/10 |
| WO | 2013/142578 A1 * | 9/2013 | ............ C12N 15/10 |
| WO | WO 2013/141680 | 9/2013 | |
| WO | WO 2013/142578 | 9/2013 | |
| WO | WO/2013176772 | 11/2013 | |
| WO | 2014065596 A1 † | 5/2014 | |
| WO | WO 2014/065596 | 5/2014 | |
| WO | WO 2014/089290 | 6/2014 | |
| WO | WO 2014/093479 | 6/2014 | |
| WO | WO 2014/099744 | 6/2014 | |
| WO | WO 2014/099750 | 6/2014 | |

OTHER PUBLICATIONS

U.S. Appl. No. 61/625,420, filed Apr. 17, 2012 51 pages.*
Kirill A. Datsenko, et al., Molecular Memory of Prior Infections Activates the CRISPR/Cas Adaptive Bacterial Immunity System, Nature Communications, Jul. 10, 2012, D0I:10.1038/ncomms1937.
Ksenia Pougach, et al., Transcription, Processing and Function of CRISPR Cassettes in *Escherichia coli*, Mol. Microbiol, Sep. 2010, 77(6), p. 1367-1379.
Al-Attar et al., Clustered Regularly Interspaced Short Palindromic Repeats (CRISPRs): The Hallmark of an Ingenious Antiviral Defense Mechanism in Prokaryotes, *Biol Chem*. (2011) vol. 392, Issue 4, pp. 277-289.
Carroll, A CRISPR Approach to Gene Targeting, Molecular Therapy (2012) vol. 20, No. 9, p. 1658-1660.
Gasiunas, et al., Cas9-crRNA Ribonucleoprotein Complex Mediates Specific DNA cleavage for Adaptive Immunity in Bacteria, PNAS USA (2012) vol. 109, No. 39, p. E2579-E2586.
Hale et al., Essential Features and Rational Design of CRISPR RNAs That Function With the Cas RAMP Module Complex to Cleave RNAs, *Molecular Cell*, (2012) vol. 45, Issue 3, 292-302.
Jinek et al, A Programmable Dual-RNA-Guided DNA Endonuclease in Adaptive Bacterial Immunity, Science (2012) vol. 337, p. 816-821.
Makarova et al., Evolution and Classification of the CRISPR-CAS Systems, Nature Reviews Microbiology (2011) vol. 9, No. 6, p. 467-477.
Erik Sontheimer, Project 7: Establishing RNA-Directed DNA Targeting in Eukaryotic Cells; Project dates: Nov. 16, 2011 to Dec. 31, 2012 (Feb. 4, 2012).
Wiedenheft, et al., RNA-Guided Genetic Silencing Systems in Bacteria and Archaea, Nature (2012) vol. 482, p. 331-338.
U.S. Appl. No. 61/738,355, filed Dec. 17, 2012, George M. Church.
U.S. Appl. No. 61/779,169, filed Mar. 13, 2013, Prashant Mali.
Le Cong, et al., Supplementary Material: Multiplex Genome Engineering Using CRISPR-Cas Systems, Science Express (Jan. 3, 2013).
U.S. Appl. No. 61/735,876, filed Dec. 11, 2012, Blake A. Wiedenheft.
U.S. Appl. No. 61/799,531, filed Mar. 15, 2013, Blake A. Wiedenheft.
Le Cong, et al., Multiplex Genome Engineering Using CRISPR-Cas Systems, Science (Feb. 2013) vol. 339, p. 819-823.
Le Cong, et al., Supplementary Material: Multiplex Genome Engineering Using CRISPR-Cas Systems, Science Express (Jul. 5, 2012).
Seung Woo Cho, et al., Targeted Genome Engineering in Human Cells With the Cas9 RNA-Guided Endonuclease, Nature Biotechnology (Mar. 2013) vol. 31, No. 3, p. 230-232.
Seung Woo Cho, et al., Supplementary Information: Targeted Genome Engineering in Human Cells With the Cas9 RNA-Guided Endonuclease, Nature Biotechnology (Mar. 2013) vol. 31, No. 3, p. 1-10.
U.S. Appl. No. 61/734,256, filed Dec. 6, 2012, Fuqiang Chen.
U.S. Appl. No. 61/758,624, filed Jan. 30, 2013, Fuqiang Chen.
U.S. Appl. No. 61/761,046, filed Feb. 5, 2013, Scott Knight.
U.S. Appl. No. 61/794,422, filed Mar. 15, 2013, Scott Knight.
Third Party Observation filed Oct. 22, 2014 in EP No. 20130824232.
Response to Third Party Observations in EP Application No. 20130824232 filed with Request for Oral Hearing, Oct. 27, 2014.
Request for Oral Hearing in EP Application No. 13818570.7, Oct. 27, 2014.

Elitza Deltcheva, et al., CRISPR RNA Maturation by Trans-Encoded Small RNA and Host Factor RNase III, Nature (2011) vol. 471, p. 602-607.
Deltcheva, et al., Supplementary Figures: CRISPR RNA Maturation by Trans-Encoded Small RNA and Host Factor RNase III. Downloaded from www.nature.com/nature, p. 1-35, 2011.
Third Party Observation for Application No. EP20130824232 filed Sep. 22, 2014.
Shen, et al., Generation of Gene-Modified Mice Via Cas9/RNA-Mediated Gene Targeting, Cell Research (2013) vol. 23, p. 720-723.
Nakamura, et al., Codon Usage Tabulated From International DNA Sequence Databases: Status for the Year 2000, Nucleic Acids Research (2000) vol. 28, No. 1, p. 292.
U.S. Appl. No. 61/652,086, filed May 2012.
U.S. Appl. No. 61/716,256, filed Oct. 2012.
U.S. Appl. No. 61/613,373, filed Mar. 2012.
U.S. Appl. No. 61/625,420, filed Apr. 2013.
Third Party Observation filed Oct. 1, 2014 in EP No. 20130818570.
Response to Third Party Observations in EP No. 20130818570 filed Oct. 16, 2014, with Redlined and Clean Amended Claims.
Alexandra E. Briner, et al., Guide RNA Functional Modules Direct Cas9 Activity and Orthogonality, Molecular Cell (Oct. 23, 2014) vol. 56, p. 333-339.
Electronic Mail dated Nov. 3, 2014 from Thomas Kowalski.
Response to Third Party Observations in EP No. 13824232.6 filed Oct. 2, 2014, with Redlined and Clean Amended Claims.
Susanne Andreas, et al., Enhanced Efficiency Through Nuclear Localization Signal Fusion on Phage $\phi$C31-Integrase: Activity Comparison With Cre and FLPe Recombinase in Mammalian Cells, Nucleic Acids Research (2002) vol. 30, No. 11, p. 2299-2306.
Jens Boch, et al., *Xanthomonas* AvrBs3 Family-Type III Effectors: Discovery and Function, Annu. Rev. Phytopathol. (2010) vol. 48, p. 419-436.
Tomas Cermak, et al., Efficient Design and Assembly of Custom TALEN and Other TAL Effector-Based Constructs for DNA Targeting, Nucleic Acids Research (2011) vol. 39, No. 12, e82, p. 1-11.
Michelle Christian, et al., Targeting DNA Double-Strand Breaks With TAL Effector Nucleases; Genetics (2010) vol. 186, p. 757-761.
Michelle Christian, et al., Targeting DNA Double-Strand Breaks With TAL Effector Nucleases; Genetics (2010), Supporting Information, 1SI-8SI.
C. Dingwall, et al., Abstract: A Polypeptide Domain That Specifies Migration of Nucleoplasmin Into the Nucleus, Cell (1982) vol. 2, p. 449-58.
Garneau, et al., The CRISPR-Cas Bacterial Immune Systems Cleaves Bacteriophage and Plasmid DNA, Nature (2010) 468:67-71.
David S. Goldfarb, et al., Synthetic Peptides As Nuclear Localization Signals, Nature (1986) vol. 322, p. 641-644.
Claes Gustafsson, et al., Codon Bias and Heterologous Protein Expression, Trends in Biotechnology (2004) vol. 22, No. 7, p. 346-353.
Woong Y. Hwang, et al., Efficient Genome Editing in Zebrafish Using a CRISPR-Cas System, Nature Biotechnology (2013) vol. 31, No. 3, p. 227-229.
Mali, et al., RNA-Guided Human Genome engineering Via Cas9, Science 339:823-826. Published Online Jan. 2, 2013.
Stacey S. Patterson, et al., Codon Optimization of Bacterial Luciferase (lux) for Expression in Mammalian Cells, J. Ind. Microbio. Biotechnology (2005) vol. 32, p. 115-123.
Matthew H. Porteus, et al., Gene Targeting Using Zinc Finger Nucleases, Nature Biotechnology (2005) vol. 23, No. 8, p. 967-973.
Tim A. Rand, et al., Argonaute2 Cleaves the Anti-Guide Strand of siRNA During RISC Activation, Cell (2005) vol. 123, p. 621-629.
Edward J. Rebar, et al., Induction of Angiogenesis in a Mouse Model Using Engineered Transcription Factors, Nature Medicine (Dec. 2002) vol. 8, No. 12, p. 1427-1432.
Laura Schramm, et al., Recruitment of RNA Polymerase III to Its Target Promoters, Genes & Development (2002) vol. 16, p. 2593-2620.
Sapranauskas, et al., The *Streptococcus thermophilus* CRISPR-Cas System Provides Immunity in *Escherichia coli*, Nucleic Acids Research 39:9275-9282. Published Online Aug. 3, 2011.

(56) References Cited

OTHER PUBLICATIONS

Niraj H. Tolia, et al., Slicer and the Argonautes, Nature Chemical Biology (2007) vol. 3, No. 1, p. 36-43.
Fyodor D. Urnov, et al., Highly Efficient Endogenous Human Gene Correction Using Designed Zinc-Finger Nucleases, Nature (2005) vol. 435, p. 646-651.
Wu, et al., Genome-Wide Binding of the CRISPR Endonuclease Cas9 in Mammalian Cells, Nature Biotechnology p. 1-9. Published Online Apr. 20, 2014).
Third-Party Observation for Application No. EP20130824232 Aug. 9, 2014.
Miller, et al., A TALE Nuclease Architecture for Efficient Genome Editing Nature Biotechnology (2011) vol. 29, No. 2, p. 143-150.
EP Examination Report dated Dec. 16, 2014 for EP Application No. 13824232.6.
Response to EP Examination Report dated Dec. 31, 2014.
Jeremy Barrangou, RNA-Mediated Programmable DNA Cleavage, Nature Biotechnology (2012) vol. 30, No. 9, p. 836-838.
John van de Oost, New Tool for Genome Surgery, Science (Feb. 15, 2013) vol. 336, p. 768-768.
Horvath, et al., RNA-Guided Genome Editing àla carte, Cell Research, Cell Research (2013) vol. 23: 733-734.
Alan M. Lambowitz, et al.,Group II Introns: Mobile Ribozymes that Invade DNA. Downloaded from http://schperspectives.cshlp.org/, on Dec. 29, 2014.
University of Berkeley Press Release—Cheap and easy technique to snip DNA could revolutionize gene therapy, Jan. 7, 2013, p. 1-3.
Raymond, et al., High-Efficiency FLP and φC31 Site-Specific Recombination in Mammalian Cells, PLoS One (Jan. 2007) Issue 1, e162, p. 1-4.
Communication Forwarding Declaration of Feng Zhang dated Nov. 24, 2014.
Third Party Observation filed Jan. 6, 2015 in EP 13793997.1.
Martin Jinek, et al., RNA-programmed genome editing in human cells; eLife 2013:e00471, p. 1-9.
U.S. Appl. No. 61/734,256, filed Dec. 6, 2012, Chen, F. et al.†
Bassett, A.R. and Liu, J.-L., "CRISPR/Cas9 and Genome Editing in *Drosophila*," Journal of Genetics and Genomics, 2014, vol. 41, pp. 7-19 (including supplementary materials).†
Qi, L. et al., "RNA Processing Enables Predictable Programming of Gene Expression," Nature Biotechnology, 2012, vol. 30(10), pp. 1002-1007 (including Supplementary Information).†
Li, T. et al., "Modularly Assembled Designer TAL Effector Nucleases for Targeted Gene Knockout and Gene Replacement in Eukaryotes," Nucleic Acids Research, 2011, vol. 39(14), pp. 6315-6325.†
Raymond, C.S. and Soriano, P., "High-Efficiency FLP and PhiC31 Site-Specific Recombination in Mammalian Cells," PLoS One, 2007, vol. 2(1), p. e162.†
Mali, P. et al., "Cas9 as a Versatile Tool for Engineering Biology," Nature Methods, 2013, vol. 10 (10), pp. 957-963.†
Shanks, P., "CRISPR Opportunities . . . For What? And for Whom?," Biopolitical Times, Dec. 4, 2014, http://www.biopoliticaltimes.org/article.php?id=8235.†
Regalado, A., "Who Owns the Biggest Biotech Discovery of the Century?," MIT Technology Review, Dec. 4, 2014, http://www.technologyreview.com/featuredstory/532796/who-owns-the-biggest-biotech-discovery-of-the-century/.†
EP13824232.6 Communication from the Examining Division mailed on Dec. 16, 2014.†
U.S. Appl. No. 61/652,086, filed May 25, 2012, Jinek, M. et al.†

\* cited by examiner
† cited by third party

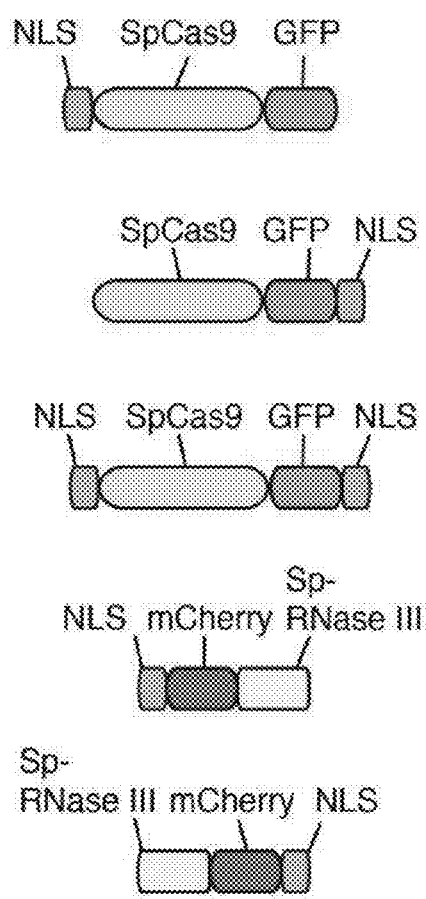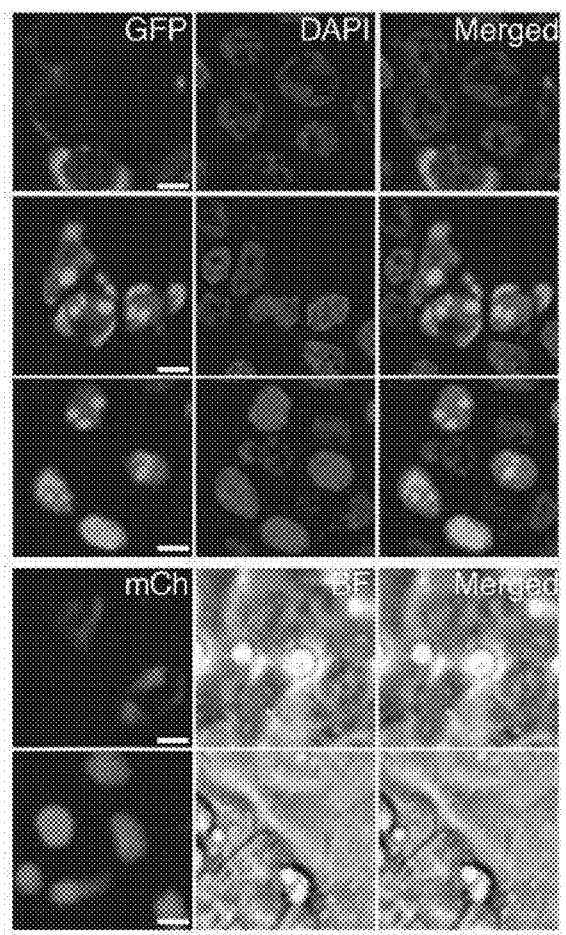
FIG. 2B

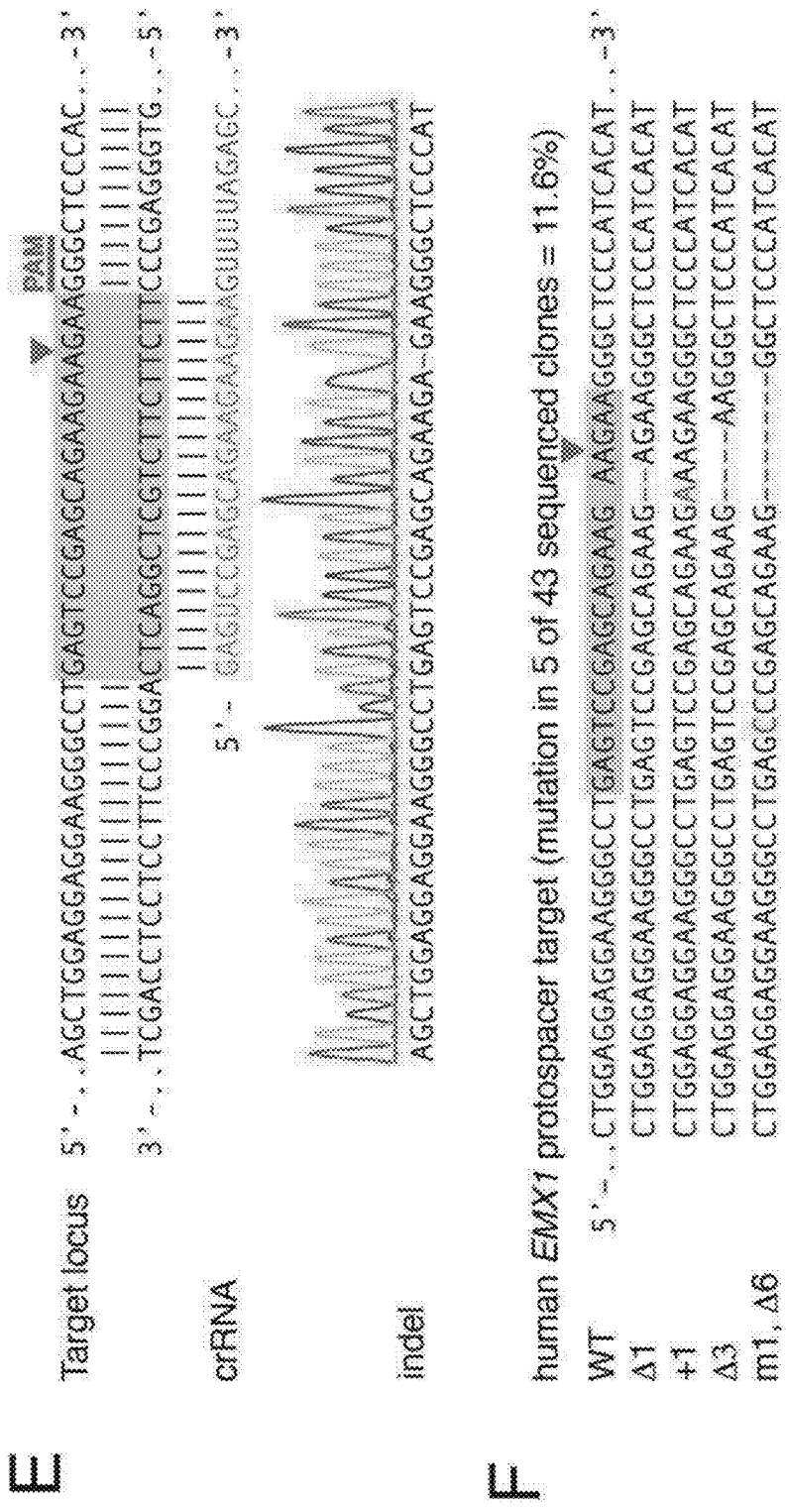
FIG. 2E-F

FIG. 4A

From top to bottom:
pXRP02- pLenti2-EF1a-NLS-hSpCsn1(10A,840A)-NLS-VP64-EGFP
pXRP04- pLenti2-EF1a-NLS-hSpCsn1(10A,840A)-NLS-VP64-2A-EGFP-NLS
pXRP06- pLenti2-EF1a-NLS-EGFP-VP64-NLS-hSpCsn1(10A,840A)-NLS
pXRP08- pLenti2-EF1a-NLS-VP64-NLS-hSpCsn1(10A,840A)-NLS-VP64-EGFP-NLS Constructs have the following names:
pXRPNLS001  pXRPNLS005  pXRPNLS009  pXRPNLS013
pXRPNLS002  pXRPNLS006  pXRPNLS010  pXRPNLS014
pXRPNLS003  pXRPNLS007  pXRPNLS011  pXRPNLS015
pXRPNLS004  pXRPNLS008  pXRPNLS012  pXRPNLS016

Importin alpha NLS sequence:
AAAAGGCCGGCGGCCACGAAAAAGGCCGGCCAGGCAAAAAAGAAAAAG

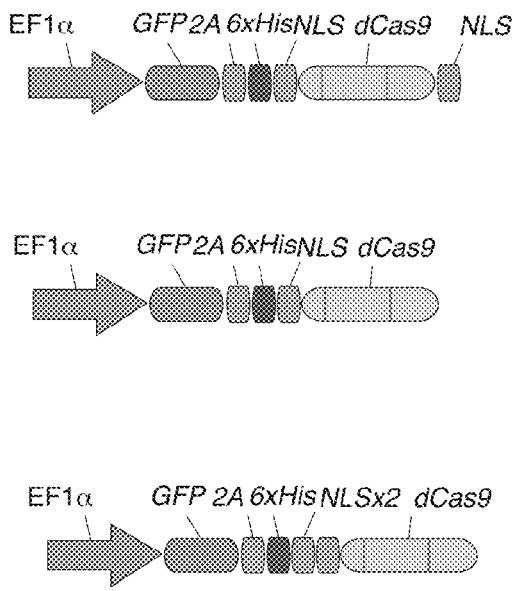
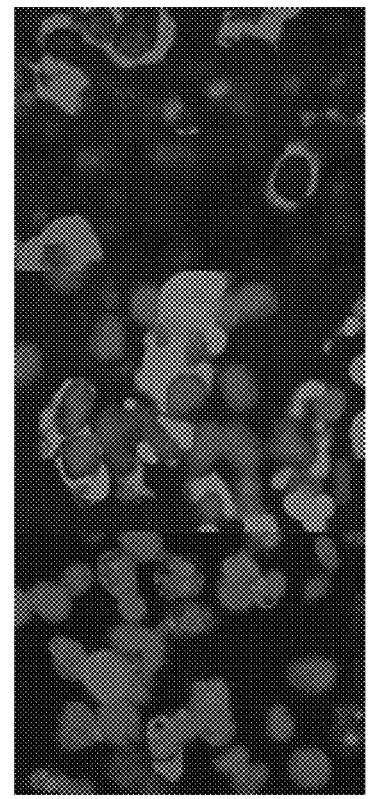
Red = alexa-fluor 594
Blue = DAPI
FIG. 11

From top to bottom:
pXRP001
pXRP005
pXRP007
Cbh-VP64-NLS-dCas9-NLS

From top to bottom:
pXRP015
pXRP013
pXRP011

| |
|---|
| pXRP024-pLenti2-EF1a-VP64-NLS-FLAG-Linker-dCas9-NLS-gLuc-2A-GFP-WPRE |
| pXRP025-pLenti2-EF1a-VP64-NLS-GGGGS₃Linker-dCas9-NLS-gLuc-2A-GFP-WPRE |
| pXRP026-pLenti2-EF1a-VP64-NLS-EAAAK₃Linker-dCas9-NLS-gLuc-2A-GFP-WPRE |
| pXRP027-pLenti2-EF1a-NLS-FLAG-Linker-dCas9-NLS-gLuc-2A-GFP-WPRE |
| pXRP028-pLenti2-EF1a-NLS-GGGGS₃Linker-dCas9-NLS-gLuc-2A-GFP-WPRE |
| pXRP029-pLenti2-EF1a-NLS-EAAAK₃Linker-dCas9-NLS-gLuc-2A-GFP-WPRE |
| pXRP030-pLenti2-pSV40-VP64-NLS-FLAG-Linker-dCas9-NLS-gLuc-2A-GFP-WPRE |
| pXRP031-pLenti2-pPGK-VP64-NLS-FLAG-Linker-dCas9-NLS-gLuc-2A-GFP-WPRE |
| pXRP032-pLenti2-LTR-VP64-NLS-FLAG-Linker-dCas9-NLS-gLuc-2A-GFP-WPRE |
| pXRP033-pLenti2-pSV40-VP64-NLS-GGGGS₃Linker-dCas9-NLS-gLuc-2A-GFP-WPRE |
| pXRP034-pLenti2-pPGK-VP64-NLS-GGGGS₃Linker-dCas9-NLS-gLuc-2A-GFP-WPRE |
| pXRP035-pLenti2-LTR-VP64-NLS-GGGGS₃Linker-dCas9-NLS-gLuc-2A-GFP-WPRE |
| pXRP036-pLenti2-pSV40-VP64-NLS-EAAAK₃Linker-dCas9-NLS-gLuc-2A-GFP-WPRE |
| pXRP037-pLenti2-pPGK-VP64-NLS-EAAAK₃Linker-dCas9-NLS-gLuc-2A-GFP-WPRE |
| pXRP038-pLenti2-LTR-VP64-NLS-EAAAK₃Linker-dCas9-NLS-gLuc-2A-GFP-WPRE |
| pXRP048-pLenti2-EF1a-SID4x-NLS-FLAG-Linker-dCas9-NLS-gLuc-2A-GFP-WPRE |
| pXRP049-pLenti2-EF1a-SID4X-NLS-GGGGS₃Linker-dCas9-NLS-gLuc-2A-GFP-WPRE |
| pXRP050-pLenti2-EF1a-SID4X-NLS-EAAAK₃Linker-dCas9-NLS-gLuc-2A-GFP-WPRE |
| pXRP051-pLenti2-EF1a-KRAB-NLS-FLAG-Linker-dCas9-NLS-gLuc-2A-GFP-WPRE |
| pXRP052-pLenti2-EF1a-KRAB-NLS-GGGGS₃Linker-dCas9-NLS-gLuc-2A-GFP-WPRE |
| pXRP053-pLenti2-EF1a-KRAB-NLS-EAAAK₃Linker-dCas9-NLS-gLuc-2A-GFP-WPRE |
| pXRP054-pLenti2-EF1a-dCas9-Linker-FLAG-NLS-VP64-gLuc-2A-GFP-WPRE |
| pXRP055-pLenti2-EF1a-dCas9-Linker-FLAG-NLS-SID4X-gLuc-2A-GFP-WPRE |
| pXRP056-pLenti2-EF1a-dCas9-Linker-FLAG-NLS-KRAB-gLuc-2A-GFP-WPRE |
| pXRP057-pLenti2-EF1a-dCas9-GGGGGS₃-NLS-VP64-gLuc-2A-GFP-WPRE |
| pXRP058-pLenti2-EF1a-dCas9-GGGGGS₃-NLS-SID4X-gLuc-2A-GFP-WPRE |
| pXRP059-pLenti2-EF1a-dCas9-GGGGGS₃-NLS-KRAB-gLuc-2A-GFP-WPRE |
| pXRP060-pLenti2-EF1a-dCas9-EAAAK₃-NLS-VP64-gLuc-2A-GFP-WPRE |
| pXRP061-pLenti2-EF1a-dCas9-EAAAK₃-NLS-SID4X-gLuc-2A-GFP-WPRE |
| pXRP062-pLenti2-EF1a-dCas9-EAAAK₃-NLS-KRAB-gLuc-2A-GFP-WPRE |
| pXRP024-pLenti2-EF1a-VP64-NLS-FLAG-Linker-Cas9-NLS-gLuc-2A-GFP-WPRE |
| pXRP025-pLenti2-EF1a-VP64-NLS-GGGGS₃Linker-Cas9-NLS-gLuc-2A-GFP-WPRE |
| pXRP026-pLenti2-EF1a-VP64-NLS-EAAAK₃Linker-Cas9-NLS-gLuc-2A-GFP-WPRE |
| pXRP027-pLenti2-EF1a-NLS-FLAG-Linker-Cas9-NLS-gLuc-2A-GFP-WPRE |
| pXRP028-pLenti2-EF1a-NLS-GGGGS₃Linker-Cas9-NLS-gLuc-2A-GFP-WPRE |
| pXRP029-pLenti2-EF1a-NLS-EAAAK₃Linker-Cas9-NLS-gLuc-2A-GFP-WPRE |

FIG. 15A

| |
|---|
| pXRP030-pLenti2-pSV40-VP64-NLS-FLAG-Linker-Cas9-NLS-gLuc-2A-GFP-WPRE |
| pXRP031-pLenti2-pPGK-VP64-NLS-FLAG-Linker-Cas9-NLS-gLuc-2A-GFP-WPRE |
| pXRP032-pLenti2-LTR-VP64-NLS-FLAG-Linker-Cas9-NLS-gLuc-2A-GFP-WPRE |
| pXRP033-pLenti2-pSV40-VP64-NLS-GGGGS$_3$Linker-Cas9-NLS-gLuc-2A-GFP-WPRE |
| pXRP034-pLenti2-pPGK-VP64-NLS-GGGGS$_3$Linker-Cas9-NLS-gLuc-2A-GFP-WPRE |
| pXRP035-pLenti2-LTR-VP64-NLS-GGGGS$_3$Linker-Cas9-NLS-gLuc-2A-GFP-WPRE |
| pXRP036-pLenti2-pSV40-VP64-NLS-EAAAK$_3$Linker-Cas9-NLS-gLuc-2A-GFP-WPRE |
| pXRP037-pLenti2-pPGK-VP64-NLS-EAAAK$_3$Linker-Cas9-NLS-gLuc-2A-GFP-WPRE |
| pXRP038-pLenti2-LTR-VP64-NLS-EAAAK$_3$Linker-Cas9-NLS-gLuc-2A-GFP-WPRE |
| pXRP048-pLenti2-EF1a-SID4x-NLS-FLAG-Linker-Cas9-NLS-gLuc-2A-GFP-WPRE |
| pXRP049-pLenti2-EF1a-SID4X-NLS-GGGGS$_3$Linker-Cas9-NLS-gLuc-2A-GFP-WPRE |
| pXRP050-pLenti2-EF1a-SID4X-NLS-EAAAK$_3$Linker-Cas9-NLS-gLuc-2A-GFP-WPRE |
| pXRP051-pLenti2-EF1a-KRAB-NLS-FLAG-Linker-Cas9-NLS-gLuc-2A-GFP-WPRE |
| pXRP052-pLenti2-EF1a-KRAB-NLS-GGGGS$_3$Linker-Cas9-NLS-gLuc-2A-GFP-WPRE |
| pXRP053-pLenti2-EF1a-KRAB-NLS-EAAAK$_3$Linker-Cas9-NLS-gLuc-2A-GFP-WPRE |
| pXRP054-pLenti2-EF1a-Cas9-Linker-FLAG-NLS-VP64-gLuc-2A-GFP-WPRE |
| pXRP055-pLenti2-EF1a-Cas9-Linker-FLAG-NLS-SID4X-gLuc-2A-GFP-WPRE |
| pXRP056-pLenti2-EF1a-Cas9-Linker-FLAG-NLS-KRAB-gLuc-2A-GFP-WPRE |
| pXRP057-pLenti2-EF1a-Cas9-GGGGGS$_3$-NLS-VP64-gLuc-2A-GFP-WPRE |
| pXRP058-pLenti2-EF1a-Cas9-GGGGGS$_3$-NLS-SID4X-gLuc-2A-GFP-WPRE |
| pXRP059-pLenti2-EF1a-Cas9-GGGGGS$_3$-NLS-KRAB-gLuc-2A-GFP-WPRE |
| pXRP060-pLenti2-EF1a-Cas9-EAAAK$_3$-NLS-VP64-gLuc-2A-GFP-WPRE |
| pXRP061-pLenti2-EF1a-Cas9-EAAAK$_3$-NLS-SID4X-gLuc-2A-GFP-WPRE |
| pXRP062-pLenti2-EF1a-Cas9-EAAAK$_3$-NLS-KRAB-gLuc-2A-GFP-WPRE |

FIG. 15B

FIG. 17
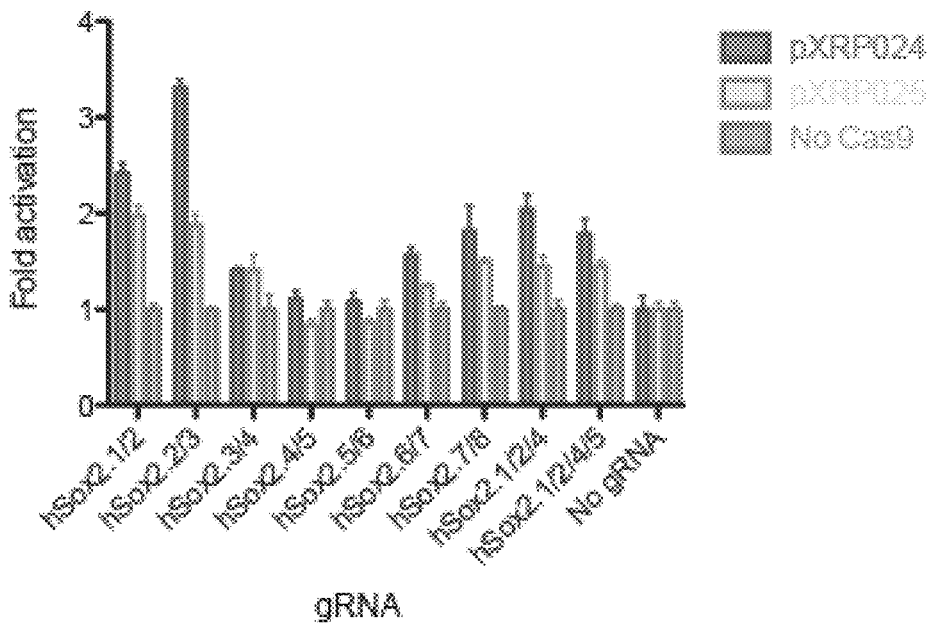
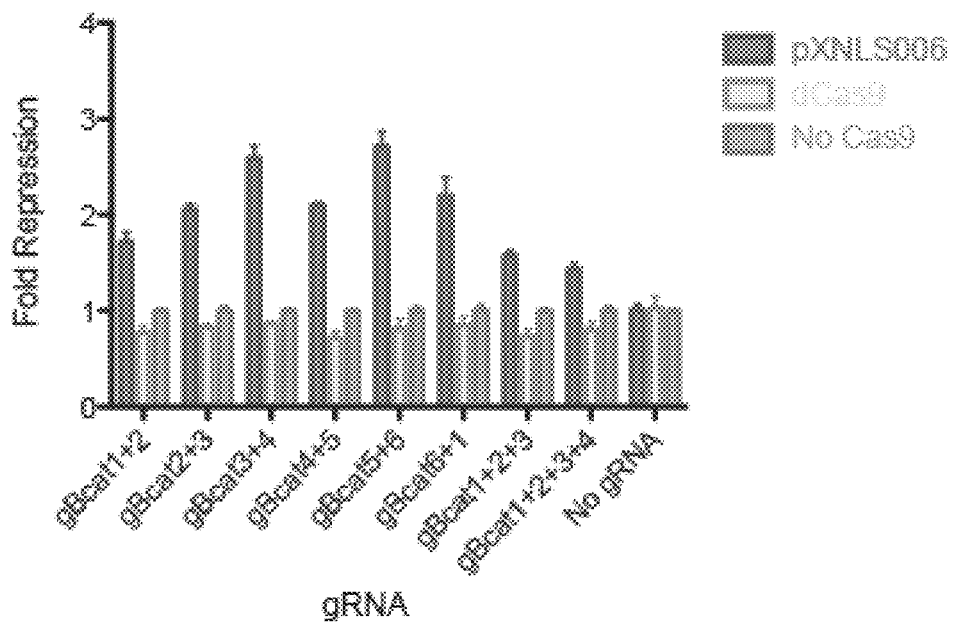
FIG. 18

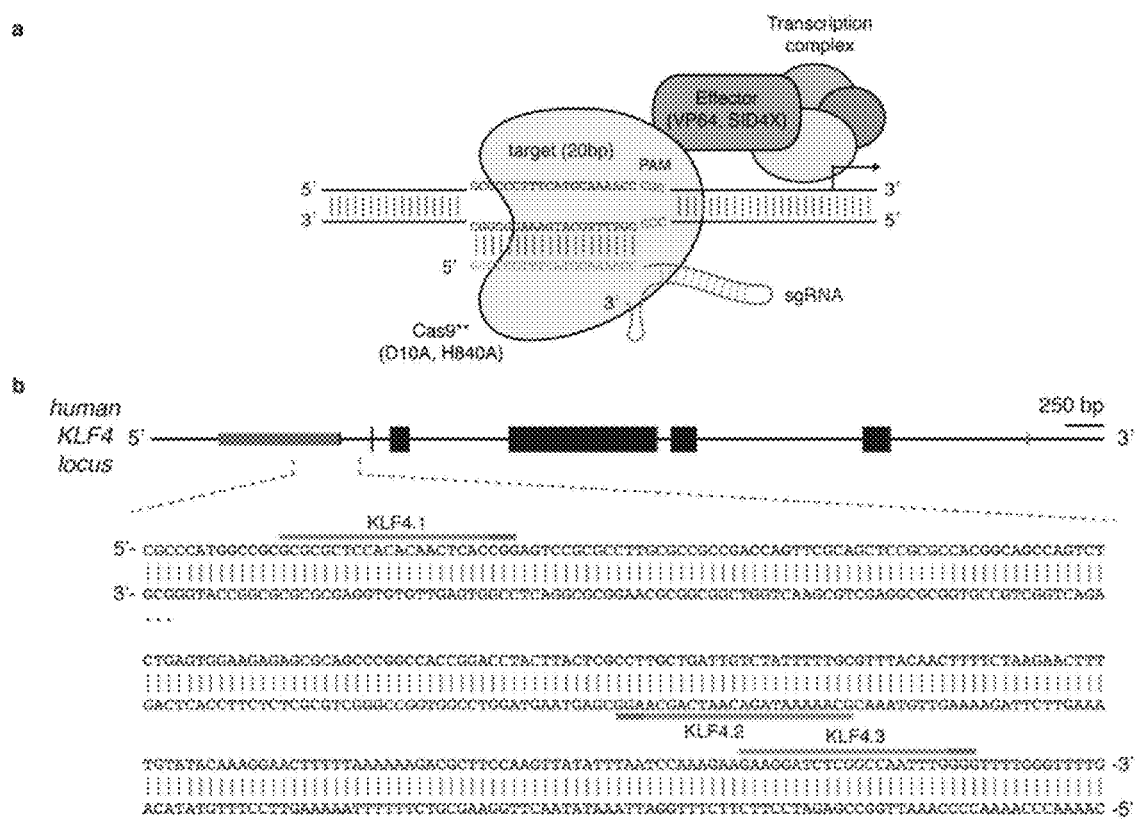
FIG. 23A-B

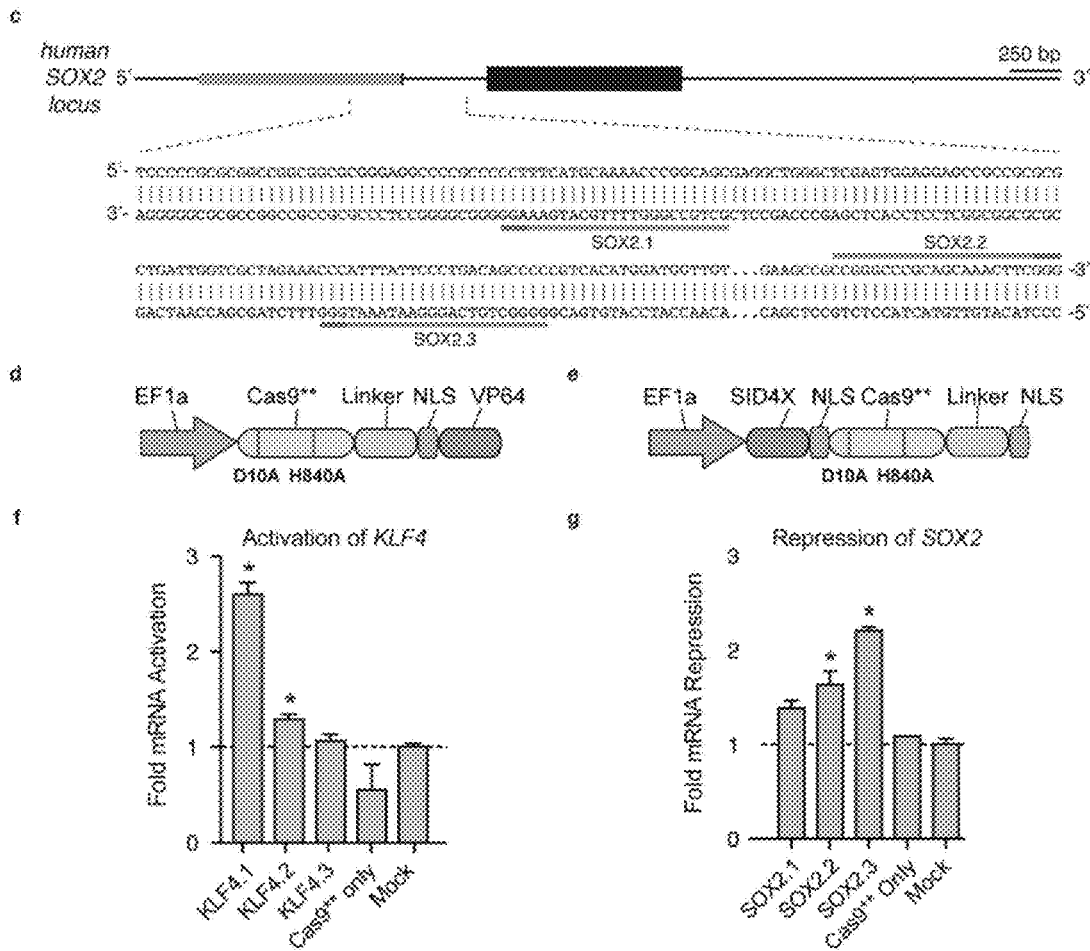
FIG. 23C-G hSpCas9(D10A,H840A)-Linker-NLS-VP64

MDKKYSIGLAIGTNSVGWAVITDEYKVPSKKFKVLGNTDRHSIKKNLIGALLFDSGETA
EATRLKRTARRRYTRRKNRICYLQEIFSNEMAKVDDSFFHRLEESFLVEEDKKHERHPIF
GNIVDEVAYHEKYPTIYHLRKKLVDSTDKADLRLIYLALAHMIKFRGHFLIEGDLNPDNS
DVDKLFIQLVQTYNQLFEENPINASGVDAKAILSARLSKSRRLENLIAQLPGEKKNGLFG
NLIALSLGLTPNFKSNFDLAEDAKLQLSKDTYDDDLDNLLAQIGDQYADLFLAAKNLSD
AILLSDILRVNTEITKAPLSASMIKRYDEHHQDLTLLKALVRQQLPEKYKEIFFDQSKNGY
AGYIDGGASQEEFYKFIKPILEKMDGTEELLVKLNREDLLRKQRTFDNGSIPHQIHLGEL
HAILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPA
FLSGEQKKAIVDLLFKTNRKVTVKQLKEDYFKKIECFDSVEISGVEDRFNASLGTYHDLL
KIIKDKDFLDNEENEDILEDIVLTLTLFEDREMIEERLKTYAHLFDDKVMKQLKRRRYTG
WGRLSRKLINGIRDKQSGKTILDFLKSDGFANRNFMQLIHDDSLTFKEDIQKAQVSGQG
DSLHEHIANLAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQELDINRLSD
YDVDAIVPQSFLKDDSIDNKVLTRSDKNRGKSDNVPSEEVVKKMKNYWRQLLNAKLIT
QRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDPKK
YGGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLKGS
PEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGDSA
GGGGSGGGGSGGGGSCPKKKRKVAAAGSGRADALDDFDLDMLGSDALDDFDLDMLG
SDALDDFDLDMLGSDALDDFDLDMLIN

FIG. 24

SID4X-▓▓-FLAG-Linker-hSpCas9(D10A,H840A)-▓▓

MGSGMNIQMLLEAADYLRRRERREAEHGYASMLPGSGMNIQMLLEAADYLRRRERREAE
HGYASMLPGSGMNIQMLLEAADYLRRRERREAEHGYASMLPGSGMNIQMLLEAADYLE
RRREREAEHGYASMLPSRSA▓▓▓▓▓▓▓▓▓▓▓ADYKDDDDKSRLEPGEKPYKCPECGKSFS
QSGALTRHQRTHTRDKKYSIGLAIGTNSVGWAVITDEYKVPSKKFKVLGNTDRHSIKKN
LIGALLFDSGETAEATRLKRTARRRYTRRKNRICYLQEIFSNEMAKVDDSFFHRLEESFL
VEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLI
AQLPGEKKNGLFGNLIALSLGLTPNFKSNFDLAEDAKLQLSKDTYDDDLDNLLAQIGDQ
YADLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQRTF
DNGSIPHQIHLGELHAILRRQEDFYPFLKDNREKIEKILTFRIPYYVGPLARGNSRFAWMT
RKSEETITPWNFEEVVDKGASAQSFIERMTNFDKNLPNEKVLPKHSLLYEYFTVYNELTK
VKYVTEGMRKPAFLSGEQKKAIVDLLFKTNRKVTVKQLKEDYFKKIECFDSVEISGVED
RFNASLGTYHDLLKIIKDKDFLDNEENEDILEDIVLTLTLFEDREMIEERLKTYAHLFDDK
VMKQLKRRRYTGWGRLSRKLINGIRDKQSGKTILDFLKSDGFANRNFMQLIHDDSLTFK
EDIQKAQVSGQGDSLHEHIANLAGSPAIKKGILQTVKVVDELVKVMGRHKPENIVIEMA
RENQTTQKGQKNSRERMKRIEEGIKELGSQILKEHPVENTQLQNEKLYLYYLQNGRDM
YVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRM
NTKYDENDKLIREVKVITLKSKLVSDFRKDFQFYKVREINNYHHAHDAYLNAVVGTALI
KKYPKLESEFVYGDYKVYDVRKMIAKSEQEIGKATAKYFFYSNIMNFFKTEITLANGEIR
KRPLIETNGETGEIVWDKGRDFATVRKVLSMPQVNIVKKTEVQTGGFSKESILPKRNSDK
LIARKKDWDPKKYGGFDSPTVAYSVLVVAKVEKGKSKKLKSVKELLGITIMERSSFEKN
PIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKH
RDKPIREQAENIIHLFTLTNLGAPAAFKYFDTTIDRKRYTSTKEVLDATLIHQSITGLYETR
IDLSQLGGD▓▓▓▓▓▓▓▓▓▓▓▓▓▓▓

FIG. 25

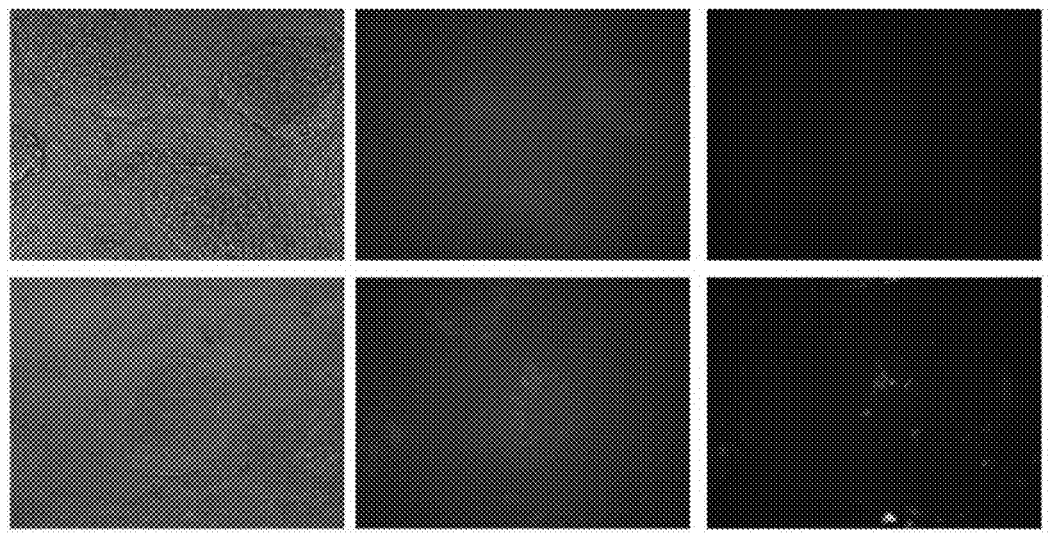
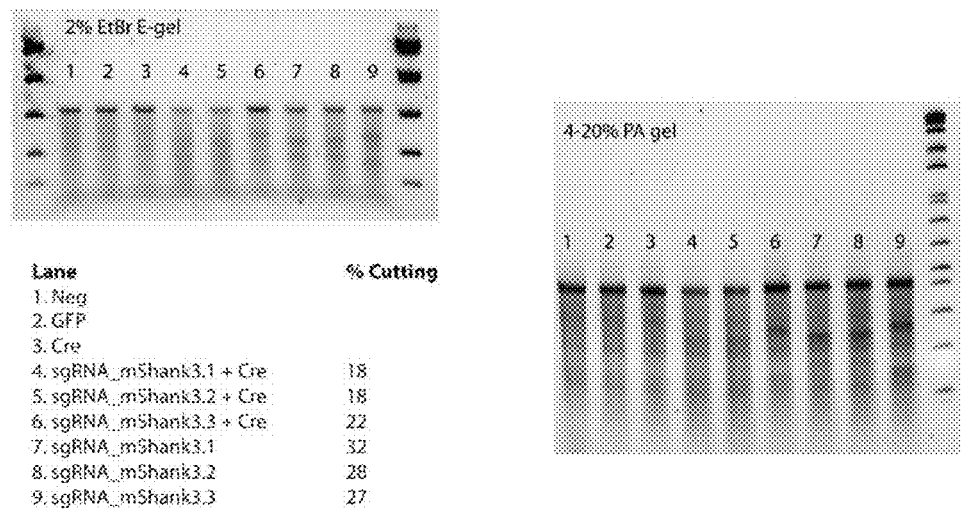
FIG. 32

ENGINEERING AND OPTIMIZATION OF SYSTEMS, METHODS AND COMPOSITIONS FOR SEQUENCE MANIPULATION WITH FUNCTIONAL DOMAINS

RELATED APPLICATIONS AND INCORPORATION BY REFERENCE

This application claims priority to U.S. provisional patent application 61/835,936 entitled ENGINEERING AND OPTIMIZATION OF SYSTEMS, METHODS AND COMPOSITIONS FOR SEQUENCE MANIPULATION WITH FUNCTIONAL DOMAINS FILED ON Jun. 17, 2013. This application also claims priority to US provisional patent applications 61/758,468; 61/769,046; 61/802,174; 61/806,375; 61/814,263; 61/819,803 and 61/828,130 each entitled ENGINEERING AND OPTIMIZATION OF SYSTEMS, METHODS AND COMPOSITIONS FOR SEQUENCE MANIPULATION, filed on Jan. 30, 2013; Feb. 25, 2013; Mar. 15, 2013; Mar. 28, 2013; Apr. 20, 2013; May 6, 2013 and May 28, 2013 respectively. Priority is also claimed to US provisional patent applications 61/736,527 and 61/748,427, both entitled SYSTEMS METHODS AND COMPOSITIONS FOR SEQUENCE MANIPULATION filed on Dec. 12, 2012 and Jan. 2, 2013, respectively. Priority is also claimed to US provisional patent applications 61/791,409 and 61/835,931 both entitled BI-2011/008/44790.02.2003 and BI-2011/008/44790.03.2003 filed on Mar. 15, 2013 and Jun. 17, 2013 respectively.

Reference is also made to US provisional patent applications 61/836,127, 61/836,101, 61/836,080, 61/836,123, and 61/835,973 each filed Jun. 17, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under the NIH Pioneer Award (1DP1MH100706) awarded by the National Institutes of Health. The government has certain rights in the invention.

FIELD OF THE INVENTION

The present invention generally relates to the engineering and optimization of systems, methods and compositions used for the control of gene expression involving sequence targeting, such as genome perturbation or gene-editing, that relate to Clustered Regularly Interspaced Short Palindromic Repeats (CRISPR) and components thereof.

SEQUENCE LISTING

The instant application contains a Sequence Listing which has been submitted electronically in ASCII format and is hereby incorporated by reference in its entirety. Said ASCII copy, created on Nov. 20, 2014, is named 44790.99.2043_SL.txt and is 82,04083,965 bytes in size.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

There exists a pressing need for alternative and robust systems and techniques for sequence targeting with a wide array of applications. Aspects of this invention address this need and provide related advantages. An exemplary CRISPR complex may comprise a CRISPR enzyme complexed with a guide sequence hybridized to a target sequence within the target polynucleotide. The guide sequence is linked to a tracr mate sequence, which in turn hybridizes to a tracr sequence.

In one aspect, the invention relates to one or more elements of a CRISPR system having improved or modified functionality. The CRISPR complex of the invention provides an effective means for modifying a target polynucleotide. The CRISPR complex of the invention has a wide variety of utilities including modifying (e.g., deleting, inserting, translocating, inactivating, activating) a target polynucleotide in a multiplicity of cell types. As such the CRISPR complex of the invention has a broad spectrum of applications in, e.g., gene or genome editing, gene therapy, drug discovery, drug screening, disease diagnosis, and prognosis. An exemplary CRISPR complex may comprise a CRISPR enzyme complexed with a guide sequence hybridized to a target sequence within the target polynucleotide. The guide sequence is linked to a tracr mate sequence, which in turn hybridizes to a tracr sequence.

In some embodiments, a CRISPR/Cas system may comprise: (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex may comprise a CRISPR enzyme complexed with (1) the guide sequence that is hybridized to the target sequence, and (2) the tracr mate sequence that is hybridized to the tracr sequence; and (b) a second regulatory element operably linked to an enzyme-coding sequence encoding said CRISPR enzyme which may comprise a nuclear localization sequence; wherein components (a) and (b) are located on the same or different vectors of the system. In some embodiments, component (a) further may comprise the tracr sequence downstream of the tracr mate sequence under the control of the first regulatory element. In some embodiments, component (a) further may comprise two or more guide sequences operably linked to the first regulatory element, wherein when expressed, each of the two or more guide sequences direct sequence specific binding of a CRISPR complex to a different target sequence in a eukaryotic cell. In some embodiments, the system may comprise the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme may comprise one or more nuclear localization sequences of sufficient strength to drive accumulation of said CRISPR enzyme in a detectable amount in the nucleus of a eukaryotic cell. Without wishing to be bound by theory, it is believed that a nuclear localization sequence is not necessary for CRISPR activity in eukaryotes, but that including such sequences enhances activity of the system. In some embodiments, the CRISPR enzyme is a type II CRISPR system enzyme. In some embodiments, the CRISPR enzyme is a Cas9 enzyme. In some embodiments, the Cas9 enzyme is *S. pyogenes* or *S. thermophilus* Cas9, and may include mutated Cas9 derived from either of these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the invention relate to methods of improving or modifying the target specificity of a CRISPR enzyme (preferably a Cas9 enzyme) which may comprise: a) selecting the CRISPR enzyme having a smaller size for easy packaging into delivery vectors; or b) generating chimeric CRISPR enzymes; or c) utilizing mutated CRISPR (preferably Cas9) enzymes. Further aspects of the invention also relate to methods and compositions for improving target specificity involving two CRISPR enzymes (double nickase), improving the sgRNA scaffold by making improvement to other components aside from the guide RNA.

The invention comprises a non-naturally occurring or engineered composition comprising a vector system that may comprise one or more vectors comprising I. a first regulatory element operably linked to a CRISPR/Cas system chimeric RNA (chiRNA) polynucleotide sequence, wherein the polynucleotide sequence may comprise (a) a guide sequence capable of hybridizing to a target sequence in a cell, (b) a tracr mate sequence, and (c) a tracr sequence, and II. a second regulatory element operably linked to an enzyme-coding sequence encoding a CRISPR enzyme comprising at least one or more nuclear localization sequences, wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridized to the target sequence, and (2) the tracr mate sequence that is hybridized to the tracr sequence, wherein the CRISPR enzyme may comprise two or more mutations, such that the enzyme has altered nuclease activity compared with the wild type enzyme, and wherein the enzyme-coding sequence further encodes one or more heterologous functional domains.

The invention further comprehends a multiplexed two component CRISPR enzyme system composition comprising a vector system that may comprise one or more vectors comprising I. a first regulatory element operably linked to a CRISPR/Cas system chimeric RNA (chiRNA) polynucleotide sequence, wherein the polynucleotide sequence comprises (a) a guide sequence capable of hybridizing to a target sequence in a cell, (b) a tracr mate sequence, and (c) a tracr sequence, and II. a second regulatory element operably linked to an enzyme-coding sequence encoding a CRISPR enzyme may comprise at least one or more nuclear localization sequences, wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridized to the target sequence, and (2) the tracr mate sequence that is hybridized to the tracr sequence, wherein the CRISPR enzyme comprises two or more mutations, such that the enzyme has altered nuclease activity compared with the wild type enzyme, wherein the enzyme-coding sequence further encodes one or more heterologous functional domains, and wherein in the multiplexed system composition multiple chiRNA polynucleotide sequences are used.

The invention further comprehends a non-naturally occurring or engineered composition comprising a vector system that may comprise one or more vectors comprising I. a first regulatory element operably linked to (a) a guide sequence capable of hybridizing to a target sequence in a cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridized to the target sequence, and (2) the tracr mate sequence that is hybridized to the tracr sequence, wherein the CRISPR enzyme may comprise two or more mutations, such that the enzyme has altered nuclease activity compared with the wild type enzyme, and wherein the enzyme-coding sequence further encodes one or more heterologous functional domains.

The invention also comprehends a multiplexed three component CRISPR enzyme system composition comprising a vector system that may comprise one or more vectors comprising I. a first regulatory element operably linked to (a) a guide sequence capable of hybridizing to a target sequence in a cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridized to the target sequence, and (2) the tracr mate sequence that is hybridized to the tracr sequence, wherein the CRISPR enzyme comprises two or more mutations, such that the enzyme has altered nuclease activity compared with the wild type enzyme, wherein the enzyme-coding sequence further encodes one or more heterologous functional domains, and wherein in the multiplexed system composition multiple guide sequences capable of hybridizing to multiple target sequences are used.

In embodiments of the invention the CRISPR enzyme may comprise one or more mutations in two or more catalytically active domains. In another embodiment the CRISPR enzyme has reduced or abolished nuclease activity compared with the wild type enzyme. In another embodiment the two mutations are D10A SpCas9 in a first catalytically active domain and H840A SpCas9 in a second catalytically active domain or corresponding residues of other CRISPR enzymes. In another embodiment the CRISPR enzyme may comprise two or more mutations in a residue selected from the group consisting of D10, E762, H840, N854, N863, or D986. In another embodiment the CRISPR enzyme may comprise two or more mutations selected from the group comprising D10A, E762A, H840A, N854A, N863A or D986A. In a preferred embodiment the CRISPR enzyme is a DNA binding protein that does not direct cleavage of either strand at the location of the target sequence. In an embodiment, each of the two or more mutations is in a catalytically active domain of the CRISPR enzyme selected from the group comprising RuvCI, RuvCII, RuvCIII or HNH domain. It will be understood throughout this application that many references to specific amino acid residues are to those of the SpCas9 enzyme. The skilled person will understand that the invention is applicable to other Cas enzymes, including Cas9 enzymes from other sources, and that where reference is made to specific SpCas9 enzyme residues corresponding alterations and mutations may be made in those other Cas enzymes. For example, the skilled person will be able to compare sequences of the SpCas9 and other enzymes, and identify corresponding residues and domains, and hence to make appropriate modifications to those enzymes.

In further embodiments, the compositions of the invention may comprise at least two or more nuclear localization sequences. In an aspect of the invention the functional domain is a transcriptional activation domain, e.g. VP64. In another aspect the functional domain is a transcriptional repressor domain, e.g. a KRAB domain, a SID domain or a SID4X domain. In another embodiment, the enzyme coding sequence encodes one, two, three, four, five or more heterologous functional domains fused to the CRISPR enzyme. The invention also comprehends one or more linker sequences between any two domains. Embodiments of the invention include one or more functional domains having one or more of the following activities: methylase activity, demethylase activity, transcription activation activity, transcription repression activity, transcription release factor activity, histone modification activity, RNA cleavage activity and nucleic acid binding activity. In another embodiment, the functional domain binds DNA and/or affects transcription of the target nucleic acid. In aspects of the invention the cell is a prokaryotic or eukaryotic cell. In a preferred embodiment, the cell is a mammalian cell or a human cell. In some embodiments, the mammalian cell may be a rodent (for example, mouse or rat) cell, an ungulate cell, or a primate cell. In some embodiments, the eukaryotic cell may be an arthropod (e.g., insect) or nematode cell. In other embodiments the cell may be a plant cell (including algae) or a fungal cell. In further embodiments of the invention the CRISPR enzyme is codon optimized for expression in a eukaryotic cell; the CRISPR enzyme is a type II CRISPR enzyme; the CRISPR enzyme is a Cas9 enzyme and the Cas9 enzyme is from an organism selected from the group comprising of genus *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium* or *Corynebacter*. In a further aspect, the vectors of the system are viral vectors selected from the group comprising of a lentiviral vector, an adenoviral vector or an AAV vector.

The invention also comprehends methods of modulating, i.e. altering, activating, repressing, gene expression at a genomic locus of interest in a cell by contacting the cell with compositions of the invention.

An aspect of the invention relates to a composition which may comprise a vector system which may comprise one or more vectors which may comprise I. a first regulatory element operably linked to a CRISPR/Cas system chimeric RNA (chiRNA) polynucleotide sequence, wherein the polynucleotide sequence may comprise
 (a) a guide sequence capable of hybridizing to a target sequence in a eukaryotic cell,
 (b) a tracr mate sequence, and
 (c) a tracr sequence, and II. a second regulatory element operably linked to an enzyme-coding sequence encoding a CRISPR enzyme which may comprise at least one or more nuclear localization sequences,
 wherein (a), (b) and (c) are arranged in a 5' to 3' orientation,
 wherein components I and II are located on the same or different vectors of the system,
 wherein when transcribed, the tracr mate sequence hybridizes to the tracr sequence and the guide sequence directs sequence-specific binding of a CRISPR complex to the target sequence,
 wherein the CRISPR complex may comprise the CRISPR enzyme complexed with (1) the guide sequence that is hybridized to the target sequence, and (2) the tracr mate sequence that is hybridized to the tracr sequence, and
 wherein the enzyme coding sequence encoding the CRISPR enzyme further encodes a heterologous functional domain.

The coding sequence may encode one or more heterologous functional domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein which may comprise a CRISPR enzyme are described in US20110059502, incorporated herein by reference. In some embodiments, a tagged CRISPR enzyme is used to identify the location of a target sequence.

In an aspect of the invention, the functional domain affects transcription of the target nucleic acid.

Non-limiting examples of CRISPR enzymes include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. These enzymes are known; for example, the amino acid sequence of *S. pyogenes* Cas9 protein may be found in the SwissProt database (available at the website uniprot.org) under accession number Q99ZW2. In some embodiments, the CRISPR enzyme is a Cas9 enzyme. In some embodiments, the Cas9 enzyme is *S. pneumoniae, S.*

*pyogenes* or *S. thermophilus* Cas9, and may include mutated Cas9 derived from these organisms. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity.

In some aspects of the invention, a CRISPR enzyme may comprise one or more mutations and may be used as a generic DNA binding protein with or without fusion to a functional domain. The mutations may include but are not limited to catalytic mutations, for instance mutations in one of the catalytic domains or mutation of catalytic residues. Preferred examples of suitable catalytic mutations are the catalytic residue(s) in the N-term RuvC I domain of Cas9 or the catalytic residue(s) in the internal HNH domain. In some embodiments, the Cas9 is (or is derived from) SpCas9. In such embodiments, preferred mutations are at any or all or positions 10, 762, 840, 854, 863 and/or 986 of SpCas9 or corresponding positions in other Cas9s (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred.

In a more advantageous aspect of the invention the mutated CRISPR enzyme may be fused to a transcriptional activation domain. In one aspect of the invention, the transcriptional activation domain may be VP64. Other aspects of the invention relate to the mutated CRISPR enzyme being fused to domains which include but are not limited to a transcriptional repressor, a recombinase, a transposase, a histone remodeler, a DNA methyltransferase, a cryptochrome, a light inducible/controllable domain or a chemically inducible/controllable domain.

In some aspects of the invention, the CRISPR enzyme is comprised of less than four thousand, and in some aspects less than one thousand, amino acids. Such enzymes may be provided fused to a heterologous functional domain, or not. Where the enzyme is fused to a heterologous functional domain, the size of the enzyme (less than four thousand, less than one thousand amino acids) refers to the CRISPR portion of the fusion protein. In certain embodiments described herein, the invention or method is practiced on an organism or subject. In certain embodiments, the organism or subject is a eukaryote or a non-human eukaryote. In certain embodiments, the organism or subject is a plant. In certain embodiments, the organism or subject is a mammal or a non-human mammal. In certain embodiments, the organism or subject is algae. In some embodiments, the organism or subject may be a rodent (for example, mouse or rat), an ungulate, or a primate. In some embodiments, the organism or subject may be an arthropod (e.g., insect) or nematode. In other embodiments the organism or subject may be a plant or a fungus.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-2F show an exemplary CRISPR system, a possible mechanism of action, an example adaptation for expression in eukaryotic cells, and results of tests assessing nuclear localization and CRISPR activity. FIG. 2C discloses SEQ ID NOS 77 and 78, respectively, in order of appearance. FIG. 2E discloses SEQ ID NOS 79-81, respectively, in order of appearance. FIG. 2F discloses SEQ ID NOS 82-86, respectively, in order of appearance.

Figure 4A:
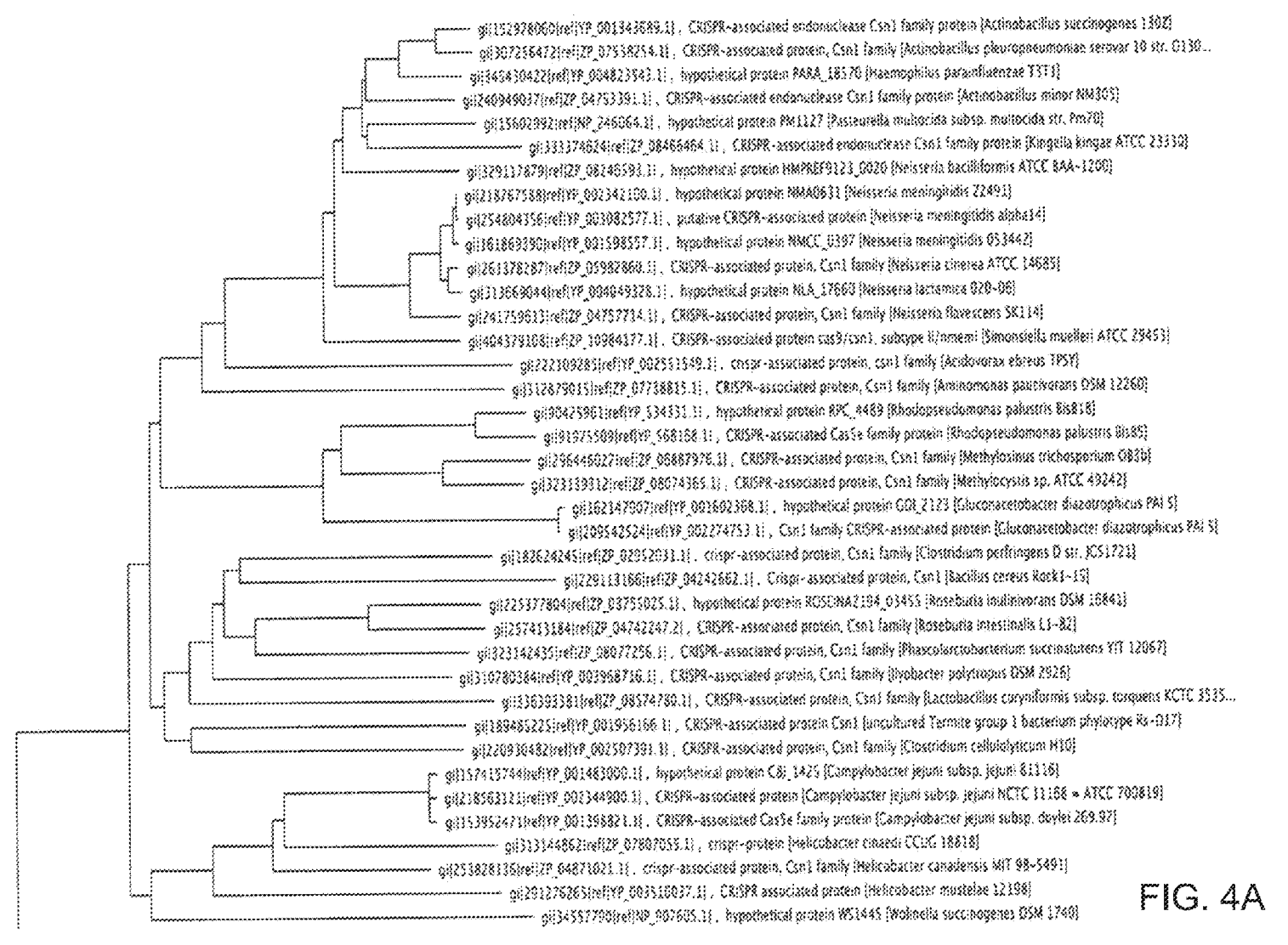

FIGS. 4A-4F show the phylogenetic analysis revealing five families of Cas9s, including three groups of large Cas9s (~1400 amino acids) and two of small Cas9s (~1100 amino acids).

FIG. 11 shows a titrated ratio of chiRNA (Sox2.1 and Sox2.5) to Cas9 (NLS-VP64-NLS-hSpCas9-NLS-VP64-NLS), transfected into 293 cells, and quantified using RT-qPCR. FIG. 11 discloses "6×His" as SEQ ID NO: 1.

FIG. 12 discloses SEQ ID NO: 88 and 45-52, respectively, in order of appearance.

FIGS. 15A-15B shows a list of 31 constructs to explore different linkers, functional domains, and N- and C-term fusions and critical elements. FIGS. 15A and B disclose "GGGGS$_3$," as SEQ ID NO: 35, "EAAAK$_3$," as SEQ ID NO: 36 and "GGGGGS$_3$," as SEQ ID NO: 37.

FIG. 16 discloses "GGGGS$_3$," as SEQ ID NO: 35, "EAAAK$_3$," as SEQ ID NO: 36 and "GGGGGS$_3$," as SEQ ID NO: 37.

FIG. 17 shows a graphical representation of transcriptional activation further to the ratio of chiRNA (Sox2.1 and Sox2.5) to Cas9 (NLS-VP64-NLS-hSpCas9-NLS-VP64-NLS) being titrated and transfected in 293 cells. Results were quantified using Rt-qPCR.

FIG. 18 shows luciferase reporter data for Cas9 activator (top panel) and repressor (bottom panel). Compared to "No Cas9" controls over 3 fold activation was achieved when targeting the promoter of Sox2. When targeting the gene body of beta-catenin (CTNNB1), about 3 fold repression was achieved.

FIG. 23A-G shows a, The RNA-guided nuclease Cas9 from the type II Streptococcus pyogenes CRISPR/Cas system can be converted into a nucleolytically inactive RNA-guided DNA binding protein (Cas9) by introducing two alanine substitutions (D10A and H840A). Schematic showing that a synthetic guide RNA (sgRNA) can direct Cas9-effector fusion to a specific locus in the human genome. The sgRNA contains a 20-bp guide sequence at the 5' end which specifies the target sequence. On the target genomic DNA, the 20-bp target site needs to be followed by a 5'-NGG PAM motif. b, c, Schematics showing the sgRNA target sites in the human KLF4 and SOX2 loci, respectively. Each target site is indicated by the blue bar and the corresponding PAM sequence is indicated by the magenta bar. d, e, Schematics of the Cas9-VP64 transcription activator and SID4X-Cas9 transcription repressor constructs. f, g, Cas9-VP64- and SID4X-Cas9-mediated activation of KLF4 and repression of SOX2, respectively. All mRNA levels were measured relative to GFP mock-transfected 293 FT cells (mean±s.e.m.; n=3 biological replicates). FIG. 23A discloses SEQ ID NOS 89 and 47, respectively, in order of appearance. FIG. 23B discloses SEQ ID NO: 90. FIG. 23C discloses SEQ ID NOS 91 and 92, respectively, in order of appearance.

FIG. 24 shows the Cas9 activator sequence (SEQ ID NO: 93).

FIG. 25 shows the Cas9 repressor sequence (SEQ ID NO: 94).

FIG. 32 shows the validation of Rosa26 Cre-dependent Cas9 knockin mouse embryonic stem cells.

FIG. 34 discloses SEQ ID NOS 95 and 96, respectively, in order of appearance.

Figure 1:
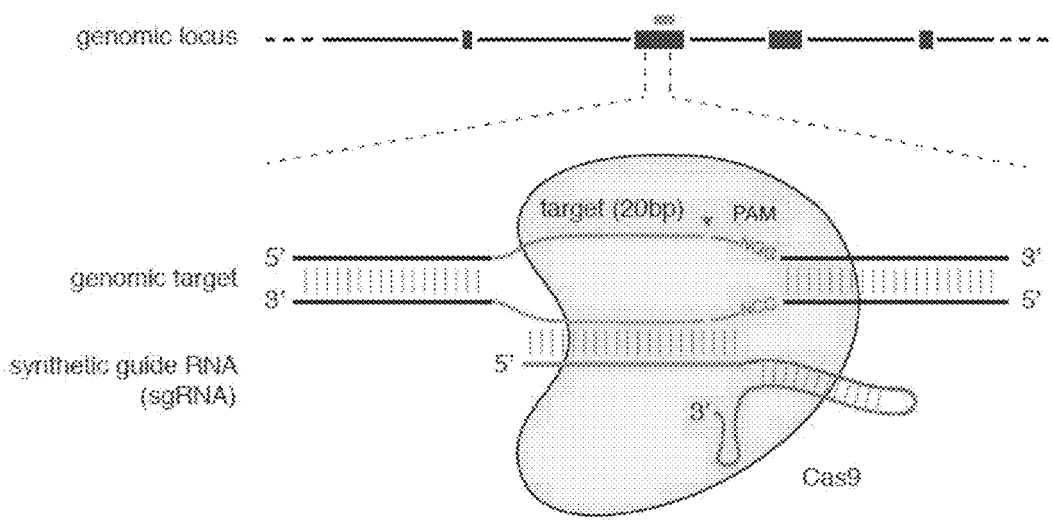
FIG. 1 shows a schematic of RNA-guided Cas9 nuclease. The Cas9 nuclease from *Streptococcus pyogenes* (yellow) is targeted to genomic DNA by a synthetic guide RNA (sgRNA) consisting of a 20-nt guide sequence (blue) and a scaffold (red). The guide sequence base-pairs with the DNA target (blue), directly upstream of a requisite 5'-NGG protospacer adjacent motif (PAM; magenta), and Cas9 mediates a double-stranded break (DSB) ~3 bp upstream of the PAM (red triangle).

The figures herein are for illustrative purposes only and are not necessarily drawn to scale.

DETAILED DESCRIPTION OF THE INVENTION

The invention relates to the engineering and optimization of systems, methods and compositions used for the control of gene expression involving sequence targeting, such as genome perturbation or gene-editing, that relate to the CRISPR/Cas system and components thereof. In advantageous embodiments, the Cas enzyme is Cas9; for example, Cas9 from *S. pyogenes* or *S. thermophilus*.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

As used herein the term "wild type" is a term of the art understood by skilled persons and means the typical form of an organism, strain, gene or characteristic as it occurs in nature as distinguished from mutant or variant forms. For example, "wild type StCas9" refers to wild type Cas9 from *S. thermophilus*, the protein sequence of which is given in the SwissProt database under accession number G3ECR1. Similarly, *S. pyogenes* Cas9 is included in SwissProt under accession number Q99ZW2.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life-eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A.; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

% homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible-reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, 4th Ed.—Chapter 18), FASTA (Altschul et al., 1990 *J Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174(2): 247-50; *FEMS Microbiol Lett.* 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the a-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In one aspect, the invention provides for vectors that are used in the engineering and optimization of CRISPR/Cas systems.

A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 2). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRES- SION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the a-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus may comprise a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In embodiments of the invention the terms guide sequence and guide RNA are used interchangeably. In some embodiments, one or more elements of a CRISPR system is derived from a type I, type II, or type III CRISPR system. In some embodiments, one or more elements of a CRISPR system is derived from a particular organism which may comprise an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In preferred embodiments of the invention, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence NGG following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010, Jan. 15; 37(1): 7.

Figure 2A:
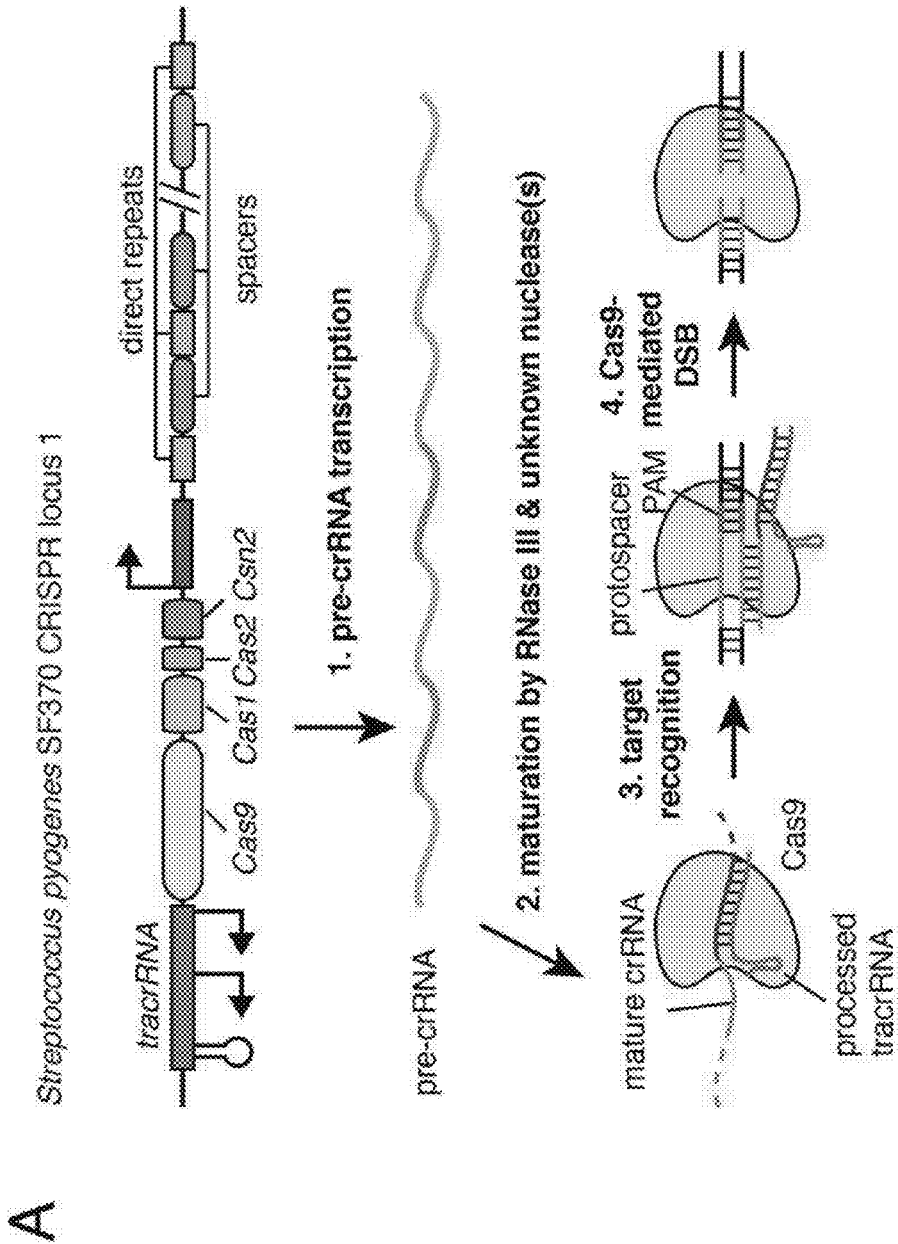
Figure 2C:
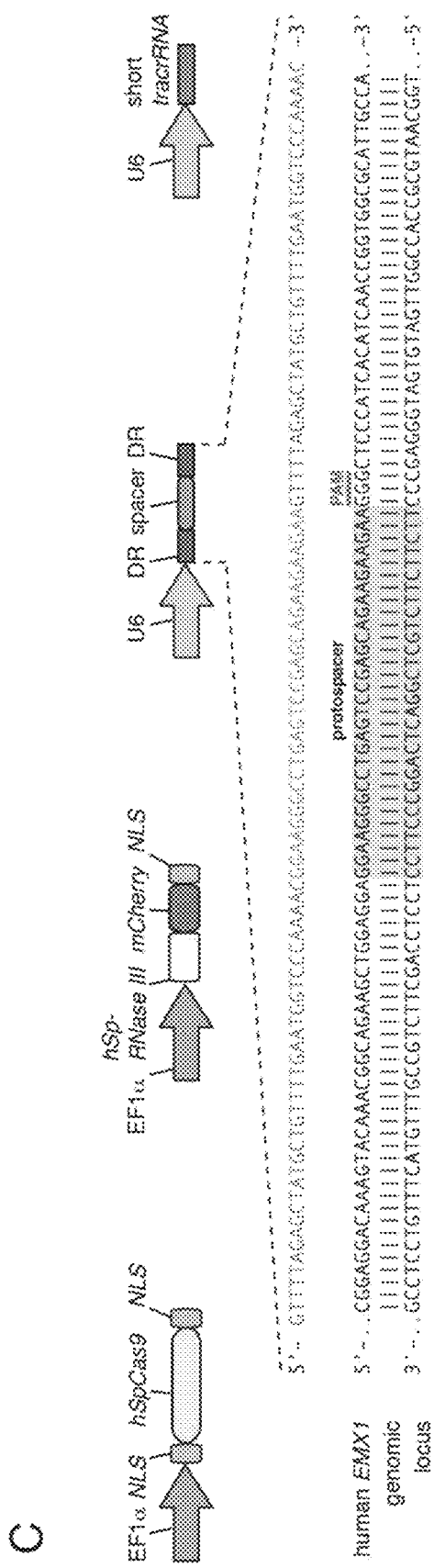
Figure 2D:
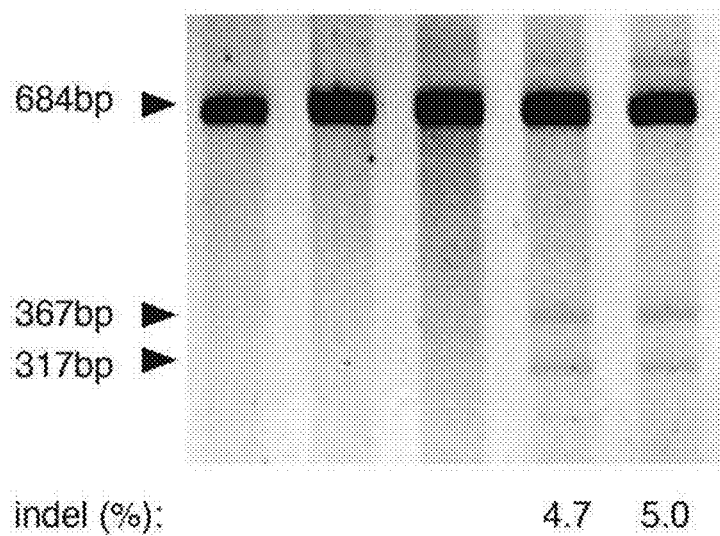
Figure 3A:
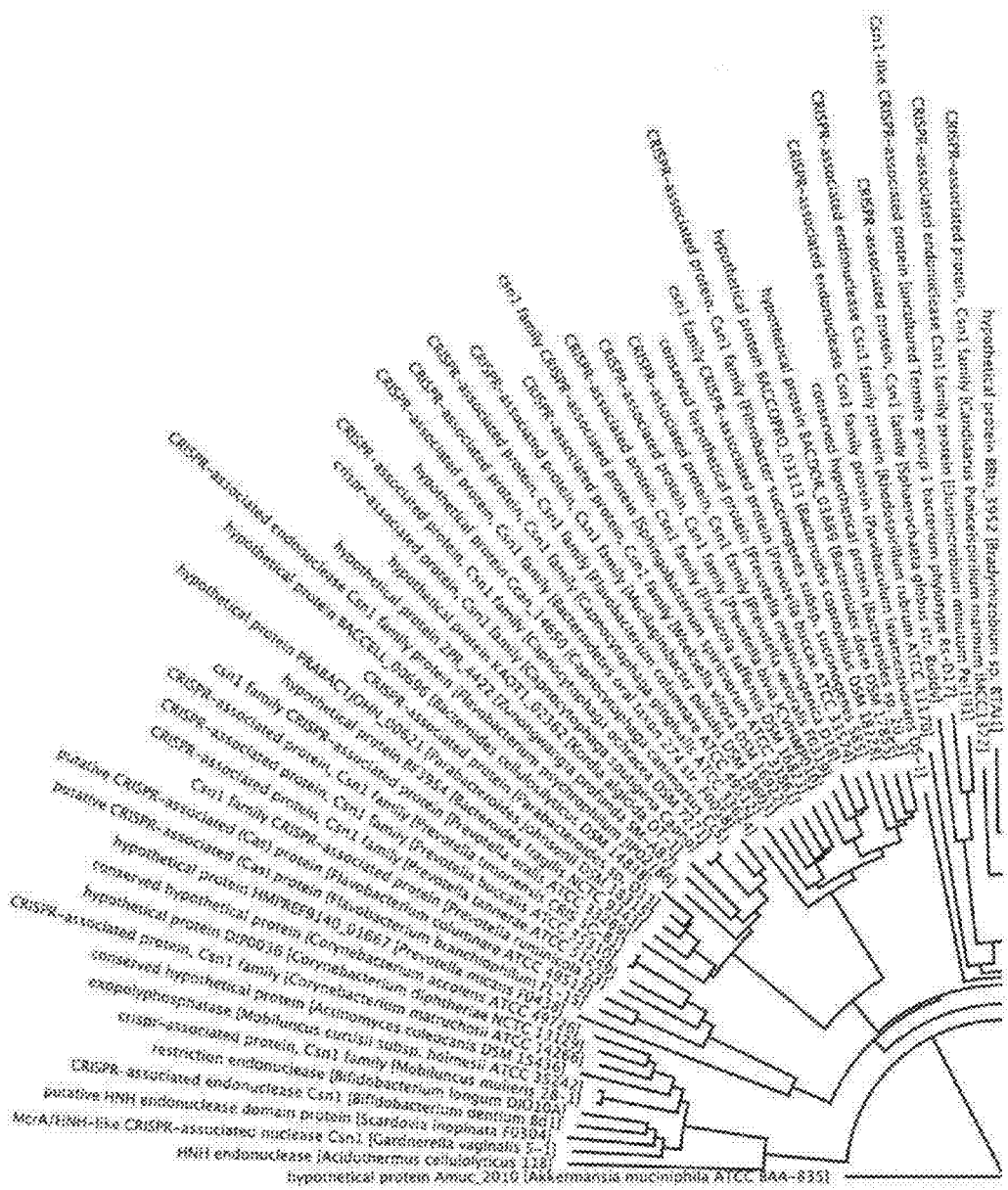
FIG. 3A-D is a phylogenetic tree of Cas genes
Figure 3B:
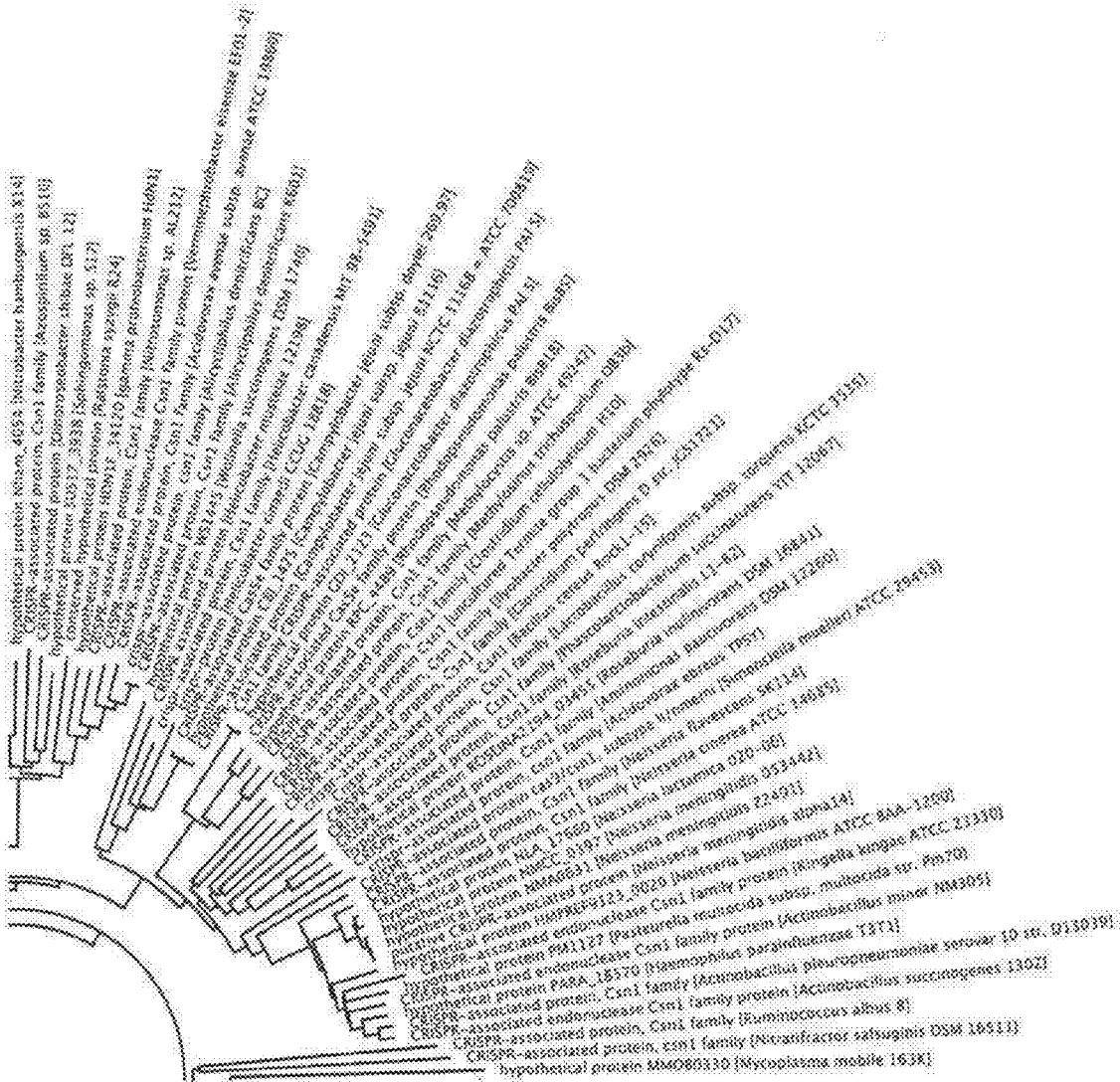
Figure 3C:
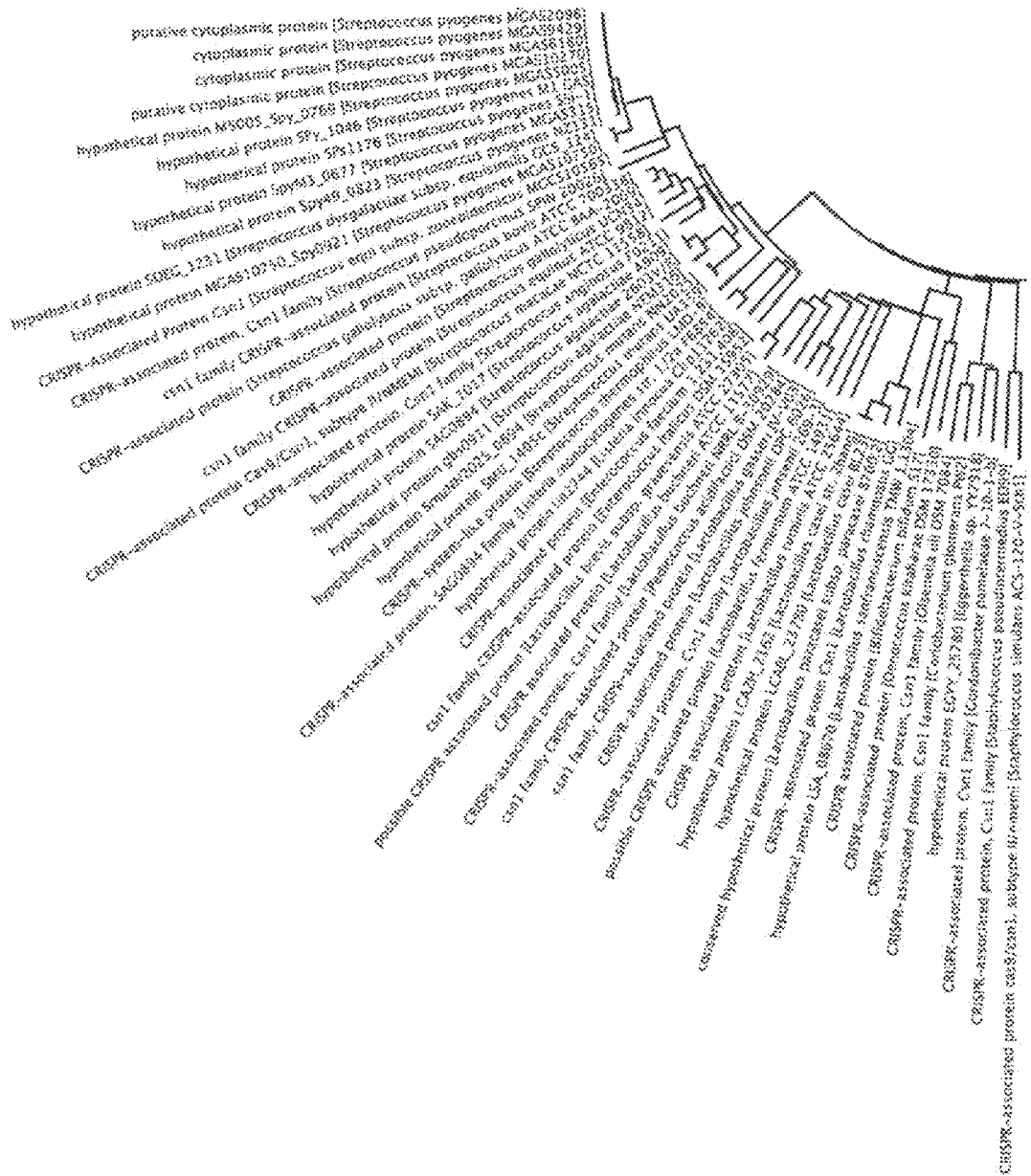
Figure 3D:
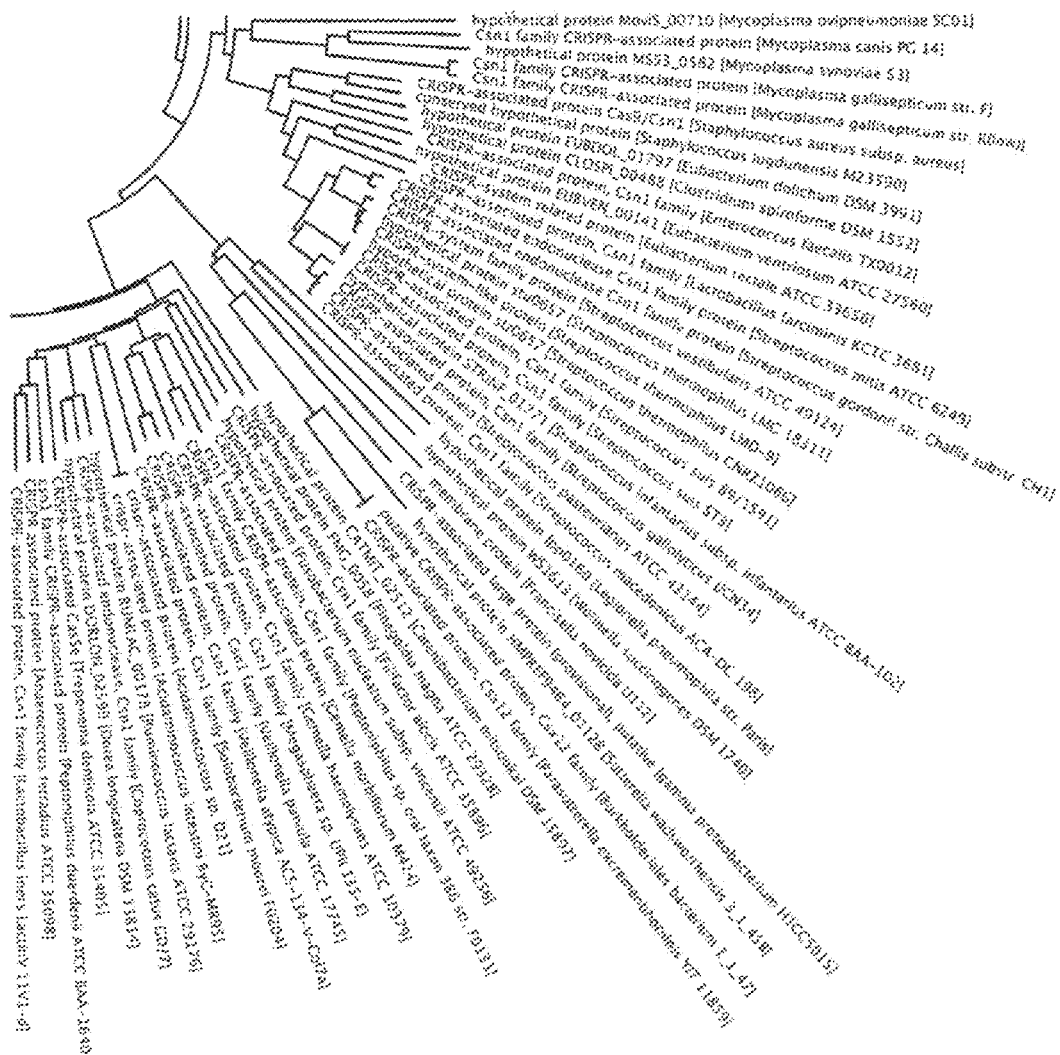
Figure 4B:
Figure 4C:
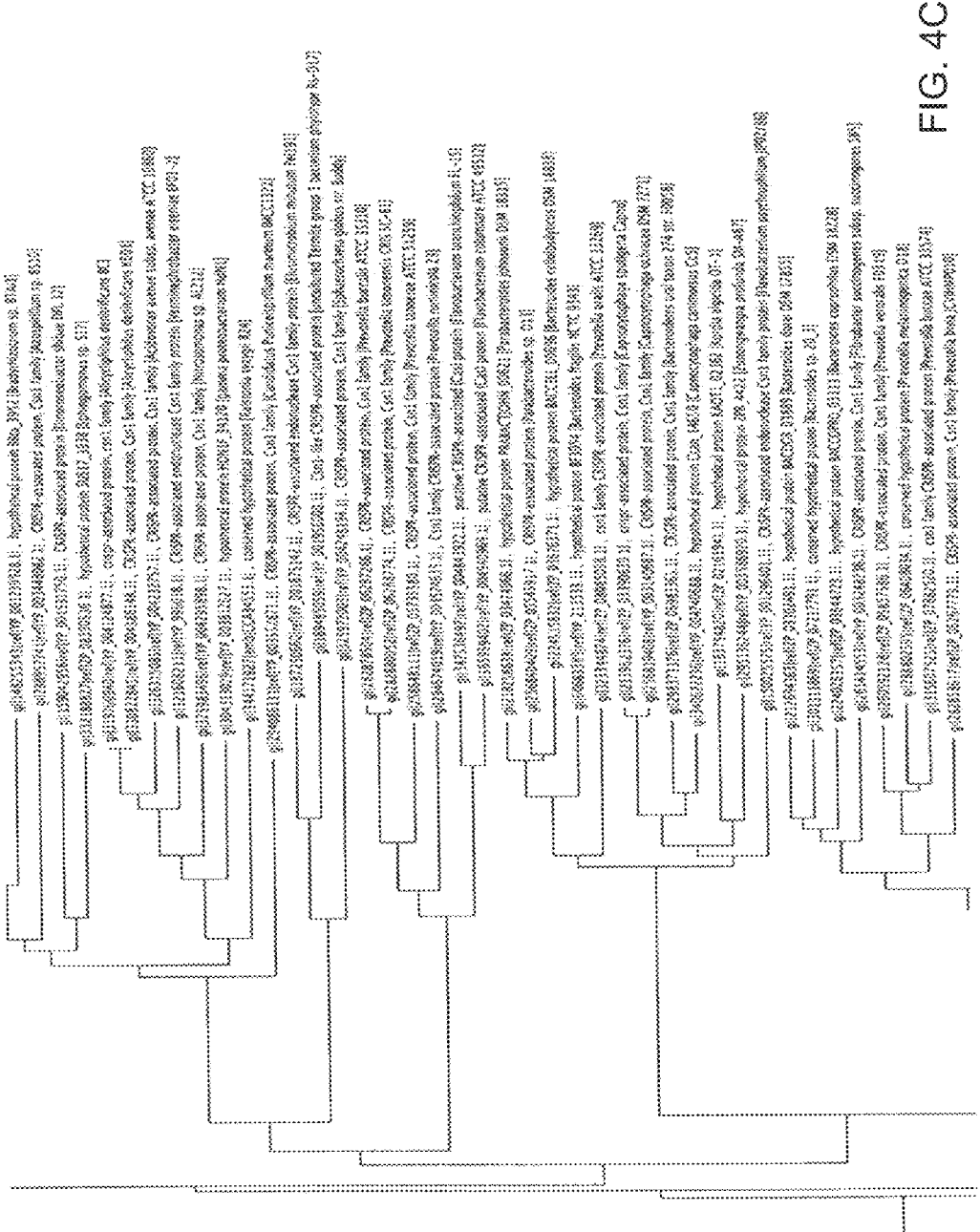
Figure 4D:
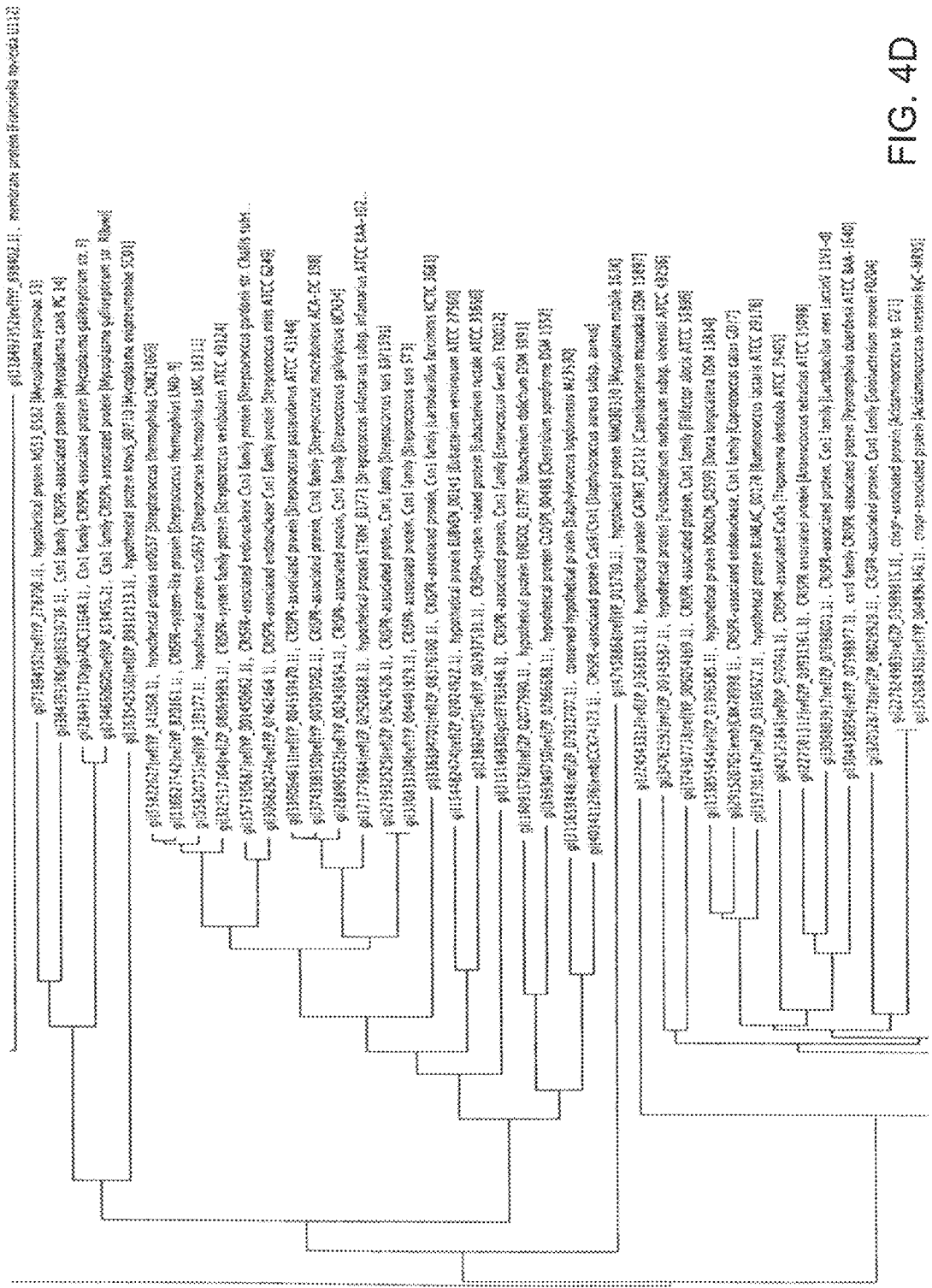
Figure 4E:
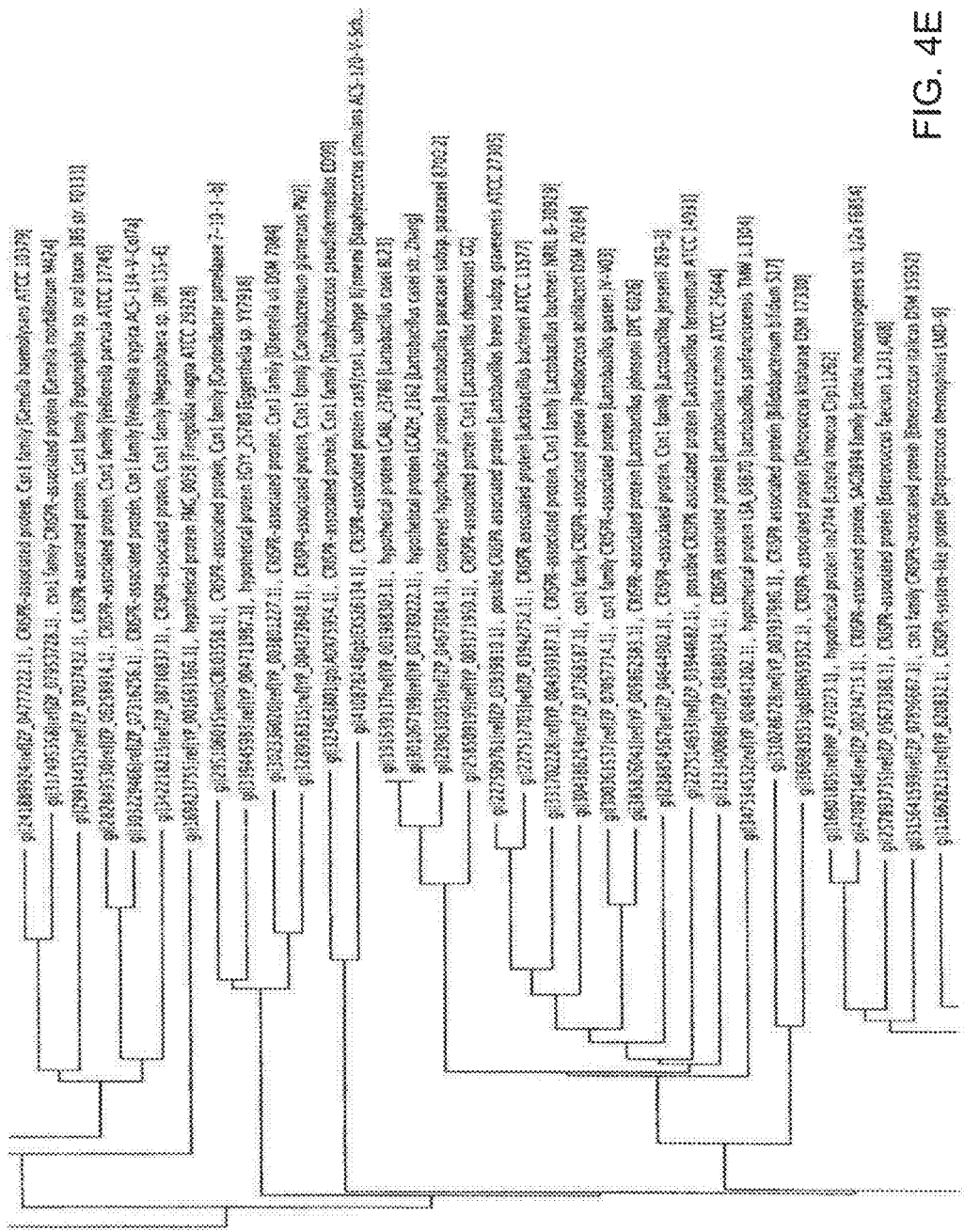
Figure 4F:
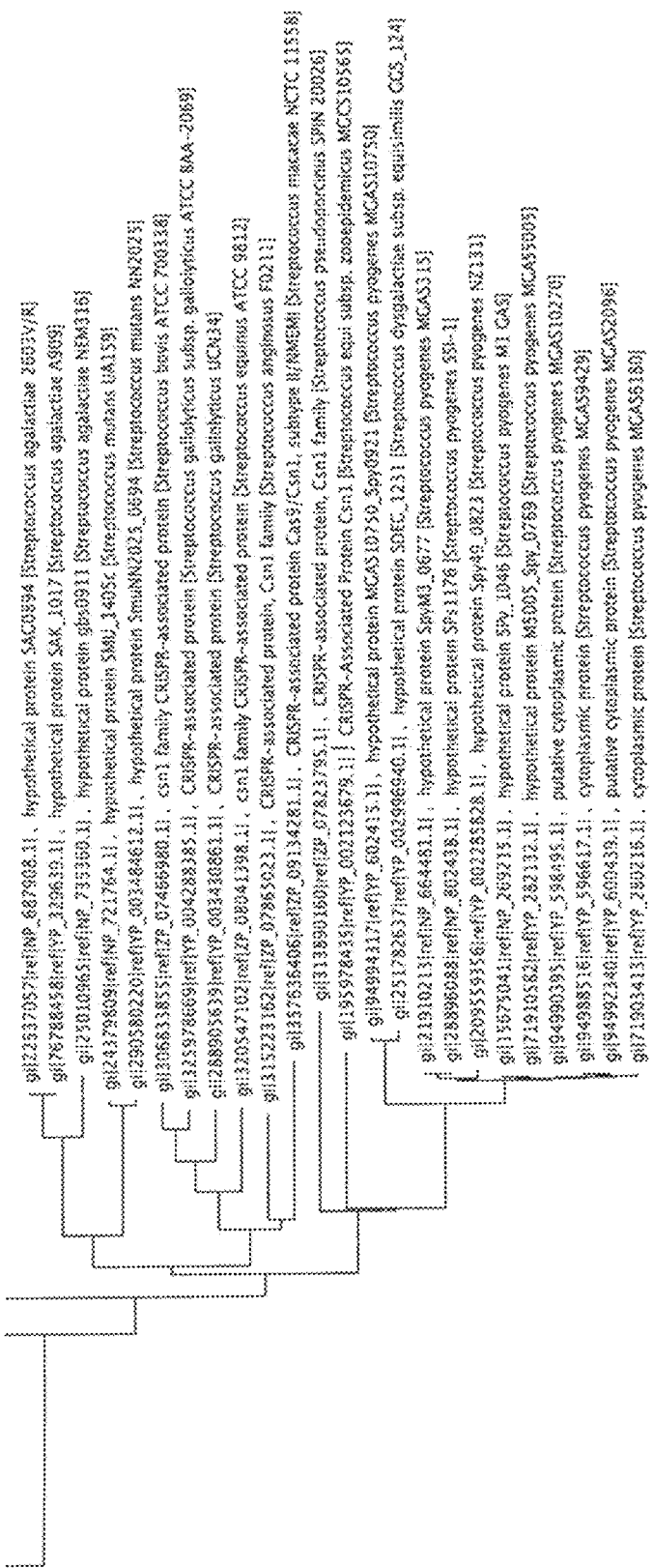

The type II CRISPR locus from *Streptococcus pyogenes* SF370 contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). FIG. 2B demonstrates the nuclear localization of the codon optimized Cas9. To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Typically, in the context of an endogenous CRISPR system, formation of a CRISPR complex (which may comprise a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector may comprise one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector may comprise an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector may comprise two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector may comprise a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools. In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred.

An aspartate-to-alanine substitution (D10A) in the RuvC I catalytic domain of SpCas9 was engineered to convert the nuclease into a nickase (SpCas9n) (see e.g. Sapranauskas et al., 2011, Nucleic Acis Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. Co-expression of EMX1-targeting chimeric crRNA (having the tracrRNA component as well) with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer.

Preferred orthologs are described herein. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/(visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme which may comprise one or more nuclear localization sequences (NLSs), such as about or more than about 1, 2, 3, 4, 5, 6, 7, 8, 9, 10, or more NLSs. In some embodiments, the CRISPR enzyme may comprise about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme may comprise at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 3); the NLS from nucleoplasmin (e.g. the nucleoplasmin bipartite NLS with the sequence KRPAATKKAGQAKKKK (SEQ ID NO: 4)); the c-myc NLS having the amino acid sequence PAAKRVKLD (SEQ ID NO: 5) or RQRRNELKRSP (SEQ ID NO: 6); the hRNPA1 M9 NLS having the sequence NQSSNFGPMKGGNFGGRSSG-PYGGGGQYFAKPRNQGGY (SEQ ID NO: 7); the sequence RMRIZFKNKGKDTAELRRRRVEVSVEL-RKAKKDEQILKRRNV (SEQ ID NO: 8) of the IBB domain from importin-alpha; the sequences VSRKRPRP (SEQ ID NO: 9) and PPKKARED (SEQ ID NO: 10) of the myoma T protein; the sequence PQPKKKPL (SEQ ID NO: 11) of human p53; the sequence SALIKKKKKMAP (SEQ ID NO: 12) of mouse c-abl IV; the sequences DRLRR (SEQ ID NO: 13) and PKQKKRK (SEQ ID NO: 14) of the influenza virus NS1; the sequence RKLKKKIKKL (SEQ ID NO: 15) of the Hepatitis virus delta antigen; the sequence REKKKFLKRR (SEQ ID NO: 16) of the mouse Mx1 protein; the sequence KRKGDEVDGVDEVAKKKSKK (SEQ ID NO: 17) of the human poly(ADP-ribose) polymerase; and the sequence RKCLQAGMNLEARKTKK (SEQ ID NO: 18) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMMNNNNNNNNNNNNXGG (SEQ ID NO: 97) where NNNNNNNNNNNNXGG (SEQ ID NO: 98) (N is A, G, T, or C; and X can be anything) has a single occurrence in the genome. A unique target sequence in a genome may include an *S. pyogenes* Cas9 target site of the form MMMMMMMMMNNNNNNNNNNNNXGG (SEQ ID NO: 99) where NNNNNNNNNNNNXGG (SEQ ID NO: 100) (N is A, G, T, or C; and X can be anything) has a single occurrence in the genome. For the *S. thermophilus* CRISPR1 Cas9, a unique target sequence in a genome may include a Cas9 target site of the form MMMMMMMMMNNNNNNNNNNNNXXAGAAW (SEQ ID NO: 19) where NNNNNNNNNNNNXXAGAAW (SEQ ID NO: 20) (N is A, G, T, or C; X can be anything; and W is A or T) has a single occurrence in the genome. A unique target sequence in a genome may include an *S. thermophilus* CRISPR1 Cas9 target site of the form MMMMMMMMMNNNNNNNNNNNNXXAGAAW (SEQ ID NO: 21) where NNNNNNNNNNNNXXAGAAW (SEQ ID NO: 22) (N is A, G, T, or C; X can be anything; and W is A or T) has a single occurrence in the genome. For the *S. pyogenes* Cas9, a unique target sequence in a genome may include a Cas9 target site of the form MMMMMMMMMNNNNNNNNNNNNXGGXG (SEQ ID NO: 101) where NNNNNNNNNNNNXGGXG (SEQ ID NO: 102) (N is A, G, T, or C; and X can be anything) has a single occurrence in the genome. A unique target sequence in a genome may include an *S. pyogenes* Cas9 target site of the form MMMMMMMMMNNNNNNNNNNNNXGGXG (SEQ ID NO: 103) where NNNNNNNNNNNNXGGXG (SEQ ID NO: 104) (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechnology* 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex may comprise the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides which may comprise a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttg-tactctcaagatttaGAAAtaaatcttgcagaagctacaaagataaggctt cat-gccgaaatcaacaccctgtcattttatggcagggtgttttcgttatttaaTTTTTT (SEQ ID NO: 23); (2) NNNNNNNNNNNNNNNNNNNNgttttg-tactctcaGAAAtgcagaagctacaaagataaggcttcatgccgaaatca acaccctgtcattttatggcagggtgttttcgttatttaaTTTTTT (SEQ ID NO: 24); (3) NNNNNNNNNNNNNNNNNNNNgttttg-tactctcaGAAAtgcagaagctacaaagataaggcttcatgccgaaatca acaccctgtcattttatggcagggtgtTTTTTT (SEQ ID NO: 25); (4) NNNNNNNNNNNNNNNNNNNNgtttta-gagctaGAAAtagcaagttaaaataaggctagtccgttatcaacttgaaaa agtggcaccgagtcggtgcTTTTTT (SEQ ID NO: 26); (5) NNNNNNNNNNNNNNNNNNNNgtttta-gagctaGAAATAGcaagttaaaataaggctagtccgttatcaacttgaa aaagtgTTTTTTT (SEQ ID NO: 27); and (6) NNNNNNNNNNNNNNNNNNNNgtttta-gagctagAAATAGcaagttaaaataaggctagtccgttatcaTTTTT TTT (SEQ ID NO: 28). In some embodiments, sequences (1) to (3) are used in combination with Cas9 from *S. thermophilus* CRISPR1 In some embodiments, sequences (4) to (6) are used in combination with Cas9 from *S. pyogenes*. In some embodiments, the tracr sequence is a separate transcript from a transcript which may comprise the tracr mate sequence.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide which may comprise the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide which may comprise a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein which may comprise one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein which may comprise a CRISPR enzyme are described in US20110059502, incorporated herein by reference. In some embodiments, a tagged CRISPR enzyme is used to identify the location of a target sequence.

In some aspects, the invention provides methods which may comprise delivering one or more polynucleotides, such as or one or more vectors as described herein, one or more transcripts thereof, and/or one or proteins transcribed therefrom, to a host cell. In some aspects, the invention further provides cells produced by such methods, and animals which may comprise or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line which may comprise one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line which may comprise cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. Methods for producing transgenic plants and animals are known in the art, and generally begin with a method of cell transfection, such as described herein.

With recent advances in crop genomics, the ability to use CRISPR-Cas systems to perform efficient and cost effective gene editing and manipulation will allow the rapid selection and comparison of single and and multiplexed genetic manipulations to transform such genomes for improved production and enhanced traits. In this regard reference is made to US patents and publications: U.S. Pat. No. 6,603,061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 December 29; 13(2):85-96 are also herein incorporated by reference in their entirety. In an advantageous embodiment of the invention, the CRISPR/Cas9 system is used to engineer microalgae. Accordingly, reference herein to animal cells may also apply, mutatis mutandis, to plant cells unless otherwise apparent.

In plants, pathogens are often host-specific. For example, *Fusarium oxysporum* f. sp. *lycopersici* causes tomato wilt but attacks only tomato, and *F. oxysporum f. dianthii Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant (including micro-algae). For re-introduced cells it is particularly preferred that the cells are stem cells.

In one aspect, the invention provides for methods of modifying a target polynucleotide in a eukaryotic cell. In some embodiments, the method may comprise allowing a CRISPR complex to bind to the target polynucleotide to effect cleavage of said target polynucleotide thereby modifying the target polynucleotide, wherein the CRISPR complex may comprise a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method may comprise allowing a CRISPR complex to bind to the polynucleotide such that said binding results in increased or decreased expression of said polynucleotide; wherein the CRISPR complex may comprise a CRISPR enzyme complexed with a guide sequence hybridized to a target sequence within said polynucleotide, wherein said guide sequence is linked to a tracr mate sequence which in turn hybridizes to a tracr sequence.

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit may comprise one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit may comprise one or more oligonucleotides corresponding to a guide sequence for insertion into a vector so as to operably link the guide sequence and a regulatory element. In some embodiments, the kit may comprise a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex may comprise a CRISPR enzyme complexed with a guide sequence hybridized to a target sequence within the target polynucleotide. The guide sequence is linked to a tracr mate sequence, which in turn hybridizes to a tracr sequence.

In one embodiment, this invention provides a method of cleaving a target polynucleotide. The method may comprise modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template which may comprise a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template may comprise a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template.

In other embodiments, this invention provides a method of modifying expression of a polynucleotide in a eukaryotic cell. The method may comprise increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences.

The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knock-out" of the target sequence.

A method of the invention may be used to create a plant, an animal or cell that may be used as a disease model. As used herein, "disease" refers to a disease, disorder, or indication in a subject. For example, a method of the invention may be used to create an animal or cell that may comprise a modification in one or more nucleic acid sequences associated with a disease, or an animal or cell in which the expression of one or more nucleic acid sequences associated with a disease are altered. Such a nucleic acid sequence may encode a disease associated protein sequence or may be a disease associated control sequence.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method may comprise modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method may comprise contacting a test compound with a cell which may comprise one or more vectors that drive expression of one or more of a CRISPR enzyme, a guide sequence linked to a tracr mate sequence, and a tracr sequence; and detecting a change in a readout that is indicative of a reduction or an augmentation of a cell signaling event associated with, e.g., a mutation in a disease gene contained in the cell.

A cell model or animal model can be constructed in combination with the method of the invention for screening a cellular function change. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, Sambrook, et al., (1989); Nonradioactive In Situ Hybridization Application Manual, Boehringer Mannheim, second edition. The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2α). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex may include a number of disease-associated genes and polynucleotides as well as signaling biochemical pathway-associated genes and polynucleotides as listed in US provisional patent applications 61/736,527 and 61/748,427, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from US Provisional applications 61/736,527 filed Dec. 12, 2012 and 61/748,427 filed Jan. 2, 2013. Such genes, proteins and pathways may be the target polynucleotide of a CRISPR complex.

TABLE A

| DISEASE/DISORDERS | GENE(S) |
| --- | --- |
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Nctsn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
| --- | --- |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |

TABLE B-continued

| | |
|---|---|
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), IL-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, |

TABLE B-continued

| | |
|---|---|
| | Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |

TABLE C-continued

| CELLULAR FUNCTION | GENES |
|---|---|
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |

TABLE C-continued

| CELLULAR FUNCTION | GENES |
|---|---|
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |

TABLE C-continued

| CELLULAR FUNCTION | GENES |
|---|---|
| IL-6 Signaling | HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3 |

TABLE C-continued

| CELLULAR FUNCTION | GENES |
|---|---|
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |

TABLE C-continued

| CELLULAR FUNCTION | GENES |
|---|---|
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |

TABLE C-continued

| CELLULAR FUNCTION | GENES |
| --- | --- |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011-Medical). Specific aspects of tandem repeat sequences have been found to be responsible for more than twenty human diseases (New insights into repeat instability: role of RNA•DNA hybrids. McIvor E I, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN asn so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion-related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to a-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin I2 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch1, Notch2, Notch3, or Notch4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS 1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease-Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Improvement of the Cas9 System for In Vivo Application

Applicants conducted a Metagenomic search for a Cas9 with small molecular weight. Most Cas9 homologs are fairly large. For example the SpCas9 is around 1368aa long, which is too large to be easily packaged into viral vectors for delivery.

Through computational analysis, Applicants found that in the bacterial strain *Campylobacter*, there are two Cas9 proteins with less than 1000 amino acids. The sequence for one Cas9 from *Campylobacter jejuni* is presented below. At this length, CjCas9 can be easily packaged into AAV, lentiviruses, Adenoviruses, and other viral vectors for robust delivery into primary cells and in vivo in animal models. In a preferred embodiment of the invention, the Cas9 protein from *S. aureus* is used.

```
                                                     (SEQ ID NO: 29)
>Campylobacter jejuni Cas9 (CjCas9)
MARILAFDIGISSIGWAFSENDELKDCGVRIFTKVENPKTGESLALPRRLARSARKRLARR

KARLNHLKHLIANEFKLNYEDYQSFDESLAKAYKGSLISPYELRFRALNELLSKQDFAR

VILHIAKRRGYDDIKNSDDKEKGAILKAIKQNEEKLANYQSVGEYLYKEYFQKFKENSK

EFTNVRNKKESYERCIAQSFLKDELKLIFKKQREFGFSFSKKFEEEVLSVAFYKRALKDFS

HLVGNCSFFDEKRAPKNSPLAFMFVALTRIINLLNNLKNTEGILYTKDDLNALLNEVLK

NGTLTYKQTKKLLGLSDDYEFKGEKTYFIEFKKYKEFIKALGEHNLSQDDLNEIAKDIT
```

```
LIKDEIKLKKALAKYDLNQNQIDSLSKLEFKDHLNISFKALKLVTPLMLEGKKYEACNE
LNLKVAINEDKKDFLPAFNETYYKDEVTNPVVLRAIKEYRKVLNALLKKYGKVHKINIE
LAREVGKNHSQRAKIEKEQNENYKAKKDAELECEKLGLKINSKNILKLRLFKEQKEFCA
YSGEKIKISDLQDEKMLEIDHIYPYSRSFDDSYMNKVLVFTKQNQEKLNQTPFEAFGNDS
AKWQKIEVLAKNLPTKKQKRILDKNYKDKEQKNFKDRNLNDTRYIARLVLNYTKDYL
DFLPLSDDENTKLNDTQKGSKVHVEAKSGMLTSALRHTWGFSAKDRNNHLHHAIDAVI
IAYAMMSIVKAFSDFKKEQESNSAELYAKKISELDYKNKRKFFEPFSGFRQKVLDKIDEIF
VSKPERKKPSGALHEETFRKEEEFYQSYGGKEGVLKALELGKIRKVNGKIVKNGDMFR
VDIFKHKKTNKFYAVPIYTMDFALKVLPNKAVARSKKGEIKDWILMDENYEFCFSLYK
DSLILIQTKDMQEPEFVYYNAFTSSTVSLIVSKHDNKFETLSKNQKILFKNANEKEVIAKS
IGIQNLKVFEKYIVSALGEVTKAEFRQREDFKK.
```

The putative tracrRNA element for this CjCas9 is:

(SEQ ID NO: 30)
```
TATAATCTCATAAGAAATTTAAAAAGGGACTAAAATAAAGAGTTTGCGGG
ACTCTGCGGGGTTACAATCCCCTAAAACCGCTTTTAAAATT
```

The Direct Repeat sequence is:

(SEQ ID NO: 31)
```
ATTTTACCATAAAGAAATTTAAAAAGGGACTAAAAC
```

An example of a chimeric guideRNA for CjCas9 is:

(SEQ ID NO: 32)
```
NNNNNNNNNNNNNNNNNNNNGUUUUAGUCCCGAAAGGGACUAAAAUAAAG
AGUUUGCGGGACUCUGCGGGGUUACAAUCCCCUAAAACCGCUUUU
```

Example 2

Cas9 Optimization

For enhanced function or to develop new functions, Applicants generate chimeric Cas9 proteins by combining fragments from different Cas9 homologs. For example, two example chimeric Cas9 proteins:

For example, Applicants fused the N-term of St1Cas9 (fragment from this protein is in bold) with C-term of SpCas9 (fragment from this protein is underlined).

(SEQ ID NO: 33)
```
>St1(N)Sp(C)Cas9
MSDLVLGLDIGIGSVGVGILNKVTGEIIHKNSRIFPAAQAENNLVRRTNRQGRRLAR
RKKHRRVRLNRLFEESGLITDFTKISINLNPYQLRVKGLTDELSNEELFIALKNMVK
HRGISYLDDASDDGNSSVGDYAQIVKENSKQLETKTPGQIQLERYQTYGQLRGDFT
VEKDGKKHRLINVFPTSAYRSEALRILQTQQEFNPQITDEFINRYLEILTGKRKYYH
GPGNEKSRTDYGRYRTSGETLDNIFGIIGKCTFYPDEFRAAKASYTAQEFNLLNDL
NNLTVPTETKKLSKEQKNQIINYVKNEKAMGPAKLFKYIAKLLSCDVADIKGYRID
KSGKAEIHTFEAYRKMKTLETLDIEQMDRETLDKLAYVLTLNTEREGIQEALEHEF
ADGSFSQKQVDELVQFRKANSSIFGKGWHNFSVKLMMELIPELYETSEEQMTILTR
LGKQKTTSSSNKTKYIDEKLLTEEIYNPVVAKSVRQAIKIVNAAIKEYGDFDNIVIEM
ARENQTTQKGQKNSRERMKRIEEGIKELGSQILKEHPVENTQLQNEKLYLYYLQNGRD
MYVDQELDINRLSDYDVDHIVPQSFLKDDSIDNKVLTRSDKNRGKSDNVPSEEVVKKM
KNYWRQLLNAKLITQRKFDNLTKAERGGLSELDKAGFIKRQLVETRQITKHVAQILDSR
MNTKYDENDKLIREVKVITLKSKLVSDFRKDFQFYKVREINYHHAHDAYLNAVVGTA
LIKKYPKLESEFVYGYKVYDVRKMIAKSEQEGKATAKYFFYSNIMNFFKTEITLANGE
IRKRPLIETNGETGEIVWDKGRDFATVRKVLSMPQVNIVKKTEVQTGGFSKESILPKRNS
DKLIARKKDWDPKKYGGFDSPTVAYSVLVVAKVEKGKSKKLKSVKELLGITIMERSSFE
KNPIDFLEAKGYKEVKKDLIIKLPKYSLFELENGRKRMLASAGELQKGNELALPSKYVN
```

-continued

FLYLASHYEKLKGSPEDNEQKQLFVEQHKHYLDEIIEQISEFSKRVILADANLDKVLSAY

NKHRDKPIREQAENIIHLFTLTNLGAPAAFKYFDTTIDRKRYTSTKEVLDATLHQSITGL

YETRIDLSQLGGD (SEQ ID NO: 34)
>Sp(N)St1(C)Cas9
MDKKYSIGLDIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERHPIF

GNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFG

NLIALSLGLTFPNFKSNFDLAEDAKLQLSKDTYDDDLDNLLAQIGDQYADLFLAAKNLSD

AILLSDILRVNTEITKAPLSASMIKRYDEHHQLTLLKALVRQQLPEKYKEIFFDQSKNGY

AGYIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARETNEDDEKKAI

QKIQKANKDEKDAAMLKAANQYNGKAELPHSVFHGHKQLATKIRLWHQQGERC

LYTGKTISIHDLINNSNQFEVDHILPLSFITDDSLANKYLVYATANQEKGQRTPYQAL

DSMDDAWSFRELKAFVRESKTLSNKKKEYLLTEEDISKFDVRKKFIERNLVDTRYA

SRVVLNALQEHFRAHKIDTKVSVVRGQFTSQLRRHWGIEKTRDTYHHHAVDALIIA

ASSQLNLWKKQKNTLVSYSEDQLLDIETGELISDDEYKESVFKAPYQHFVDTLKSK

EFEDSILFSYQVDSKFNRKISDATIYATRQAKVGKDKADETYVLGKIKDIYTQDGYD

AFMKIYKKDKSKFLMYRHDPQTFEKVIEPILENYPNKQINEKGKEVPCNPFLKYKE

EHGYIRKYSKKGNGPEIKSLKYYDSKLGNHIDITPKDSNNKVVLQSVSPWRADVYF

NKTTGKYEILGLKYADLQFEKGTGTYKISQEKYNDIKKKEGVDSDSEFKFTLYKND

LLLVKDTETKEQQLFRFLSRTMPKQKHYVELKPYDKQKFEGGEALIKVLGNVANS

GQCKKGLGKSNISIYKVRTDVLGNQHIIKNEGDKPKLDF

The benefit of making chimeric Cas9 include:
a. reduce toxicity
b. improve expression in eukaryotic cells
c. enhance specificity
d. reduce molecular weight of protein, make protein smaller by combining the smallest domains from different Cas9 homologs.
e. Altering the PAM sequence requirement Example 3

Utilization of Cas9 as a Generic DNA Binding Protein

Figure 5:
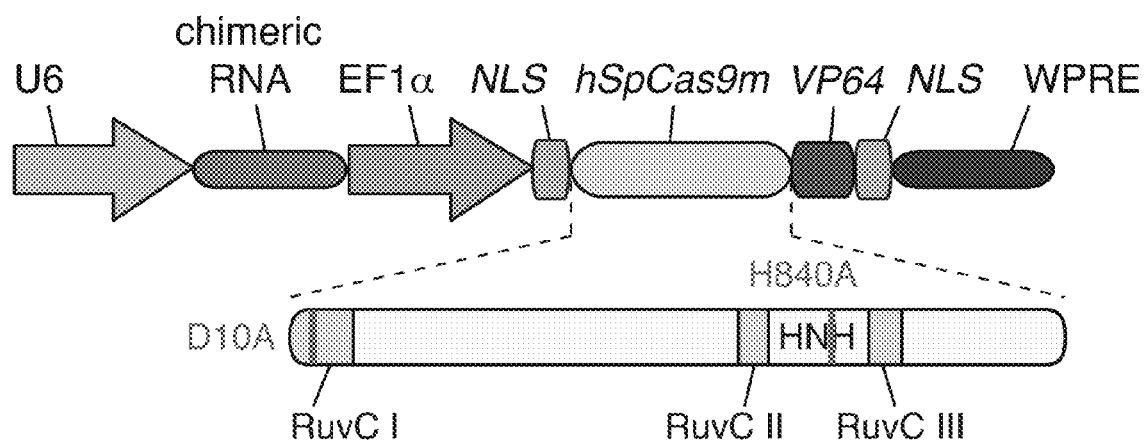
FIG. 5 shows a schematic construct in which the transcriptional activation domain (VP64) is fused to Cas9 with two mutations in the catalytic domains (D10 and H840).
Figure 8:
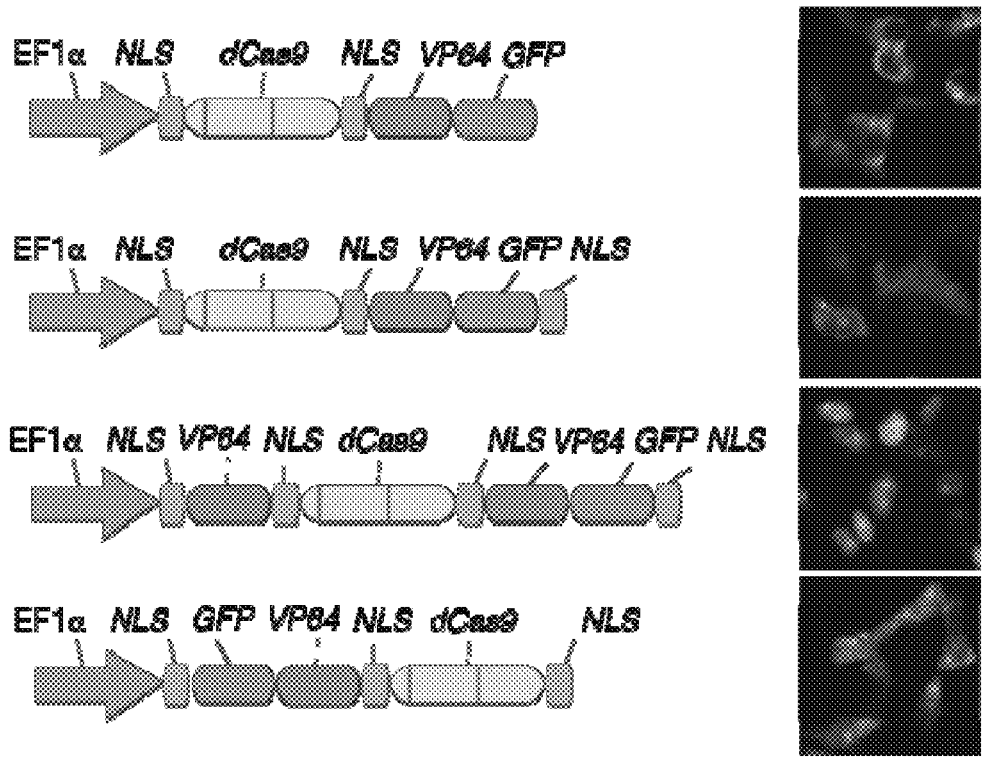
FIG. 8 shows the localization of Cas9-VP64-GFP constructs into 293 cells as assessed by a fluorescent microscope 12 hours post transfection.

Applicants used Cas9 as a generic DNA binding protein by mutating the two catalytic domains (D10 and H840) responsible for cleaving both strands of the DNA target. In order to upregulate gene transcription at a target locus Applicants fused the transcriptional activation domain (VP64) to Cas9 (FIG. 5). Applicants hypothesized that it would be important to see strong nuclear localization of the Cas9-VP64 fusion protein because transcription factor activation strength is a function of time spent at the target. Therefore, Applicants cloned a set of Cas9-VP64-GFP constructs, transfected them into 293 cells and assessed their localization under a fluorescent microscope 12 hours post-transfection (FIG. 8).

Figure 6:
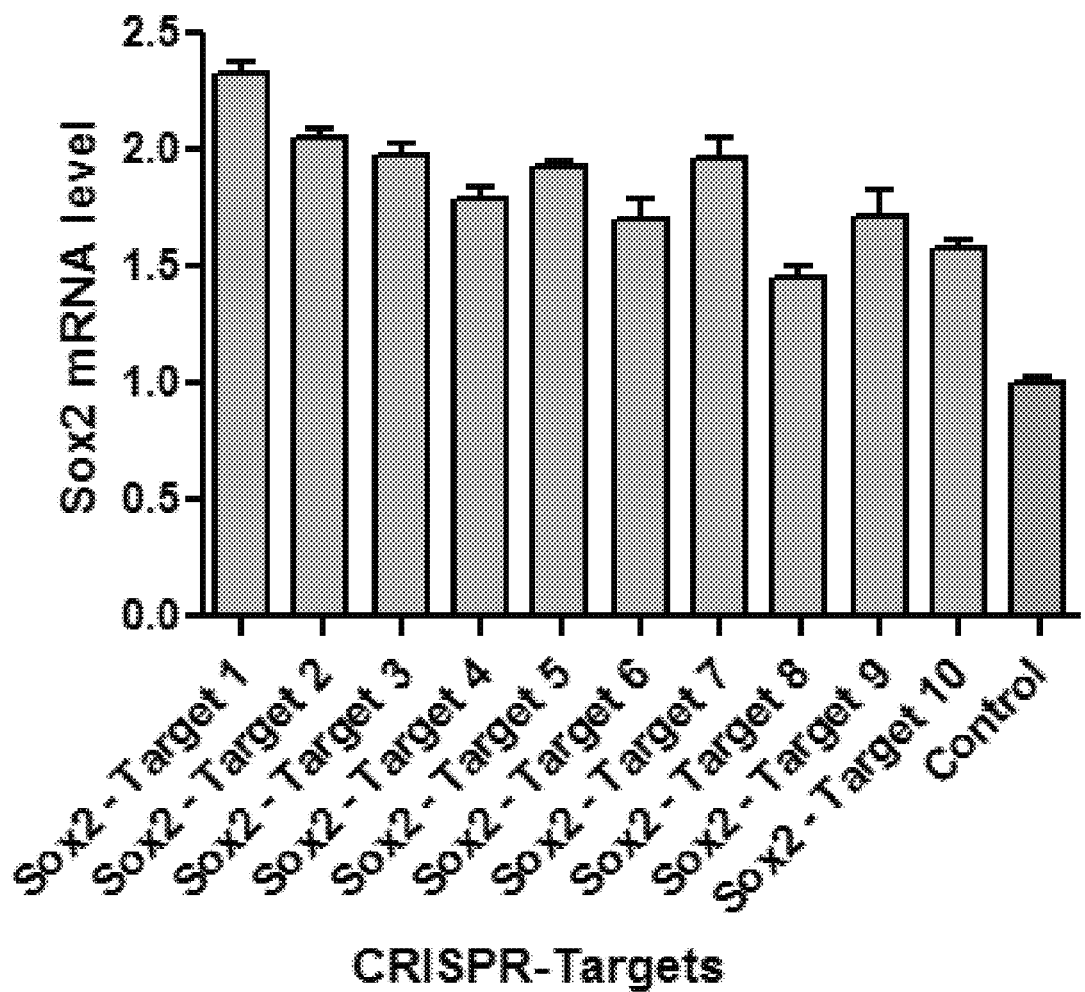
FIG. 6 shows a graphical representation of transcriptional activation following cotransfection of the Cas9-VP64 with PCR generated chimeric crispr RNA (chiRNA) in 293 cells. Assessment was carried out 72 hours after transfection using RT-qPCR.
Figure 12:
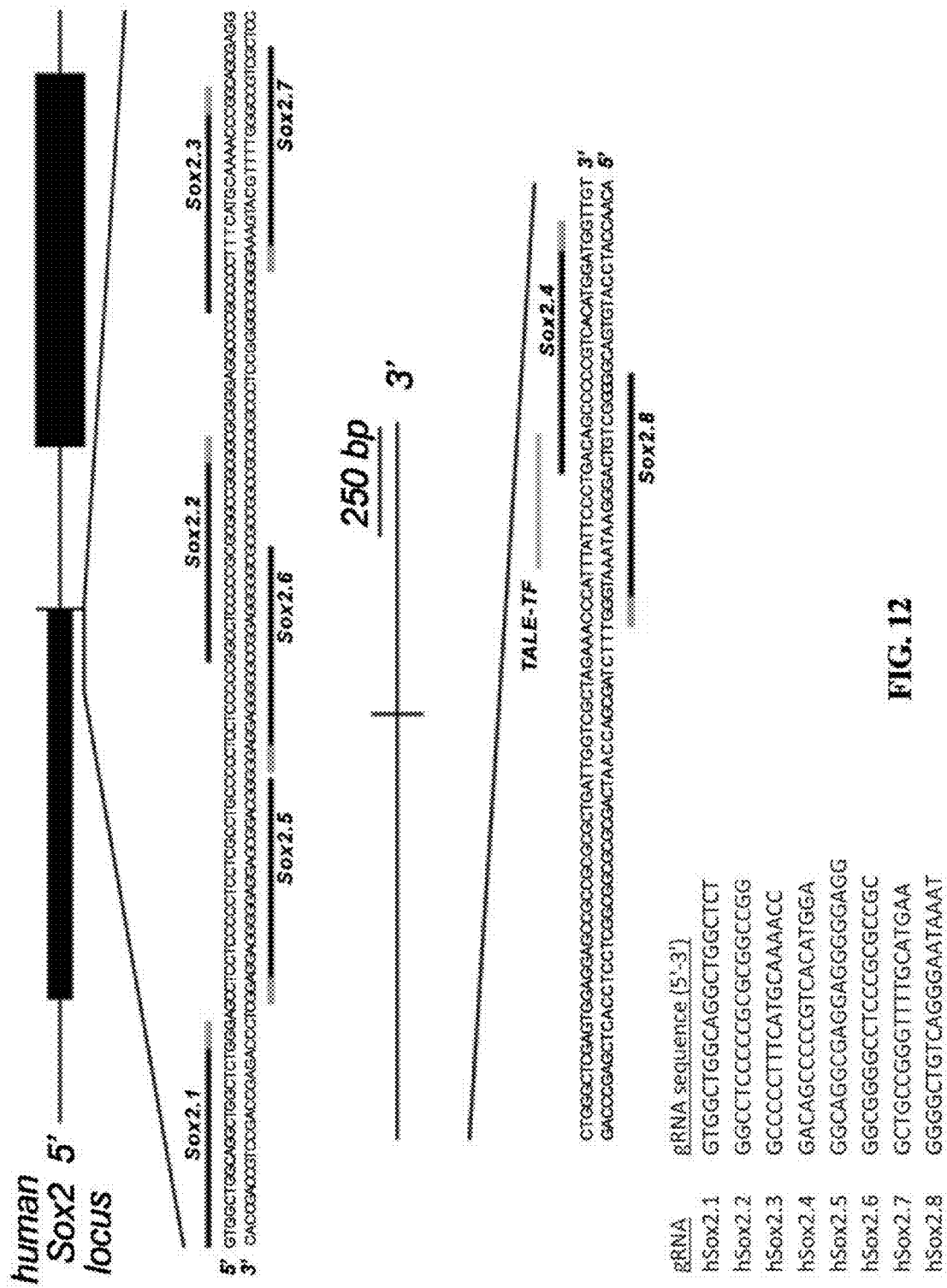
FIG. 12 shows the positioning of target sites in the human Sox2 locus with each target being 20 bp long with a neighboring NGG protspacer adjacent motif (PAM).

The same constructs were cloned as a 2A-GFP rather than a direct fusion in order to functionally test the constructs without a bulky GFP present to interfere. Applicants elected to target the Sox2 locus with the Cas9 transactivator because it could be useful for cellular reprogram and the locus has already been validated as a target for TALE-TF mediated transcriptional activation. For the Sox2 locus Applicants chose eight targets near the transcriptional start site (TSS). Each target was 20 bp long with a neighboring NGG protspacer adjacent motif (PAM) (FIG. 12). Each Cas9-VP64 construct was co-transfected with each PCR generated chimeric crispr RNA (chiRNA) in 293 cells. 72 hours post transfection the transcriptional activation was assessed using RT-qPCR (FIG. 6).

To further optimize the transcriptional activator, Applicants titrated the ratio of chiRNA (Sox2.1 and Sox2.5) to Cas9 (NLS-VP64-NLS-hSpCas9-NLS-VP64-NLS), transfected into 293 cells, and quantified using RT-qPCR (FIG. 11). These results indicate that Cas9 can be used as a generic DNA binding domain to upregulate gene transcription at a target locus.

Applicants designed a second generation of constructs. (Table 1 below).

--- pLenti-EF1a-GFP-2A-6xHis-NLS-VP64-NLS-hSpCsn1(D10A, H840A)-NLS ("6xHis" disclosed as SEQ ID NO: 1)
pLenti-EF1a-GFP-2A-6xHis-NLS-VP64-NLS-hSpCsn1(D10A, H840A) ("6xHis" disclosed as SEQ ID NO: 1)
pLenti-EF1a-GFP-2A-6xHis-NLS-VP64-NLS-NLS-hSpCsn1(D10A, H840A) ("6xHis" disclosed as SEQ ID NO: 1)
pLenti-EF1a-GFP-2A-6xHis-NLS-hSpCsn1(D10A, H840A)-NLS ("6xHis" disclosed as SEQ ID NO: 1)
pLenti-EF1a-GFP-2A-6xHis-NLS-hSpCsn1(D10A, H840A) ("6xHis" disclosed as SEQ ID NO: 1)
pLenti-EF1a-GFP-2A-6xHis-NLS-NLS-hSpCsn1(D10A, H840A) ("6xHis" disclosed as SEQ ID NO: 1)

---

Applicants use these constructs to assess transcriptional activation (VP64 fused constructs) and repression (Cas9 only) by RT-qPCR. Applicants assess the cellular localization of each construct using anti-His antibody, nuclease activity using a Surveyor nuclease assay, and DNA binding affinity using a gel shift assay. In a preferred embodiment of the invention, the gel shift assay is an EMSA gel shift assay.

Example 4

Cas9 Repressor

It has been shown previously that dCas9 can be used as a generic DNA binding domain to repress gene expression. Applicants report an improved dCas9 design as well as dCas9 fusions to the repressor domains KRAB and SID4x. From the plasmid library created for modulating transcription using Cas9 in Table 2 below, and FIG. 15, the following repressor plasmids were functionally characterized by qPCR: pXRP27, pXRP28, pXRP29, pXRP48, pXRP49, pXRP50, pXRP51, pXRP52, pXRP53, pXRP56, pXRP58, pXRP59, pXRP61, and pXRP62.

Figure 16:
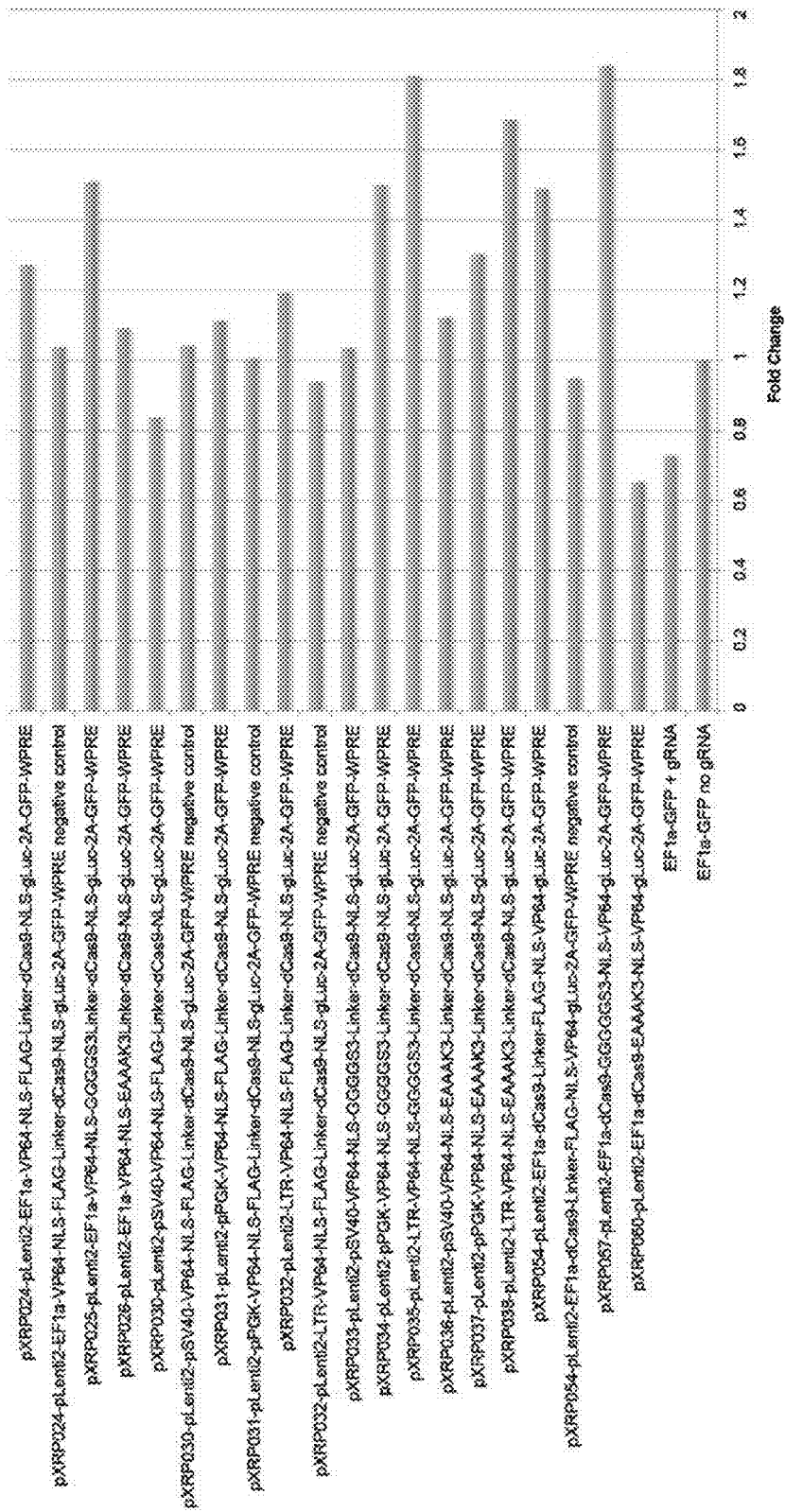
FIG. 16 shows co-transfecting of each dCas9 repressor plasmid with two guide RNAs targeted to the coding strand of the beta-catenin gene. RNA was isolated 72 hours after transfection and gene expression was quantified by RT-qPCR. The endogenous control gene was GAPDH. Two validated shRNAs were used as positive controls. Negative controls were certain plasmids transfected without gRNA, these are denoted as "pXRP## control".
Figure 19:
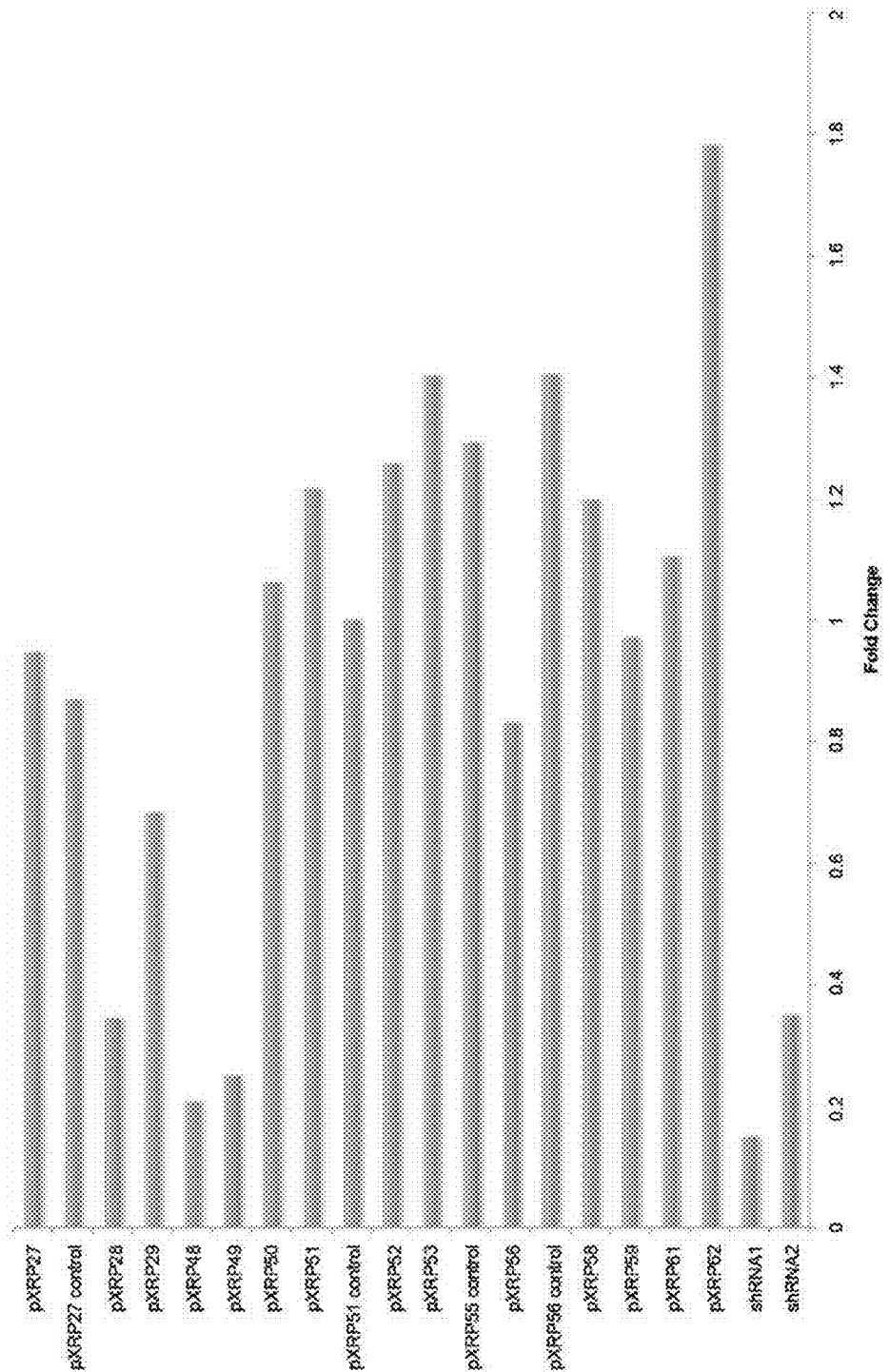
FIG. 19 shows gene expression of beta-catenin in HEK 293FT cells 72 hours after transfection. Cas9 repressor constructs were targeted to the beta-catenin locus and compared to the gold standard shRNAs. Similar repression could be seen with Cas9 repressors and the shRNA.

Each dCas9 repressor plasmid was co-transfected with two guide RNAs targeted to the coding strand of the beta-catenin gene (gRNAs were designed by my collaborator at the Broad, Joseph Rosenbluh). RNA was isolated 72 hours after transfection and gene expression was quantified by RT-qPCR (FIG. 16). The endogenous control gene was GAPDH. Two validated shRNAs were used as positive controls. Negative controls were certain plasmids transfected without gRNA, these are denoted as "pXRP## control" in FIG. 16. The plasmids pXRP28, pXRP29, pXRP48, and pXRP49 could repress the beta-catenin gene when using the specified targeting strategy. These plasmids correspond to dCas9 without a functional domain (pXRP28 and pXRP28) and dCas9 fused to SID4x (pXRP48 and pXRP49).

TABLE 2

(TABLE 2 discloses "GGGGS$_3$" as SEQ ID NO: 35, "EAAAK$_3$" as SEQ ID NO: 36 and "GGGGGS$_3$" as SEQ ID NO: 37)

pXRP024-pLenti2-EF1a-VP64-NLS-FLAG-Linker-dCas9-NLS-gLuc-2A-GFP-WPRE
pXRP025-pLenti2-EF1a-VP64-NLS-GGGGS$_3$Linker-dCas9-NLS-gLuc-2A-GFP-WPRE
pXRP026-pLenti2-EF1a-VP64-NLS-EAAAK$_3$Linker-dCas9-NLS-gLuc-2A-GFP-WPRE
pXRP027-pLenti2-EF1a-NLS-FLAG-Linker-dCas9-NLS-gLuc-2A-GFP-WPRE
pXRP028-pLenti2-EF1a-NLS-GGGGS$_3$Linker-dCas9-NLS-gLuc-2A-GFP-WPRE
pXRP029-pLenti2-EF1a-NLS-EAAAK$_3$Linker-dCas9-NLS-gLuc-2A-GFP-WPRE
pXRP030-pLenti2-pSV40-VP64-NLS-FLAG-Linker-dCas9-NLS-gLuc-2A-GFP-WPRE
pXRP031-pLenti2-pPGK-VP64-NLS-FLAG-Linker-dCas9-NLS-gLuc-2A-GFP-WPRE
pXRP032-pLenti2-LTR-VP64-NLS-FLAG-Linker-dCas9-NLS-gLuc-2A-GFP-WPRE
pXRP033-pLenti2-pSV40-VP64-NLS-GGGGS$_3$Linker-dCas9-NLS-gLuc-2A-GFP-WPRE
pXRP034-pLenti2-pPGK-VP64-NLS-GGGGS$_3$Linker-dCas9-NLS-gLuc-2A-GFP-WPRE
pXRP035-pLenti2-LTR-VP64-NLS-GGGGS$_3$Linker-dCas9-NLS-gLuc-2A-GFP-WPRE
pXRP036-pLenti2-pSV40-VP64-NLS-EAAAK$_3$Linker-dCas9-NLS-gLuc-2A-GFP-WPRE
pXRP037-pLenti2-pPGK-VP64-NLS-EAAAK$_3$Linker-dCas9-NLS-gLuc-2A-GFP-WPRE
pXRP038-pLenti2-LTR-VP64-NLS-EAAAK$_3$Linker-dCas9-NLS-gLuc-2A-GFP-WPRE
pXRP048-pLenti2-EF1a-SID4x-NLS-FLAG-Linker-dCas9-NLS-gLuc-2A-GFP-WPRE
pXRP049-pLenti2-EF1a-SID4X-NLS-GGGGS$_3$Linker-dCas9-NLS-gLuc-2A-GFP-WPRE
pXRP050-pLenti2-EF1a-SID4X-NLS-EAAAK$_3$Linker-dCas9-NLS-gLuc-2A-GFP-WPRE
pXRP051-pLenti2-EF1a-KRAB-NLS-FLAG-Linker-dCas9-NLS-gLuc-2A-GFP-WPRE
pXRP052-pLenti2-EF1a-KRAB-NLS-GGGGS$_3$Linker-dCas9-NLS-gLuc-2A-GFP-WPRE
pXRP053-pLenti2-EF1a-KRAB-NLS-EAAAK$_3$Linker-dCas9-NLS-gLuc-2A-GFP-WPRE
pXRP054-pLenti2-EF1a-dCas9-Linker-FLAG-NLS-VP64-gLuc-2A-GFP-WPRE
pXRP055-pLenti2-EF1a-dCas9-Linker-FLAG-NLS-SID4X-gLuc-2A-GFP-WPRE
pXRP056-pLenti2-EF1a-dCas9-Linker-FLAG-NLS-KRAB-gLuc-2A-GFP-WPRE
pXRP057-pLenti2-EF1a-dCas9-GGGGGS$_3$-NLS-VP64-gLuc-2A-GFP-WPRE
pXRP058-pLenti2-EF1a-dCas9-GGGGGS$_3$-NLS-SID4X-gLuc-2A-GFP-WPRE
pXRP059-pLenti2-EF1a-dCas9-GGGGGS$_3$-NLS-KRAB-gLuc-2A-GFP-WPRE
pXRP060-pLenti2-EF1a-dCas9-EAAAK$_3$-NLS-VP64-gLuc-2A-GFP-WPRE
pXRP061-pLenti2-EF1a-dCas9-EAAAK$_3$-NLS-SID4X-gLuc-2A-GFP-WPRE
pXRP062-pLenti2-EF1a-dCas9-EAAAK$_3$-NLS-KRAB-gLuc-2A-GFP-WPRE
pXRP024-pLenti2-EF1a-VP64-NLS-FLAG-Linker-Cas9-NLS-gLuc-2A-GFP-WPRE
pXRP025-pLenti2-EF1a-VP64-NLS-GGGGS$_3$Linker-Cas9-NLS-gLuc-2A-GFP-WPRE
pXRP026-pLenti2-EF1a-VP64-NLS-EAAAK$_3$Linker-Cas9-NLS-gLuc-2A-GFP-WPRE
pXRP027-pLenti2-EF1a-NLS-FLAG-Linker-Cas9-NLS-gLuc-2A-GFP-WPRE
pXRP028-pLenti2-EF1a-NLS-GGGGS$_3$Linker-Cas9-NLS-gLuc-2A-GFP-WPRE
pXRP029-pLenti2-EF1a-NLS-EAAAK$_3$Linker-Cas9-NLS-gLuc-2A-GFP-WPRE
pXRP030-pLenti2-pSV40-VP64-NLS-FLAG-Linker-Cas9-NLS-gLuc-2A-GFP-WPRE
pXRP031-pLenti2-pPGK-VP64-NLS-FLAG-Linker-Cas9-NLS-gLuc-2A-GFP-WPRE
pXRP032-pLenti2-LTR-VP64-NLS-FLAG-Linker-Cas9-NLS-gLuc-2A-GFP-WPRE
pXRP033-pLenti2-pSV40-VP64-NLS-GGGGS$_3$Linker-Cas9-NLS-gLuc-2A-GFP-WPRE

TABLE 2-continued (TABLE 2 discloses "GGGGS₃" as SEQ ID NO: 35, "EAAAK₃" as SEQ ID NO: 36 and "GGGGGS₃" as SEQ ID NO: 37)

```
pXRP034-pLenti2-pPGK-VP64-NLS-GGGGS3Linker-Cas9-NLS-gLuc-2A-GFP-WPRE
pXRP035-pLenti2-LTR-VP64-NLS-GGGGS3Linker-Cas9-NLS-gLuc-2A-GFP-WPRE
pXRP036-pLenti2-pSV40-VP64-NLS-EAAAK3Linker-Cas9-NLS-gLuc-2A-GFP-WPRE
pXRP037-pLenti2-pPGK-VP64-NLS-EAAAK3Linker-Cas9-NLS-gLuc-2A-GFP-WPRE
pXRP038-pLenti2-LTR-VP64-NLS-EAAAK3Linker-Cas9-NLS-gLuc-2A-GFP-WPRE
pXRP048-pLenti2-EF1a-SID4x-NLS-FLAG-Linker-Cas9-NLS-gLuc-2A-GFP-WPRE
pXRP049-pLenti2-EF1a-SID4X-NLS-GGGGS3Linker-Cas9-NLS-gLuc-2A-GFP-WPRE
pXRP050-pLenti2-EF1a-SID4X-NLS-EAAAK3Linker-Cas9-NLS-gLuc-2A-GFP-WPRE
pXRP051-pLenti2-EF1a-KRAB-NLS-FLAG-Linker-Cas9-NLS-gLuc-2A-GFP-WPRE
pXRP052-pLenti2-EF1a-KRAB-NLS-GGGGS3Linker-Cas9-NLS-gLuc-2A-GFP-WPRE
pXRP053-pLenti2-EF1a-KRAB-NLS-EAAAK3Linker-Cas9-NLS-gLuc-2A-GFP-WPRE
pXRP054-pLenti2-EF1a-Cas9-Linker-FLAG-NLS-VP64-gLuc-2A-GFP-WPRE
pXRP055-pLenti2-EF1a-Cas9-Linker-FLAG-NLS-SID4X-gLuc-2A-GFP-WPRE
pXRP056-pLenti2-EF1a-Cas9-Linker-FLAG-NLS-KRAB-gLuc-2A-GFP-WPRE
pXRP057-pLenti2-EF1a-Cas9-GGGGGS3-NLS-VP64-gLuc-2A-GFP-WPRE
pXRP058-pLenti2-EF1a-Cas9-GGGGGS3-NLS-SID4X-gLuc-2A-GFP-WPRE
pXRP059-pLenti2-EF1a-Cas9-GGGGGS3-NLS-KRAB-gLuc-2A-GFP-WPRE
pXRP060-pLenti2-EF1a-Cas9-EAAAK3-NLS-VP64-gLuc-2A-GFP-WPRE
pXRP061-pLenti2-EF1a-Cas9-EAAAK3-NLS-SID4X-gLuc-2A-GFP-WPRE
pXRP062-pLenti2-EF1a-Cas9-EAAAK3-NLS-KRAB-gLuc-2A-GFP-WPRE
```

Example 5

Cas9 Transcriptional Modulator and Nuclear Localization

Figure 7:
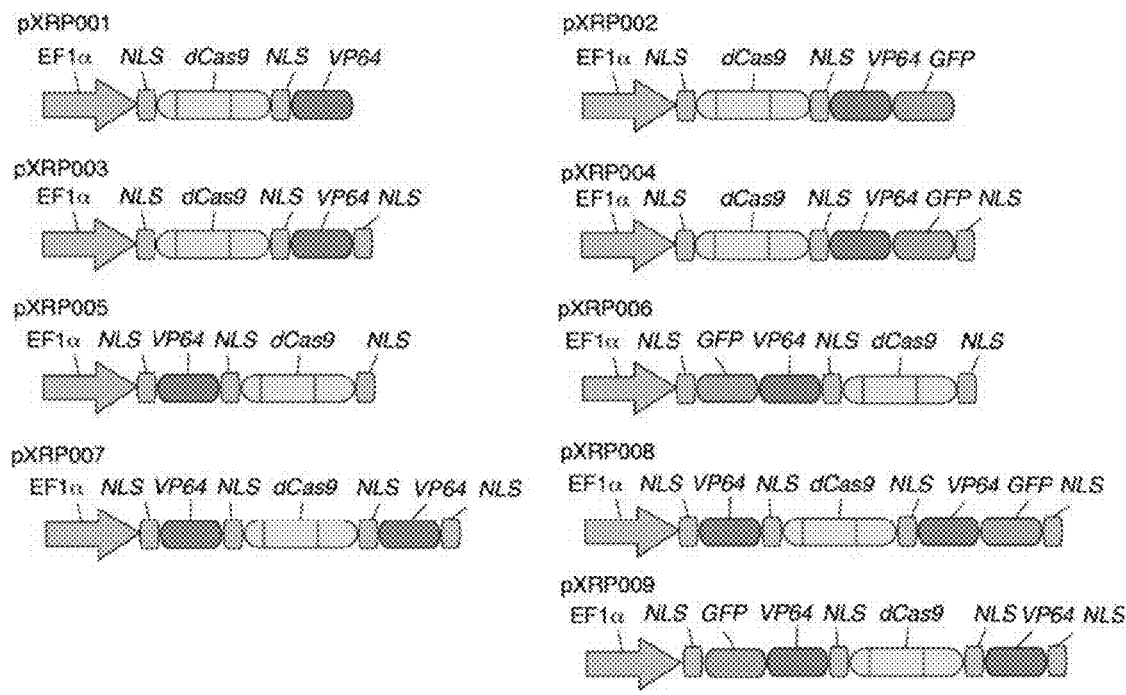
FIG. 7 shows a number of vectors incorporating mutant Cas9 genes with VP64, NLS, and GFP markers.

Cas9 Transcriptional Modulator. Applicants set out to turn the Cas9/gRNA CRISPR system into a generalized DNA binding system in which Applicants can execute functions beyond DNA cleavage. Whereby, fusing functional domains onto a catalytically inactive Cas9, dCas9, Applicants can impart novel functions, such as transcriptional activation/repression, methylation/demethylation, or chromatin modifications. To accomplish this goal Applicants made a catalytically inactive Cas9 mutant by changing two residues essential for nuclease activity, D10 and H840, to alanine. It has been shown previously that by mutating these two residues the nuclease activity of Cas9 is abolished while maintaining the ability to bind target DNA. The functional domains Applicants decided to focus on to test Applicants' hypothesis are the transcriptional activator VP64 and the transcriptional repressors SID and KRAB.

dCas9 Nuclear localization. Applicants hypothesized that the most effective dCas9 transcriptional modulator would be strongly localized to the nucleus where it would have its greatest influence on transcription. Moreover, any residual dCas9 in the cytoplasm could have unwanted effects. In previous work Applicants determined that wild-type Cas9 does not localize into the nucleus without including multiple nuclear localization signals (NLSs). Because multiple NLS sequences were required Applicants reasoned that it is difficult to get Cas9 into the nucleus and any additional domain that is fused to Cas9 could disrupt the nuclear localization. Therefore, Applicants built five dCas9-VP64-GFP fusion constructs to optimize the position and number of NLS sequences. A second version of each construct was made for functional testing, and these constructs were not directly fused to GFP. A schematic of these designs is shown in FIG. 7. These constructs were cloned into a plenti2 backbone under the expression of the human EF1α promoter. The WPRE element was also added for more robust protein expression. Each construct was transfected into HEK 293FT cells using Lipofectame 2000 and imaged 24 hours post-transfection (FIG. 8). FIG. 8 shows that the best nuclear localization is obtained when the fusion proteins have NLS sequences on both the N- and C-term of the fusion protein. The highest observed nuclear localization occurred in the construct with four NLS elements.

Figure 9:
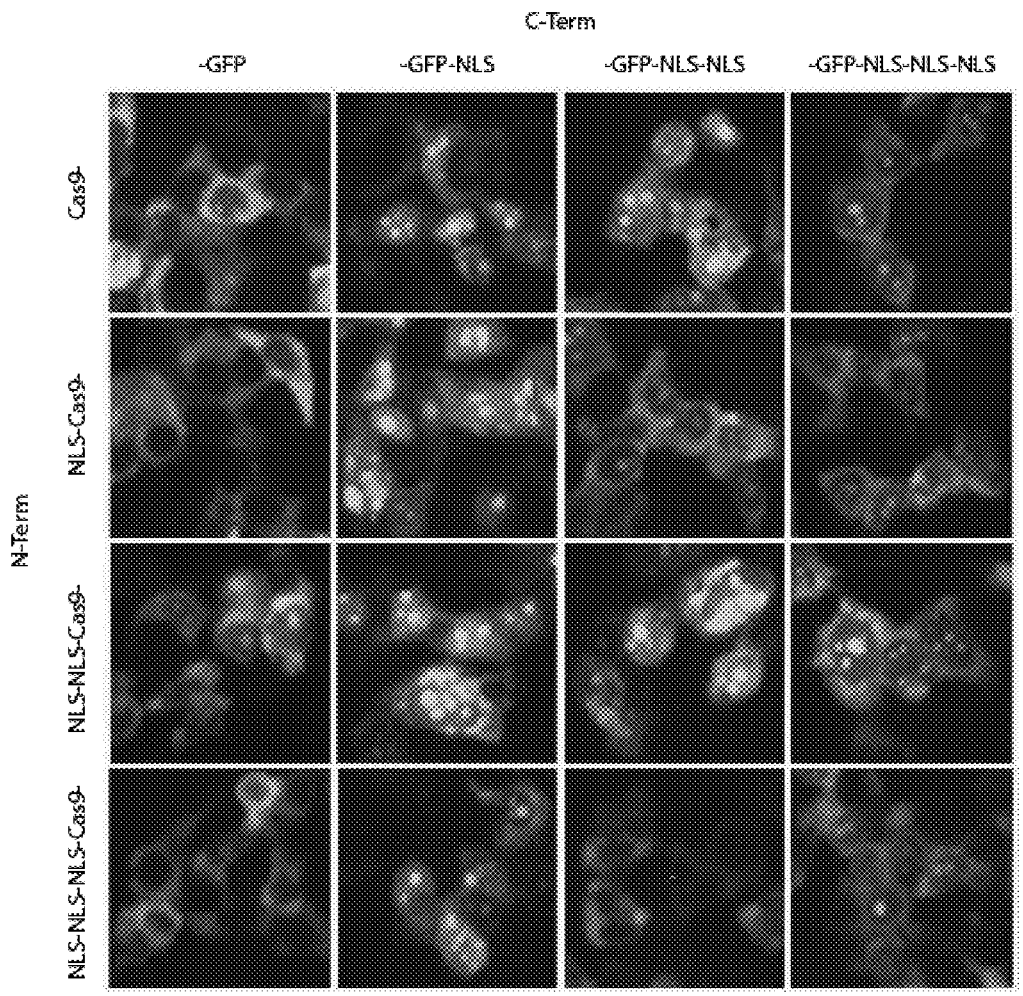
FIG. 9 shows the localization of 16 dCas9-GFP fusions with the same alpha importin NLS sequence (SEQ ID NO: 87) on either the N- or C-term looking at zero to three tandem repeats. Each construct was transfected into HEK 293FT cells using Lipofectame 2000 and imaged 24 hours post-transfection

To more robustly understand the influence of NLS elements on dCas9 Applicants made 16 dCas9-GFP fusions by adding the same alpha importin NLS sequence on either the N- or C-term looking at zero to three tandem repeats. The same cloning strategy was used as explained previously. Each construct was transfected into HEK 293FT cells using Lipofectame 2000 and imaged 24 hours post-transfection (FIG. 9). Notably, the number of NLS elements does not directly correlate with the extent of nuclear localization. Adding an NLS on the C-term has a greater influence on nuclear localization than adding on the N-term. For future applications it is more favorable to have smaller proteins. Therefore, the optimal NLS architecture for dCas9 was having one NLS on the N-term and C-term (pXRPNLS006).

Figure 10:
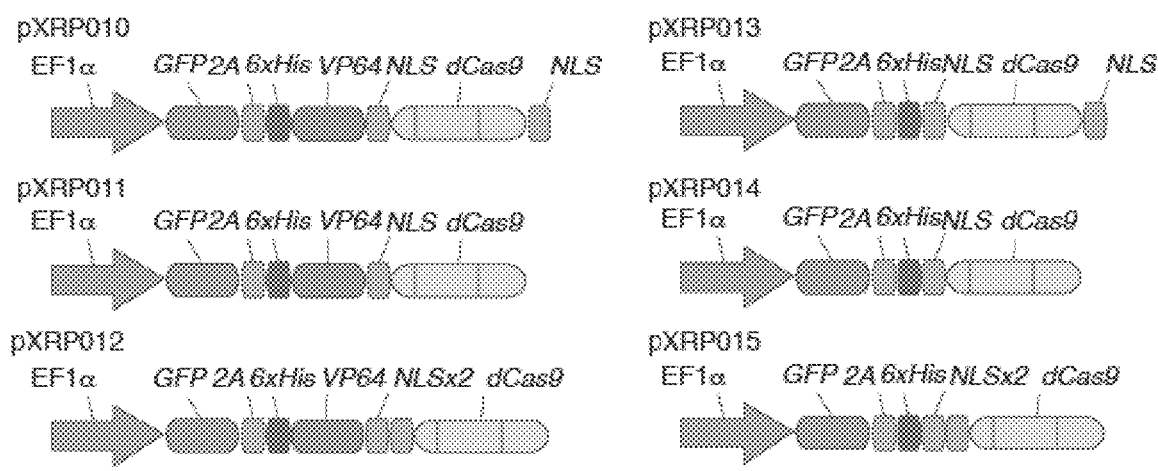
FIG. 10 shows six versions of a 6×His tag (SEQ ID NO: 1) added to dCas9, transfected into 293FT cells, and stained with an anti-6×His antibody ("6×His" disclosed as SEQ ID NO: 1). Three were constructed for transcriptional activation (VP64 fusions), and the other three were for transcriptional repression (no functional domain).

One potential confounding factor of using a GFP fusion to determine nuclear localization is that the GFP itself could have a large influence on where the protein localizes in the cell. Therefore, Applicants determined that a good approach would be to include a 6×His tag (SEQ ID NO: 1) to dCas9, transfect into 293FT cells, and then stain with an anti-6×His antibody ("6×His" disclosed as SEQ ID NO: 1). Applicants made six versions utilizing this idea (FIG. 10). Three were constructed for transcriptional activation (VP64 fusions), and the other three were for transcriptional repression (no functional domain). These constructs were also made so Applicants could purify the recombinant protein using a nickel column. There are many applications of the 6×His-dCas9 constructs ("6×His" disclosed as SEQ ID NO: 1), such as, to perform an electromobility gel shift assay to show that mutated Cas9 can indeed bind its DNA target. The repression constructs (pXRP013, pXRP014, pXRP015) were transfected in HEK 293 FT cells and were immunostained and imaged after 24 hours (FIG. 11). Under this specific context, dCas9 requires two NLS signals on the N-term to be localized into the nucleus. Interestingly, one NLS on each terminus did not cause dCas9 to be strongly nuclear localized. Taken together, what this data suggests is that there is no generalized rule that can be made to conclusively say that a dCas9 fusion protein will be localized into the nucleus. The construct of interest must be validated in the system it will be used to determine if it is in fact localized to the nucleus.

Cas9 Transcriptional Modulator Functional Testing. Applicants functionally tested the dCas9-VP64 protein by targeting the Sox2 locus and quantifying transcriptional activation by RT-qPCR. Eight DNA target sites were chosen to span the promoter of Sox2 (FIG. 12). The gRNA expression cassettes were cloned into a pAAV-U6-gRNA/trcrRNA backbone plasmid, pA6. The plasmid utilizes the type IIs enzyme Bbsi to reveals sticky ends for annealed oligo ligation. So for each target all one needs is two complimentary oligos with the appropriate sticky ends.

Figure 13:
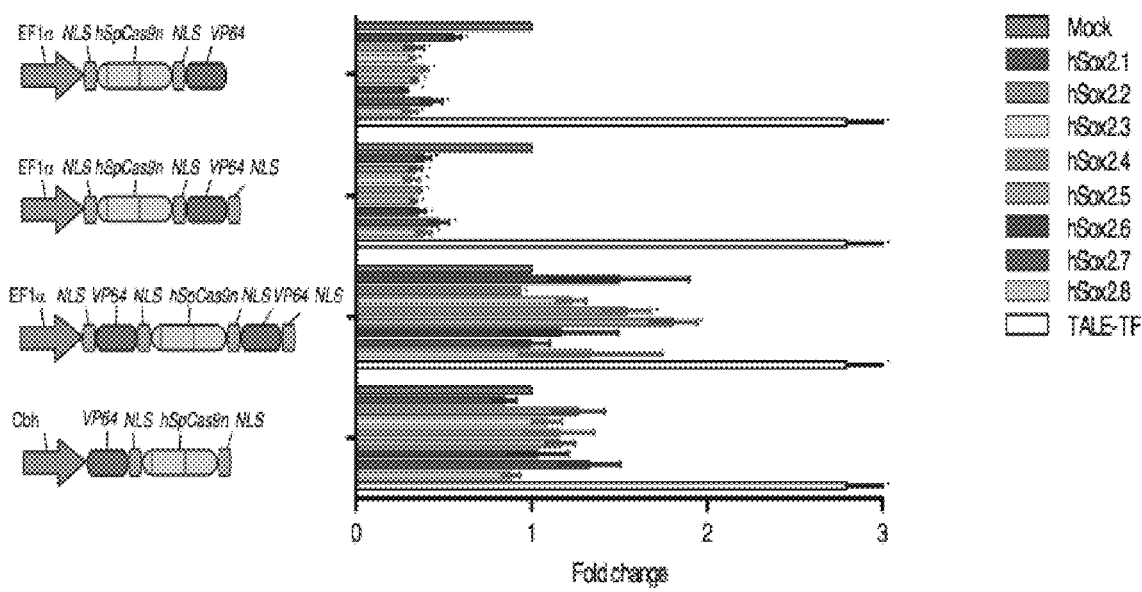
FIG. 13 shows co-transfecting of each dCas9 containing construct with pA6 plasmids into HEK 293FT cells using Lipofectame 2000. 72 hours post-transfection total RNA was extracted from the cells. 1 ug of RNA was reverse transcribed into cDNA (qScript Supermix) in a 40 ul reaction. 2 ul of reaction product was added into a single 20 ul TaqMan assay qPCR reaction. Each experiment was performed in biological and technical triplicates. No RT control and no template control reactions showed no amplification.
Figure 14:
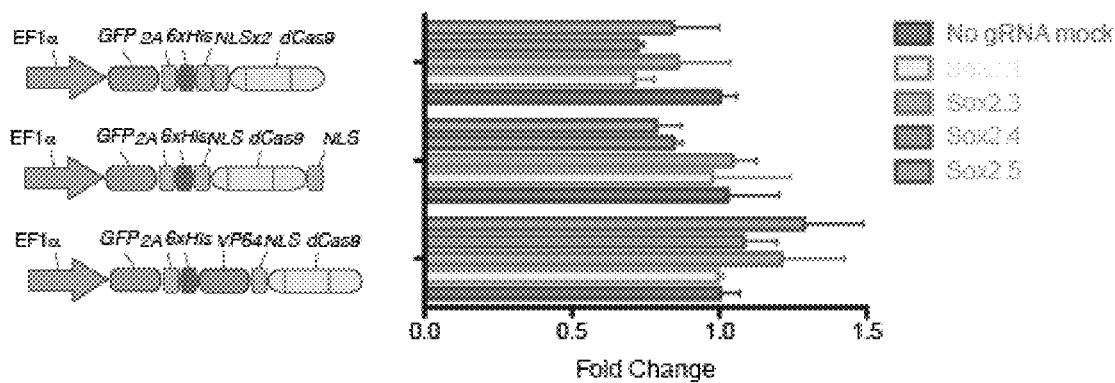
FIG. 14 shows testing of constructs (pXRP011, pXRP013, pXRP015) using the same Sox2 targets as FIG. 13.

Each dCas9 containing construct was co-transfected with pA6 plasmids into HEK 293FT cells using Lipofectame 2000. 72 hours post-transfection total RNA was extracted from the cells. 1 ug of RNA was reverse transcribed into cDNA (qScript Supermix) in a 40 ul reaction. 2 ul of reaction product was added into a single 20 ul TaqMan assay qPCR reaction. Each experiment was performed in biological and technical triplicates. No RT control and no template control reactions showed no amplification. The results of this experiment are shown in FIG. 13. Constructs that do not show strong nuclear localization, pXRP02 and pXRP04, result in no activation. For the construct that did show strong nuclear localization, pXRP08, moderate activation was observed. Statistically significant activation was observed in the case of gRNAs Sox2.4 and Sox2.5. Of the 6×His-dCas9 constructs ("6×His" disclosed as SEQ ID NO: 1) (pXRP011, pXRP013, pXRP015) were also tested using the same Sox2 targets (FIG. 14). Compared to no gRNA mock controls Applicants could repress or activate Sox2.

To further optimize the dCas9 transcriptional activator and repressor Applicants built 31 constructs to explore different linkers, functional domains, and N- and C-term fusions. The list of constructs and the critical elements are shown in FIG. 15. Three linkers were tested and the first was an unusual linker that was published by Shen and collegues (Shen et al. 2013, Cell Research paper from Xingxu Huang's lab: Cell Research 23, 720-723 (May 2013)) where they showed it drastically improved nuclear localization and nuclease activity of Cas9. The second and third linkers were very common linkers known to be flexible (GGGGS3 (SEQ ID NO: 35)) and rigid (EAAAK3 (SEQ ID NO: 36)). The functional domains tested were VP64 for activation and SID4x and KRAB for repression. dCas9 without a functional domain was also made to test repression. The promoters tested were human EF1a, human pPGK, SV40, and the lack of a promoter where expression is driven by the viral LTR.

All transcriptional activator constructs were targeted to the Sox2 locus using a combination of two gRNAs, hSox2.1 and hSox2.4. The dCas9 activator constructs were co-transfected with the gRNAs into HEK 293FT cells and analyzed by qPCR after 72 hours (FIG. 16).

A luciferase Sox2 reporter assay was adopted to simplify the methods associated for determining levels of activation. The assay works by co-transfecting in three plasmids, 1) dCas9, 2) gRNA, 3) Sox2 responsive element driving luciferase. So the level of luciferase is proportional to the amount of Sox2. The Sox2 responsive plasmid was purchased from BioCat. The Sox2 locus was targeted using different combinations of gRNAs and the constructs pXRP024 and pXRP025. A "No dCas9" control was used to determine the basal level of activation. The results shown in the top panel of FIG. 11 suggest that 3-fold activation could be reached compared to "No dCas9" and "No gRNA" controls.

A similar luciferase assay was adopted to test dCas9 transcriptional repression. The candidate gene Applicants chose to repress was beta-catenin and the targets were located near the 5' end of the gene body on the non-coding strand. The first experiment utilizing this assay compared the repressor pXRPNLS006 to the "dCas9" repressor published by Qi and collegues (Qi et al. 2003, Cell paper from Wendell Lim's lab). The luciferase assay results (bottom panel of FIG. 11) show that 3-fold repression can be reached and the pXRPNLS006 plasmid reported here works significantly better than the current standard, "dCas9".

Example 6

Cas9 Transcriptional Activator in Murine and Human Cell Lines

Applicants previously demonstrated the capacity for CRISPR/Cas9 to act as a transcriptional activator. In this example Applicants further test this capability in a murine cell line. Applicants also examined the unguided basal activity of the dCas9-VP64 (double mutant D10A H840A Cas9 fused to the VP64 transcriptional activation domain). Applicants delivered the Cas9 activator system to mouse cells and, separately, characterized the unguided effects of dCas9-VP64 for several human genes.

Mouse Cell Line Experiments: Applicants selected the locus for the mouse gene Neurog2 for testing dCas9-VP64 transcriptional activation in Neuro 2A cells. Applicants also selected 7 sgRNA targeting sequences from a region 300 bp upstream to 100 bp downstream of the annotated Neurog2 transcriptional start site. These guide sequences were cloned by the golden gate method into the px362 plasmid containing the U6 promoter upstream of a chimeric sgRNA cloning backbone.

Neuro 2A cells were cultured in medium consisting of a 1:1 ratio of D5 (100:5:1 DMEM high glucose w/Glutamax and sodium pyruvate: fetal bovine serum: penecillin/stretomycin). For transfection, 120K cells in 0.5 mL culture medium were plated in each well of a 24 well plate. After 22 h in culture, each well of Neuro 2A cells was transfected with 1 ug of DNA using 5 uL of Lipofectamine following the recommended steps of the manufacturer (LIfe Technologies). For all dCas9-VP64+sgRNA samples, 0.5 ug dCas9-VP64 plasmid and 0.5 ug sgRNA expression plasmid were used. For control samples, plasmid masses replaced GFP expressing plasmid as necessary. 4h after transfection, the medium was replaced with 1 mL culture medium. 48h after transfection, RNA was purified using the Macherey Nagel Nucleospin 96 RNA kit. Reverse transcription was performed with qScript cDNA supermix according to the manufacturer's protocol. qPCR was performed using Taqman probes and Taqman Fast Advanced Master Mix from Life Technologies on a Roche LightCycler 480 II real-time PCR machine.

Human Cell Line Experiments: Applicants selected 8 previously available sgRNA sequences for testing in 293FT cells using Applicants' pXRP057 dCas9-VP64 activator construct. Guide sequences were cloned by the golden gate method into the px362 plasmid containing the U6 promoter upstream of a chimeric sgRNA cloning backbone.

293FT cells were cultured in D10 medium (100:10:1 ratio of DMEM high glucose w/Glutamax and sodium pyruvate: fetal bovine serum: 100x HEPES solution). For transfection, 100K cells in 0.5 mL culture medium were plated in each well of a 24 well plate. After 22 h in culture, each well of 293FT cells was transfected with 1 ug of DNA using 5 uL of Lipofectamine following the recommended steps of the manufacturer (LIfe Technologies). For all dCas9-VP64+sgRNA samples, 0.5 ug dCas9-VP64 plasmid and 0.5 ug sgRNA expression plasmid were used. For control samples, including those analyzed for unguided transcriptional effects, plasmid masses were replaced by GFP expressing plasmid as necessary. 4h after transfection, the medium was replaced with 1 mL culture medium. 48h after transfection, RNA was purified using the Macherey Nagel Nucleospin 96 RNA kit. Reverse transcription was performed with qScript cDNA supermix according to the manufacturer's protocol. qPCR was performed using Taqman probes and Taqman Fast Advanced Master Mix from Life Technologies on a Roche LightCycler 480 II real-time PCR machine.

Figure 20:
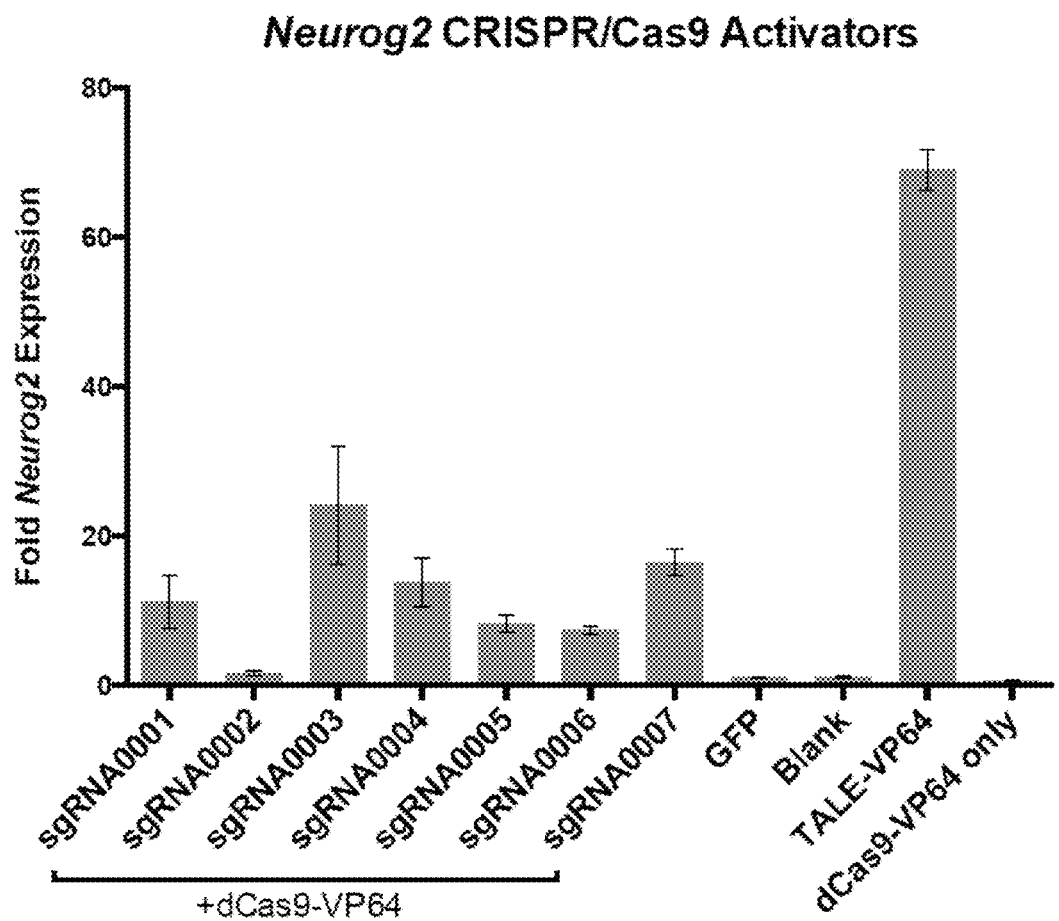
FIG. 20 shows a graphical representation of the fold Neurog2 expression of the 20 bp sgRNA sequences were targeted to the Neurog2 locus in mouse Neuro 2A cells. Neurog2 mRNA levels were measured using RT-qPCR.

Experimental results for Mouse Cell Line Experiments: As shown in FIG. 20, 6 out of 7 sgRNAs targeted to the mouse Neurog2 locus were able to induce upregulation of Neurog2 mRNA as measured by qPCR. With these results, Applicants demonstrated the utility of the Cas9 activator system for gene modulation in a mouse cellular model. The 7 sgRNa sequences are listed below:

| sgRNA | SEQUENCE | SEQ ID NO: |
|---|---|---|
| sgRNA0001 | TGGTTCAGTGGCTGCGTGTC | 38 |
| sgRNA0002 | TGTTTTCTTGGTGGTATATA | 39 |
| sgRNA0003 | ATACGATGAAAAGAATAAGC | 40 |
| sgRNA0004 | GGGGGAGAGGGACTAAAGAA | 41 |
| sgRNA0005 | GGGCGGGGAAGGGTAGGTG | 42 |
| sgRNA0006 | ATTAGATAAAGGGGGACGG | 43 |
| sgRNA0007 | CGGCTTTAACTGGAGTGCCT | 44 |

Figure 21:
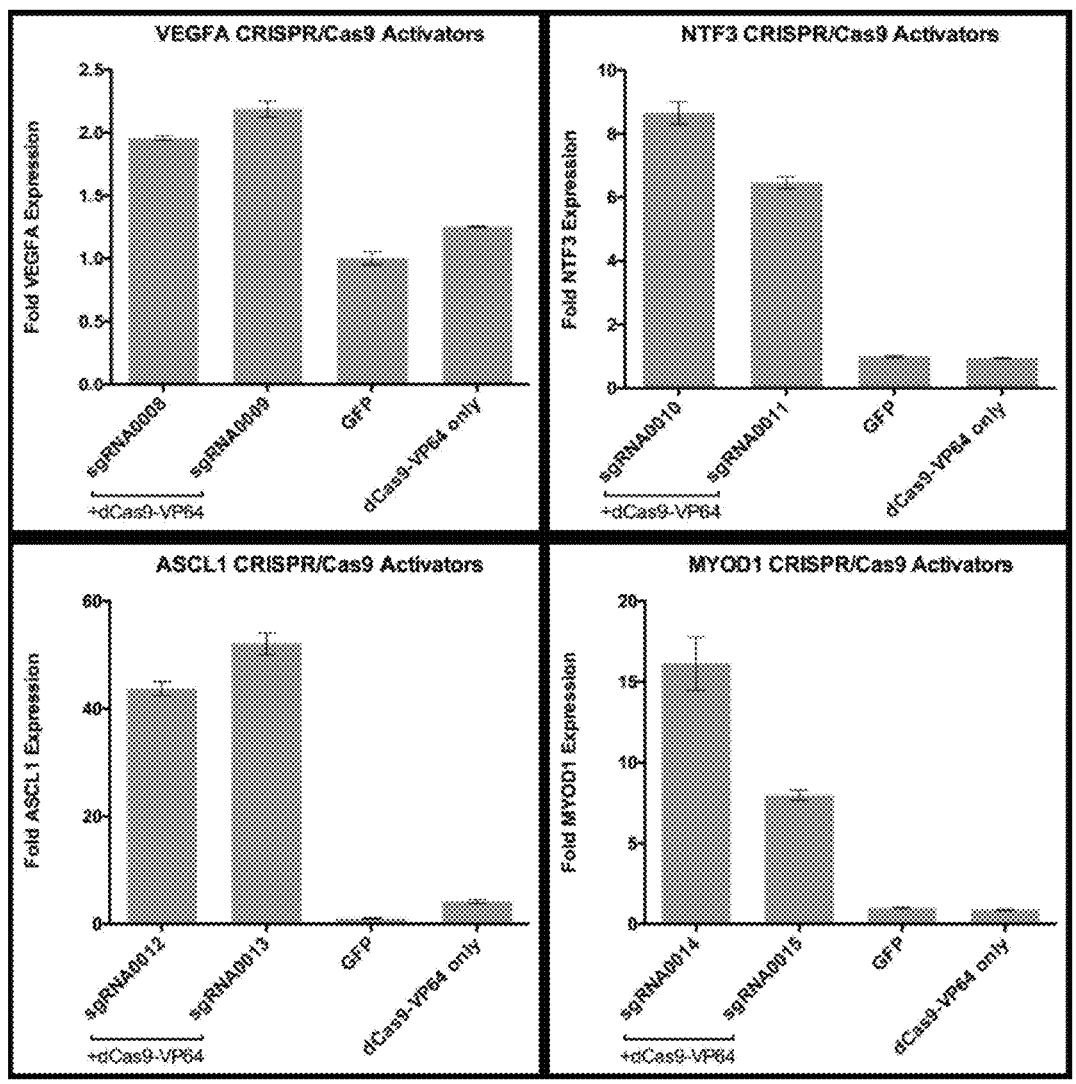
FIG. 21 shows the basal gene expression modulation of dCas9-VP64 that was measured for the indicated gene targets. Italics represent mouse gene targets tested in Neuro 2A cells, all caps represent human gene targets tested in 293FT cells. In each case, expression of the gene in GFP transfected cells was compared to expression in cells transfected with dCas9-VP64.
Figure 22:
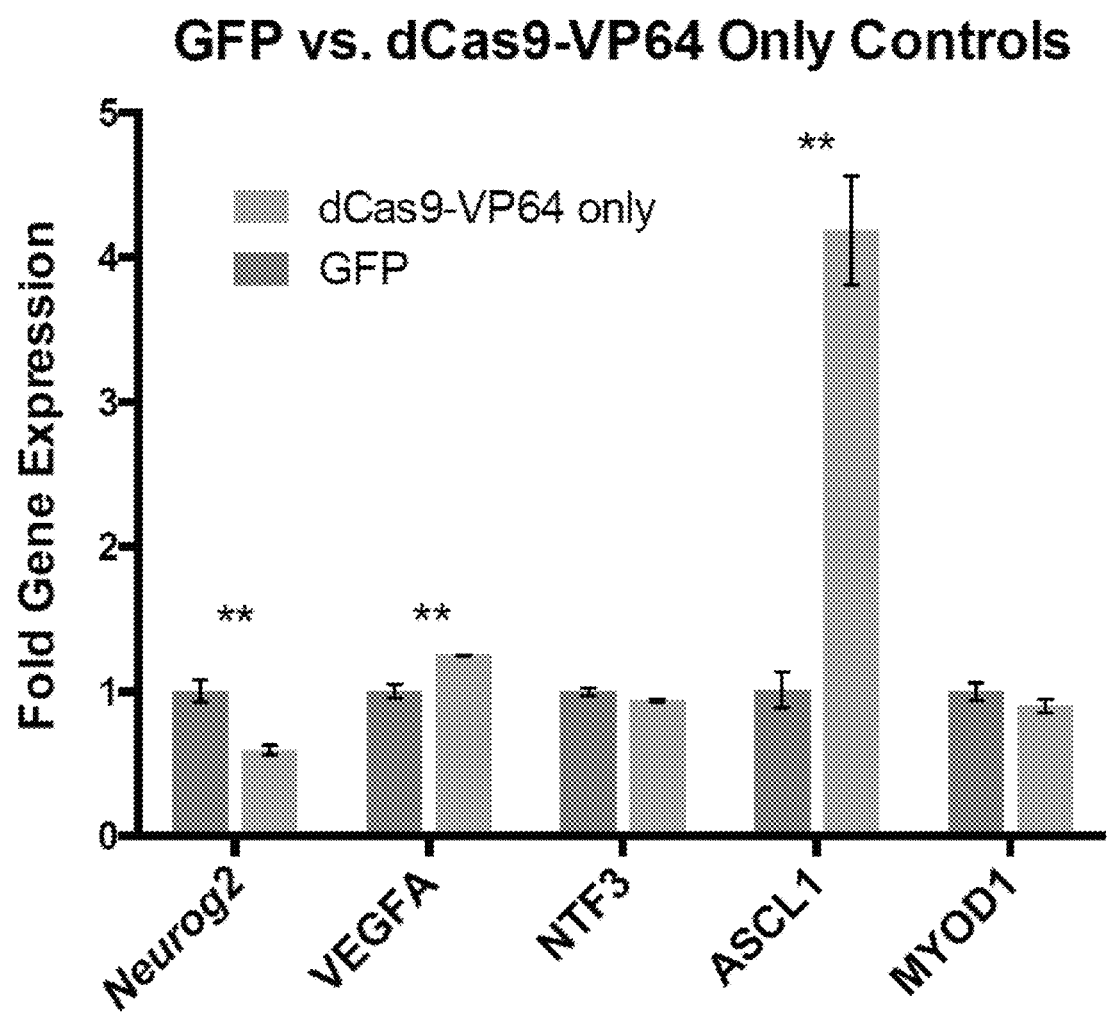
FIG. 22 shows the changes in expression level of the indicated genes when samples transfected with the dCas9-VP64 construct, but without an sgRNA.

Experimental results for Human Cell Line Experiments: As shown in FIG. 21, sgRNAs targeted to several human genes (ASCL1, MYOD1, VEGFA, and NTF3) successfully induced upregulation of the desired mRNA using Applicants pXRP057 dCas9-VP64 construct (Konermann et al., Optical control of mammalian endogenous transcription and epigenetic states. Nature. 2013 Aug. 22; 500(7463):472-6). Applicants showed that samples transfected with the dCas9-VP64 construct, but without an sgRNA had significant changes in expression level for several genes and further characterization is to be carried out (FIG. 22). The PAM counts (−100 to +100 bp of TSS) are indicated below:

| Gene | Basal Fold Change | NGG + NAG counts |
|---|---|---|
| Neurog2 | 0.60 | 213 |
| VEGFA | 1.25 | 211 |
| NTF3 | 0.94 | 203 |
| ASCL1 | 4.19 | 235 |
| MYOD1 | 0.90 | 204 |

Example 7

Further Studies on the Cas9 Modulator-Activator and Repressor Data

Figure 26:
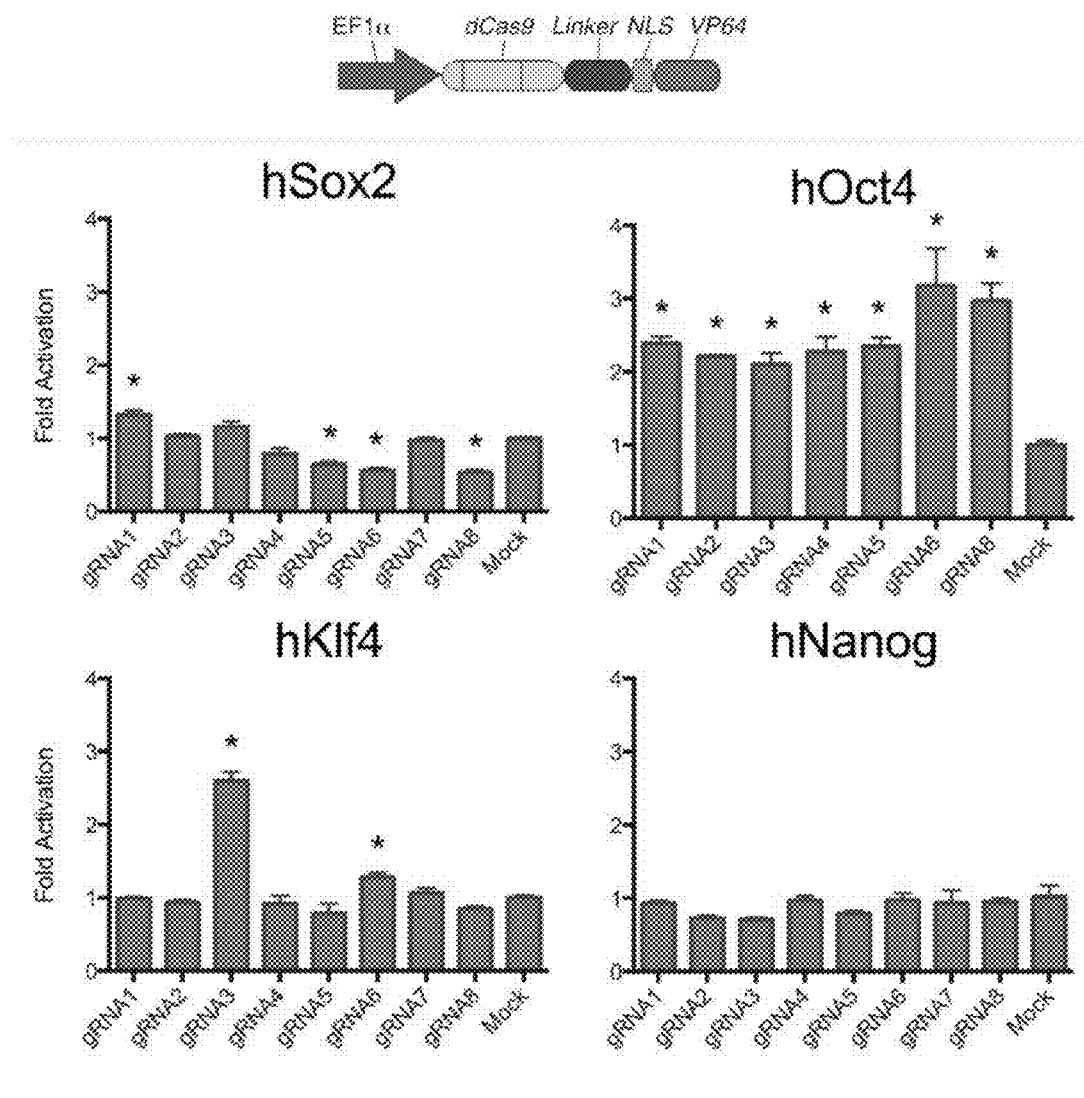
FIG. 26 shows the graphical representation of fold activation of different genes targeted by the Cas9 activator (pXRP57) and guide RNA.
Figure 27:
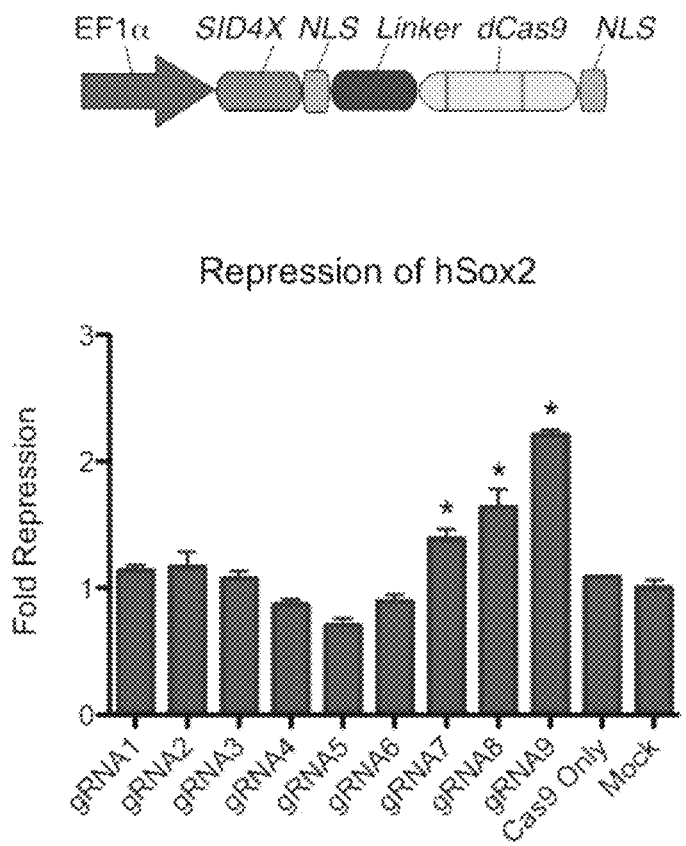
FIG. 27 shows the graphical representation of fold repression of the hSox2 gene targeted by the Cas9 activator (pXRP57) and guide RNA.

Applicants carried out studies to further develop the dCas9 activator (pXRP57) and repressor (pXRP48) (FIG. 23). Applicants cloned plasmids pXRP57 and pXRP48 (Konermann et al., Optical control of mammalian endogenous transcription and epigenetic states. Nature. 2013 Aug. 22; 500 (7463):472-6). The Cas9 activator sequence is indicated in FIG. 24 and the Cas9 repressor sequence is indicated in FIG. 25. Additional data was collected for the activator (FIG. 26), and repressor (FIG. 27). A list of guide RNAs used in the experiment is listed below:

| Gene | guide RNA | SEQ ID NO: |
|---|---|---|
| hSox2-1 | GTGGCTGGCAGGCTGGCTCT | 45 |
| hSox2-2 | GGCCTCCCCCGCGCGGCCGG | 46 |
| hSox2-3 | GCCCCCTTTCATGCAAAACC | 47 |
| hSox2-4 | GACAGCCCCGTCACATGGA | 48 |
| hSox2-5 | GGCAGGCGAGGAGGGGGAGG | 49 |
| hSox2-6 | GGCGGGGCCTCCCGCGCCGC | 50 |
| hSox2-7 | GCTGCCGGGTTTTGCATGAA | 51 |
| hSox2-8 | GGGGCTGTCAGGGAATAAAT | 52 |
| hKlf4-1 | GAGAGAACGAACGTGTCTGC | 53 |
| hKlf4-2 | GAGGGTCACTCGGCGGCTCC | 54 |
| hKlf4-3 | GCGCGCTCCACACAACTCAC | 55 |
| hKlf4-4 | GGGGCTGTGGCCGGGGCGGT | 56 |
| hKlf4-5 | GGCGACCGCGACAGTGGTGG | 57 |
| hKlf4-6 | GCAAAAATAGACAATCAGCA | 58 |
| hKlf4-7 | GAAGGATCTCGGCCAATTTG | 59 |
| hKlf4-8 | GTGGGGCCCAGAAGGTCCT | 60 |
| hNanog-1 | GCCACGGCCTCCCAATTTAC | 61 |
| hNanog-2 | GGAATATGGTTCAACAGGAA | 62 |
| hNanog-3 | GCTGCAGAGTAACCCAGACT | 63 |
| hNanog-4 | GCCTTGGTGAGACTGGTAGA | 64 |
| hNanog-5 | GATTAACTGAGAATTCACAA | 65 |
| hNanog-6 | GTGTGCCCGCCAGGAGGGT | 66 |
| hNanog-7 | GTTGCCTGCATAATAACATG | 67 |
| hNanog-8 | GGAGGAAAAATTTAAGAGG | 68 |
| hOct4-1 | GGACCGGGATTGTCCAGCCA | 69 |
| hOct4-2 | GAGTGATAAGACACCCGCTT | 70 |
| hOct4-3 | GCAGCTGGCCATTGTGCTTA | 71 |
| hOct4-4 | GGAGAGGGGGTCAAGCACCT | 72 |
| hOct4-5 | GCGGGTTGGGAGTTGAAAGT | 73 |
| hOct4-6 | GCTCCAGCCTCCTAAGTGGC | 74 |
| hOct4-7 | GGAGGTGGGGGGAGAAACTG | 75 |
| hOct4-8 | GGTGAAATGAGGGCTTGCGA | 76 |

Example 8

CRISPR/Cas9 Activator System with the Light-Inducibility of the LITE System

Applicants combined the RNA guidance of the CRISPR/Cas9 activator system with the light-inducibility of the LITE system. An inducible expression system based on CRISPR/

Cas9 may make the inducible screen of many gene targets much faster and easier than previously possible, while also providing the opportunity to easily multiplex different targets by combining sgRNAs targeted to disparate genetic loci.

Figure 28:
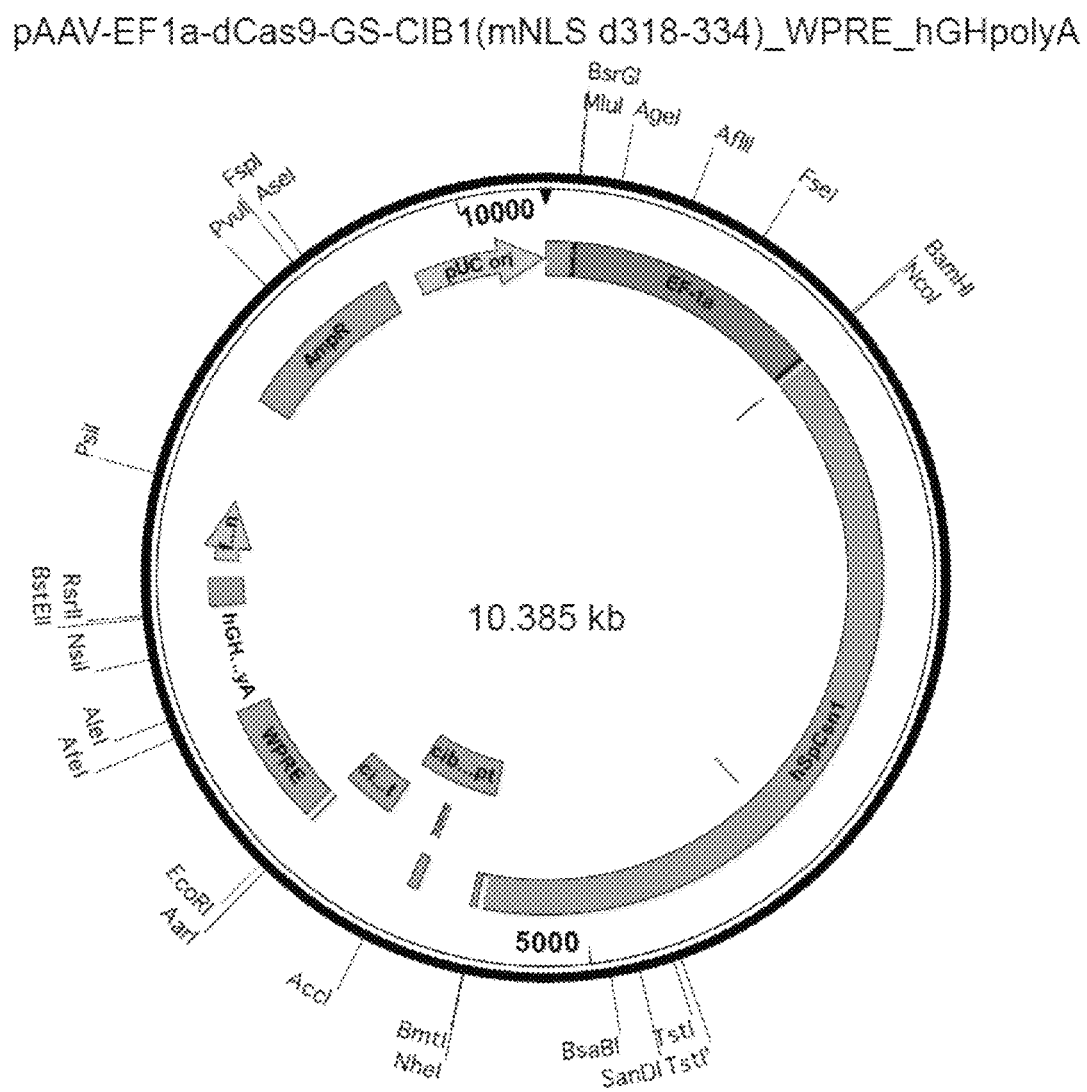
FIG. 28 shows a pAAV-EF1a-dCas9-GS-CIB1(mNLS d318-334)_WPRE_hGHpolyA plasmid map.
Figure 29:
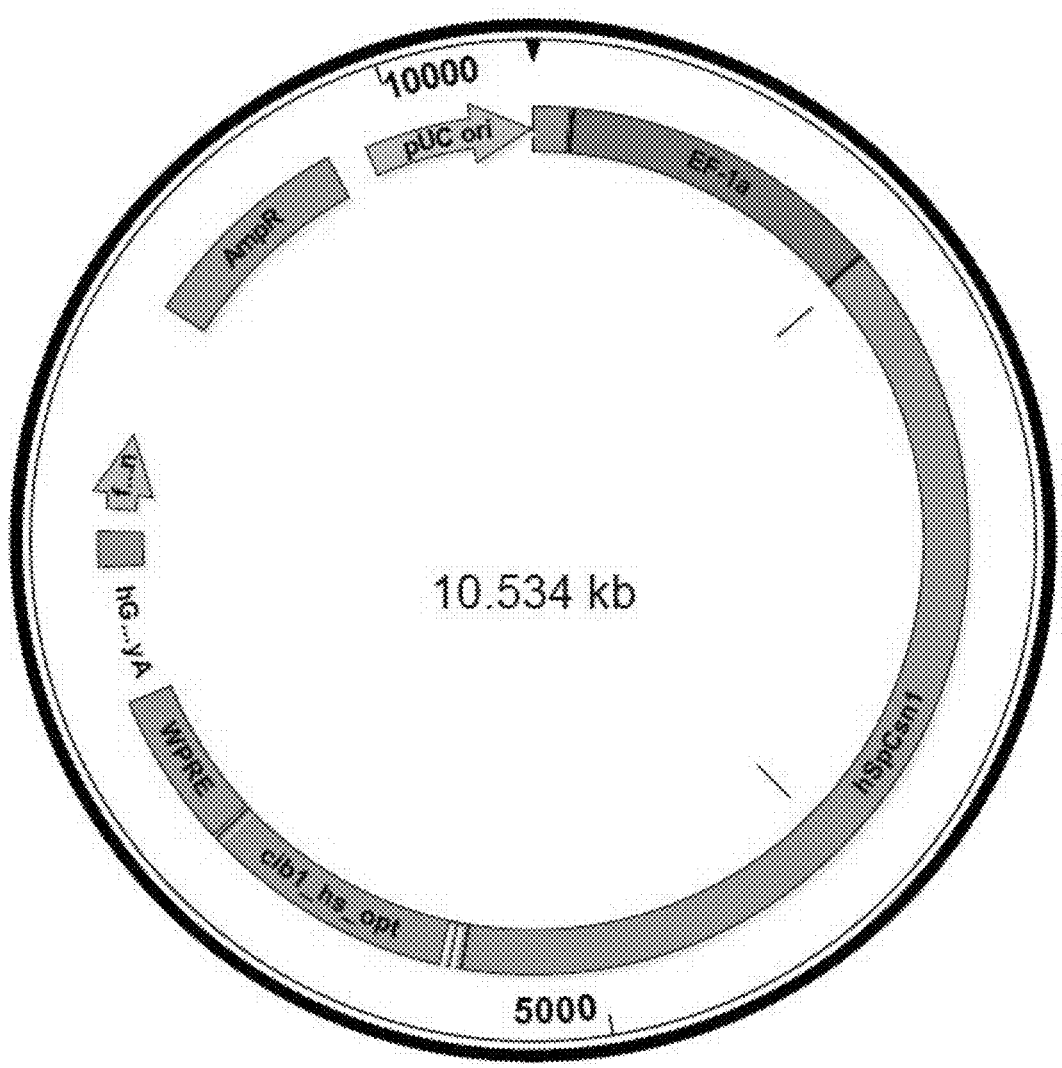
FIG. 29 shows a pAAV-EF1a-dCas9-GS-NLS-cib1-WPRE-hGHpA plasmid map.
Figure 30:
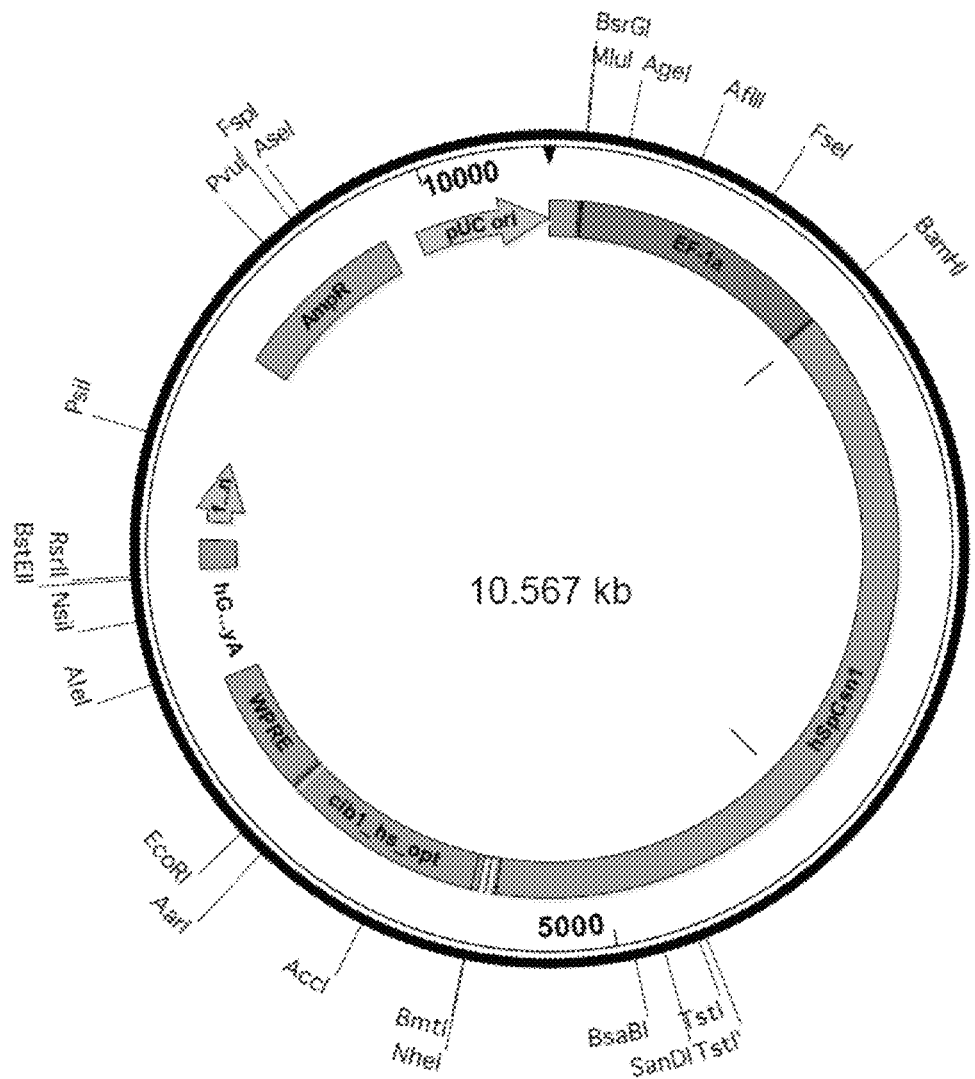
FIG. 30 shows a pAAV-EF1a-dCas9-GS-NLS-NLS-cib1-WPRE-hGHpA plasmid map.

Materials and methods: The CasLITE system consists of 3 components: a dCas9-CIB1 fusion protein, the CRY2PHR-VP64 construct, and an sgRNA guide sequence. Applicants synthesized 3 different versions of dCas9-CIB1: (1) dCas9-GS-NLS-CIB1 comprising the double mutant (D10A H840A) dCas9 from our pXRP057 plasmid, a glycine serine linker, SV40 nuclear localization signal, and CIB1 from LITE1.0 (2) dCas9-GS-NLS-NLS-CIB1 comprising the double mutant dCas9, glycine serine linker, 2 SV40 NLS sequences, and CIB1 from LITE1.0. (3) dCas9-GS-CIB1 (mNLS d318-334) comprising the double mutant dCas9, glycine serine linker from LITE2.0, and CIB1 from LITE2.0. Vectors used in the practice of the invention are illustrated in FIGS. 28, 29, 30.

Applicants selected sgRNA sequences targeted to ASCL1 and MYOD1, previously validated with a constitutive dCas9-VP64 activator, for testing the CasLITE systems in human cells. Guide sequences were cloned by the golden gate method into the px362 plasmid containing the U6 promoter upstream of a chimeric sgRNA cloning backbone.

293FT cells were cultured in D10 medium without HEPES (10:1 ratio of DMEM high glucose w/Glutamax and sodium pyruvate: fetal bovine serum). For transfection, 100K cells in 0.5 mL culture medium were plated in each well of a 24 well plate. After 22 h in culture, each well of 293FT cells was transfected with 1.5 ug of DNA using 7.5 uL of Lipofectamine following the recommended steps of the manufacturer (Life Technologies). For all CasLITE+sgRNA samples, 0.5 ug dCas9-CIB1 plasmid, 0.5 ug of CRY2PHR-VP64 plasmid (LITE1.0 or LITE2.0 to match CIB1), and 0.5 ug sgRNA expression plasmid were used. Experiments with 4 sgRNAs used equal masses of each of 4 sgRNAs totaling 0.5 ug. For control samples, plasmid masses were replaced by GFP expressing plasmid as necessary. 4h after transfection, the medium was replaced with 1 mL culture medium. 48h after transfection excitation was started on light stimulated samples using 5 mW/cm2 475 nm blue light. 12h after starting stimulation, all samples, including all controls, were harvested for RNA using the Macherey Nagel Nucleospin 96 RNA kit. Reverse transcription was performed with qScript cDNA supermix according to the manufacturer's protocol. qPCR was performed using Taqman probes and Taqman Fast Advanced Master Mix from Life Technologies on a Roche LightCycler 480 II real-time PCR machine.

Figure 31:
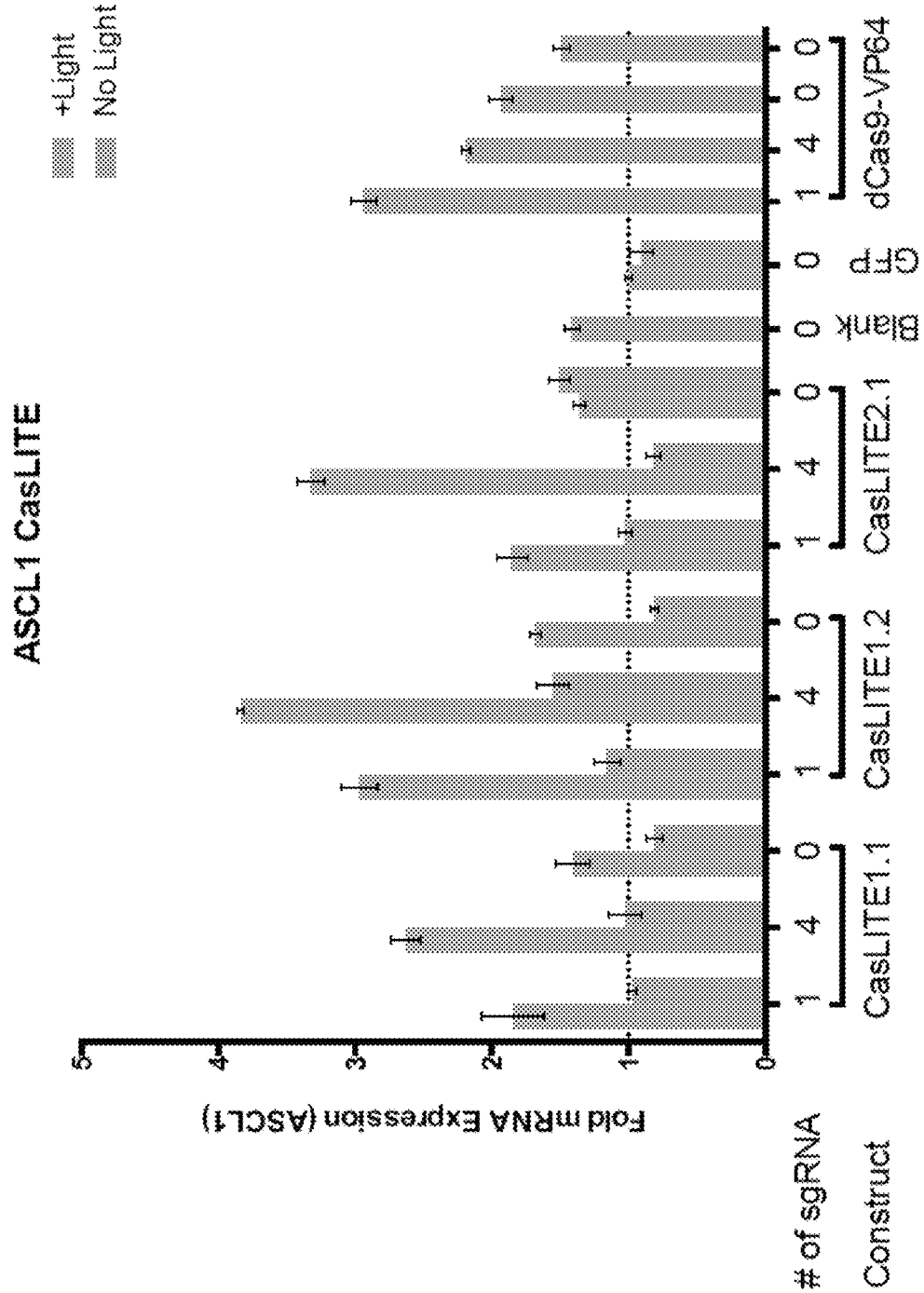
FIG. 31 shows a graphical representation of CasLITE constructs exhibiting varying levels of light-inducible transcriptional activation.

Results: CasLITE constructs exhibited varying levels of light-inducible transcriptional activation (FIG. 31). Though the initial functionality of the system appears to be modest, calling for repeated experimentation, these results suggest the possibility for light-inducible RNA-guided transcriptional activation.

Example 9

Cas9 Mouse Model and Validation of Mouse Embryonic Stem Cell Line

Figure 33:
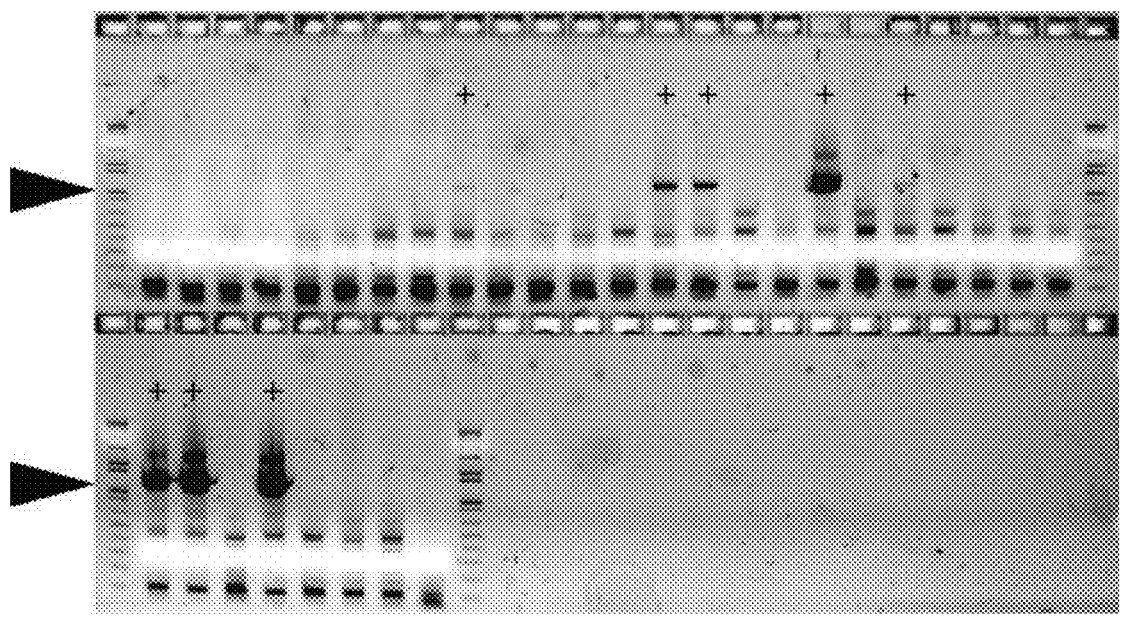
FIG. 33 shows a gel image indicating the genotyping results for Cas9 mice.

Applicants validated a mouse embryonic stem cell line that was modified to include the Cre-dependent Cas9 cassette (pCM2) into the Rosa26 locus (FIG. 32) and obtained genotyping results for germ line transmitted founders (FIG. 33).

To validate that the Cas9 cassette was functional, the modified mESC line was electroporated with the designated constructs in FIG. 32. The mESC line was used for blastocyst injection into C57BL/6J recipients (performed by the DCM at MIT). Six chimeric progeny were produced and then backcrossed to the C57BL/6J background. Successful germ line transmission was identified on the basis of agouti coat color. Two of the six chimerics produced germ line transmitted pups. Genomic DNA was extracted from tissue from the Cas9 mice and Rosa26 short arm genotyping PCR was performed (FIG. 33). A 1.5 kb band is the correct size for correctly inserted transgenes into the Rosa26 locus. These results demonstrate the successful germ line transmission of the Cre-dependent Cas9 transgene in the Rosa26 locus.

The benefit of the Rosa26 Cre-dependent Cas9 knockin line is that it can be crossed to any Cre driver line to enable Cas9 expression. Moreover, Cas9 can be activated by the delivery of Cre by viral vector or other delivery means. This enables cell type, tissue, and developmental specificity of Cas9 expression. An additional benefit is that the mouse can be used for isolation of primary cells. This would be particularly useful in the case of a primary cell type that is not amenable to the delivery of nucleic acids or cannot be cultured long enough for the utilization of viral vectors.

Example 10

RNA-Targeted CRISPR-Based Platform for Mammalian Epigenome Engineering

Applicants develop an RNA-targeted CRISPR-based platform for mammalian epigenome engineering. Two RNA-targeted CRISPR-mediated immune systems, CRISPR/Cmr loci, were recently characterized from *Pyrococcus furiosus* and *Sulfolobus solfataricus*. Based on protein homology these CRISPR/Cmr loci are part of a much larger family that exists within a diversity of bacterial and archaeal genomes. Similar to RNAi and Cas9 the interference mechanism of a CRISPR/Cmr locus is based on the homology of a short stretch of nucleotides and is thus amenable to genome-wide screens. Moreover, the homology region to the target site is significantly increased making the potential for specificity much greater.

Figure 34:
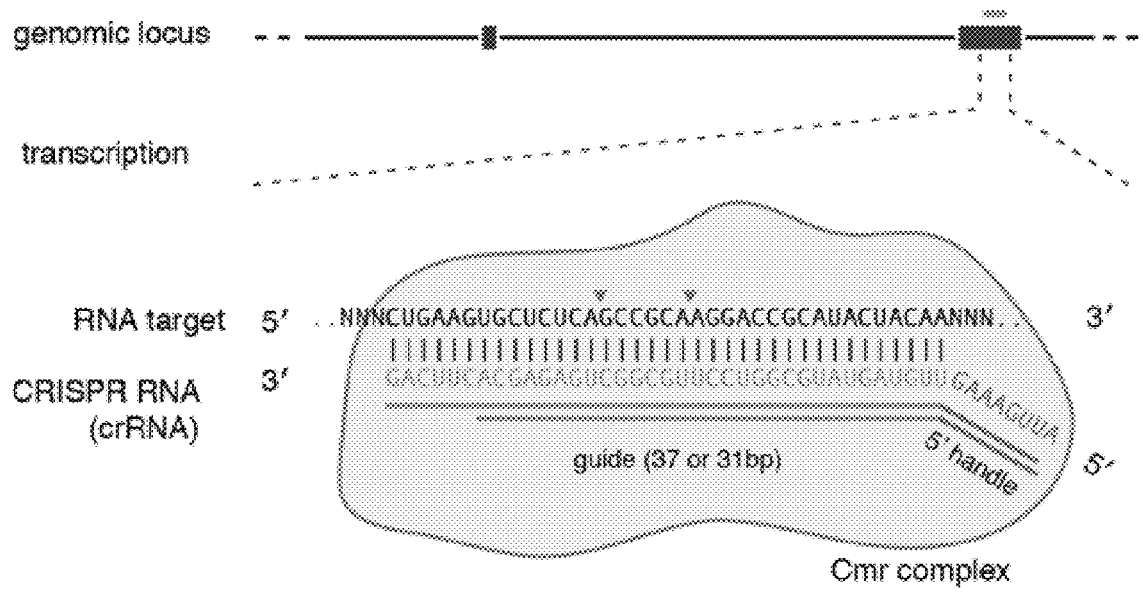
FIG. 34 shows CRISPR/Cmr mediated silencing of RNA. Cmr proteins form a complex with mature crRNA to site-specifically target and cleave RNA. Mature crRNAs from P. furiosus exist in two forms of different lengths, long (45 nt) and short (39 nt), consisting of a 5' handle and a guide sequence. The 5' handle is required for the crRNA to be included in the Cmr complex. The guide sequence programs the target site and can be either long (37 nt) or short (31 nt). RNA cleavage occurs 14 nucleotides from the 3' end of the crRNA. This platform could be repurposed to target mammalian genes expressed from a genomic locus by only changing the guide sequence.

Applicants conduct a metagenomic analysis of the CRISPR/Cmr family, development of an in vitro assay system to identify functional loci, and characterization of the specificity and capacity for multiplexing in mammalian cells. A site-specific RNA-targeted CRISPR-based genome engineering platform (FIG. 34) can replace the many utilities of RNAi and provide a system for perturbing RNA biology that has never before been possible.

Preliminary work with the CRISPR/Cmr locus from *P. furiosus*: Based on the extensive knowledge base on the CRISPR/Cmr locus from *P. furiosus* Applicants investigated the feasibility of expressing the Cmr genes within mammalian cells. Genomic DNA from *P. furiosus* was obtained from ATCC and used as a PCR template to amplify the six Cmr genes (Cmr1-6). Applicants also amplified another protein within the locus, Cas6. Cas6 is involved with the processing of crRNA into its mature form. Although only five Cmr genes (Cmr1,2,3,4,6) are essential Applicants considered that Cas6 may aid in troubleshooting if the five Cmr genes happened to be insufficient in the mammalian context.

Figure 35:
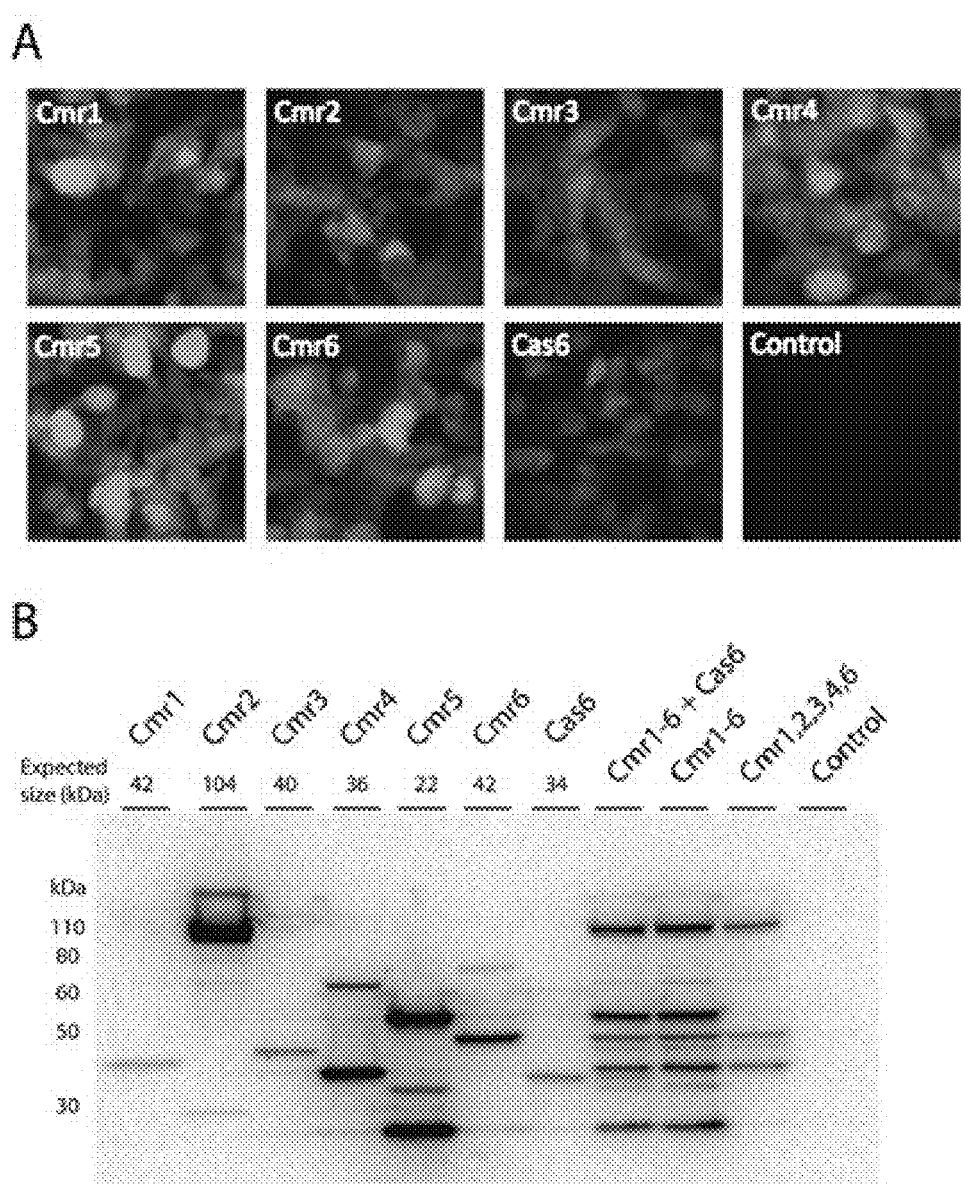
FIG. 35A-B shows Cmr proteins are expressed within mammalian cells. Six Cmr genes (Cmr1-6) and one Cas gene (Cash) from *P. furiosus* were cloned into mammalian expression vectors and transfected into HEK 293FT cells. 72 hours post-transfection fluorescence images were taken and protein lysates were prepared. A) EGFP expression is strongly observed suggesting that the exogenous proteins are robustly expressed. B) Western blot images show protein bands located at the expected size. The second band within each lane is 30 kDa larger in each case and is likely the result of uncleaved P2A sequence.

Cmr1-6 and Cas6 were cloned into mammalian expression plasmids and transfected into HEK 293FT cells. For easy visualization the cloning plasmid contained an HA tag and a P2A-EGFP sequence. The P2A sequence causes a ribosomal skip resulting in two mature proteins from the same transcript. 72 hours post-transfection EGFP fluorescence was observed for each Cmr expression plasmid (FIG. 35A), suggesting that Cmr1-6 and Cas6 are successfully being expressed. To validate that the proteins are stable within the mammalian cell environment and are also the correct size Applicants performed a western blot (FIG. 35B). Within each lane there is a band of the expected size, suggesting that each protein is being expressed and is stable within mammalian cells. The larger second band that appears within each lane may be a result of failure of the P2A sequence to cause a ribosomal skip and thus one protein fusion is created and not two individual protein products. The band located above the predicted size is ~30 kDa larger than the expected size, which corresponds to P2A-EGFP. Applicants will confirm this by immunostaining the same blot using an anti-EGFP antibody and should see two bands per lane, one that is the size of P2A-EGFP and another larger band the size of Cmr-P2A-EGFP. The western blot results also show variable expression for the seven proteins, whereas, Cmr1, Cmr3, and Cmr6 have low expression while Cmr2, Cmr4, and Cmr5 have high expression. Applicants demonstrated that it is indeed possible to express Cmr proteins from *P. furiosus* within mammalian cells.

In this example, Applicants identify putative RNA-targeted CRISPR/Cmr loci and validate the expression of individual proteins and corresponding crRNAs in mammalian cells. Using a homology-based approach Applicants identify putative RNA-targeted CRISPR/Cmr loci across a diversity of bacterial and archaeal genomes. Cmr proteins and crRNAs from each locus are identified and validated through cloning, transfection into mammalian cells, and detection by western blot and northern blot, respectively. The methodology is as follows:

1. Identify RNA-targeted CRISPR loci: Identification of RNA-targeted CRISPR loci from published work is the first step in understanding the essential components of a functional Type CRISPR/Cmr system. Two RNA-targeted loci from two different organisms have been published and characterized to different extents.

2. Identify putative RNA-targeted CRISPR loci across a diversity of bacterial and archaeal species: Extensive work has been done towards classifying all known CRISPR loci into phylogenetic groups and has thus resulted in high confidence databases of orthologous proteins. Using the most extensive and manually curated databases Applicants identify putative CRISPR/Cmr loci based on the presence of multiple Cmr protein orthologs. I will pick a subset that spans the diversity of CRISPR/Cmr loci for further molecular characterization in a broad attempt to sample the natural diversity.

3. Identify Cmr proteins and crRNAs within CRISPR/Cmr loci: CRISPR/Cmr loci are well studied and many bacterial and archaeal genomes have been extensively annotated so the identification of Cmr proteins should be straightforward in these cases. However, in the absence of good annotation the problem will be more complicated. For this reason Applicants preferentially select CRISPR/Cmr loci from organisms where good annotations are available. If these strategies do not provide comprehensive coverage of the diversity CRISPR/Cmr loci Applicants use a homology-based approach combined with ORF prediction algorithms to identify the Cmr proteins. CRISPR repeat arrays have predictable structures and are located near the Cmr CRISPR associated proteins. The CRISPR array consists of a leader sequence that drives expression of the entire array of repeats and spacers creating a primary transcript that is extensively processed to make mature CRISPR RNAs (crRNA)s. Existing computational tools (CRISPRFinder) will allow for identification of the repeat arrays. Predicting the mature crRNA from each locus may not be as straightforward and may require optimization. There are general features known about mature crRNAs from Type III-B CRISPR/Cmr loci that Applicants use to predict novel crRNAs. All identified mature crRNAs from Type III-B CRISPR loci have a 5' handle that is part of the repeat sequence followed by a spacer. The 5' handle functions in the recognition of the crRNA by the Cmr complex and the spacer guides the Cmr complex to target RNA through Watson-Crick base pairing. Applicants design a panel of likely crRNA architectures that are of different total length and have 5' handles of different length as it is difficult to predict any specific unique features of novel crRNAs a priori.

Figure 36:
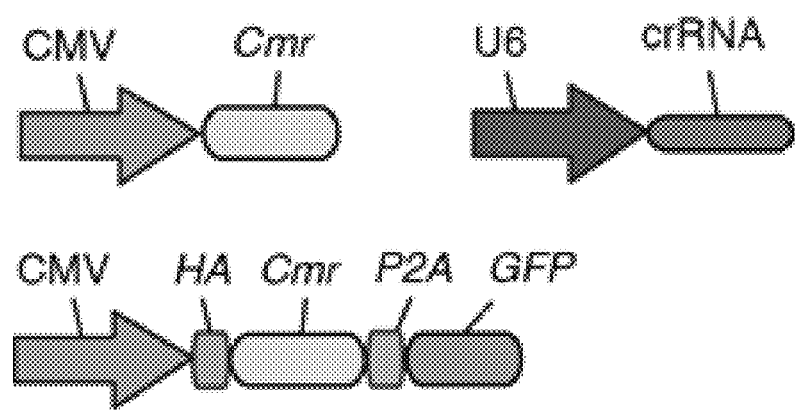
FIG. 36 shows CRISPR/Cmr expression vectors.

4. Clone Cmr proteins and crRNAs into mammalian expression vectors: Cmr proteins are individually cloned into two different mammalian expression vectors (FIG. 36). The first vector (V1.0) expresses individual Cmr proteins using a CMV promoter, bovine growth hormone polyA tail sequence, and a WPRE element to maximize protein expression. The second vector (V1.2) uses the same elements as in V1.0 but will include an N-term HA tag and a C-term P2A-EGFP sequence. The HA tag enables protein detection and quantification and the P2A-EGFP enables an easy visual method for detecting expression in mammalian cells. Applicants make both versions because the impact of adding an HA tag and a P2A peptide on Cmr proteins and how that influences correct formation of the Cmr complex is unknown. crRNAs is expressed using the human U6 promoter, which has been successfully used to express noncoding RNAs utilized for RNAi and DNA-targeted CRISPR/Cas9.

5. Validate Cmr protein and crRNA expression: Cmr protein expression is validated by transfecting V1.2 plasmids into HEK 293FT cells and observing EGFP expression. To further validate that the protein is expressed and the correct size Applicants prepare protein lysates from transfected cells and perform a western blot using an anti-HA tag antibody. To validate crRNA expression Applicants purify small RNAs from transfected cells and probe by northern blot.

Applicants demonstrate RNA cleavage in an in vitro mammalian cell lysate assay using naturally encoded crRNAs. Applicants develop a simple mammalian cell lysate in vitro assay to rapidly validate putative CRISPR/Cmr loci. Cell lysates of mammalian cells transfected with Cmr proteins are prepared and incubated with naturally encoded crRNAs and a corresponding RNA target. Functioning CRISPR/Cmr loci are identified on the bases of correctly sized cleavage products using gel electrophoresis. The methodology is as follows:

1. Expression of Cmr proteins in mammalian cells and preparation of cell lysates: Applicants transfect individual expression plasmids for all Cmr proteins of a species into HEK 293FT cells and wait 72 hours for robust protein expression to occur. The cells are lysed, homogenized, and aliquoted for future use. Although not all cells are transfected with each Cmr plasmid, once the lysates are prepared all Cmr proteins will be in the same mixture. This is a beneficial over the live cell model where cotransfection of seven components may be challenging. Moreover, this will give Applicants absolute control over the final concentration of the crRNA and target RNA in the reaction.

2. Preparation of crRNAs: For each CRISPR/Cmr locus Applicants make mature crRNAs containing the endogenous spacer. Specifically Applicants utilize the spacer sequence of the crRNA nearest the leader. As was discussed previously Applicants experiment with different crRNA architectures with different 5' ends. A direct method for creating mature crRNA of a defined sequence is in vitro transcription using commercially available T7 transcription kits.

3. In vitro transcribe RNA harboring crRNA target sequences: T7 expression plasmids are cloned to uniquely harbor sequences targeted by the endogenous spacer of each CRISPR/Cmr locus. This target will be cloned into the middle of a ~1 kb piece of RNA so that resulting cleavage products will be easily visualized on an agarose gel.

4. Perform and optimize in vitro mammalian cell lysate cleavage experiment: Once all of the components are prepared Applicants combine and incubate the cell lysates, individual crRNAs, and target RNA followed by visualization on an agarose gel. Functional CRISPR systems are identified on the basis of cleavage products of the correct size. Certain parameters are kept in mind. Parameters for optimization are Cmr protein identity and concentration, crRNA architecture and concentration. Less significant parameters for optimization are buffer content and concentration, crRNA and RNA stability, reaction time, and RNA visualization.

Applicants demonstrate and characterize knockdown of endogenous mammalian genes using novel crRNAs. crRNAs are engineered to target endogenous mammalian genes and cotransfected with Cmr expression plasmids into mammalian cells. mRNA and protein knockdown are quantified by quantitative PCR and western blot. The multiplexing capability is investigated by targeting multiple genes at the same time. The specificity is characterized and compared to RNAi using RNA-seq. The methodology is as follows:

1. Target crRNAs to endogenous mammalian genes: With functionally validated RNA-targeted CRISPR/Cmr loci Applicants design novel crRNAs targeting three genes that are therapeutically validated RNAi targets, namely, P53, VEGF, and CTNNB1 (Beta-catenin). Applicants pick eight target sites within each gene to help resolve any sequence-specific limitations of the technology. For different CRISPR/Cmr loci the exact target sight may differ by a few bases because of the unique required features of each crRNA but Applicants target a consistent region to aid in comparisons.

2. Quantify and characterize mRNA knockdown: Applicants test the CRISPR/Cmr systems in HEK 293 FT cells by transfecting mammalian expression plasmids for Cmr protein components and individual crRNAs. Cleaved mRNAs are rapidly degraded in the cell, whereas, the resulting RNA fragments do not have both a 5' cap and a polyA tail. Applicants quantify the extent of mRNA knockdown by performing quantitative PCR. When mRNA knockdown is observed Applicants perform a western blot for the targeted protein.

In addition to single crRNA transfection experiments Applicants add multiple crRNAs targeted to the same gene. It was observed previously that other transcriptional modulators work synergistically when targeted to multiple sites within the same region. This is also a useful strategy to identify suboptimal CRISPR/Cmr systems that do not function when using single crRNAs but can function overall and just need to be optimized for one reason or another. Applicants also add multiple crRNAs targeting different genes in the same condition to further consider multiplexing in this system. This has broad implications for pathway engineering and genome-scale screens.

3. Characterize specificity by RNA-seq: A major motivation of this work is to develop an RNA-targeting platform with greater specificity than RNAi. Inherently there is a greater opportunity for the CRISPR/Cmr system to have better specificity because the extended complementarity to the target site. However, each base pair within the guide may not be necessary or there may be some tolerance to mismatches. To understand these characteristics of the CRISPR/Cmr system Applicants will use an HEK 293T derived cell line that expresses a single copy of EGFP. Applicants target EGFP for knockdown using 24 unique crRNAs. Using an HEK/GFP cell line makes the off-target analysis straightforward because EGFP may be considered an innocuous protein that has no influence on cellular processes so any altered transcripts are likely off-target effects. Results are compared to an siRNA targeting EGFP with known off-target effects. Due to the extended base pairing capacity of the CRISPR/Cmr complex Applicants expect the off-targets to be reduced. The tolerance to mismatches is also explored and this will be important for future development of the CRISPR/Cmr platform.

Given that an RNA-targeted CRISPR/Cmr system functions in mammalian cells Applicants initially pursue two applications: genome-scale screens and a catalytically inactive RNA-binding platform. A genome-scale RNAi screen is a powerful method for probing biology. However, high off-target effects severely limit the approach. A platform with higher specificity could either replace RNAi genomic-screens or provide an orthogonal approach that would aid in identifying true positives. An RNA-targeted CRISPR/Cmr platform is amenable to genomic screens because each target is programmed by only a few nucleotides, whereby, a complex library could easily be synthesized and delivered.

A catalytically inactive RNA-binding platform is an enabling technology for the development of effector complexes that aid in the probing of RNA. Applicants identify the catalytically active components of the Cmr complex and mutate the specific residues responsible. This has been done successfully in a number of cases, e.g. this was done for CRISPR/Cas9 to create a nickase and a transcriptional modulator. Utilizing this platform Applicants develop a technology to detect and image RNA transcripts inside the cell. This has applications for understanding the influence of RNA localization on cellular processes and in vivo detection and quantification of RNA. Alternatively Applicants add effector molecules onto an RNA-binding platform towards probing and understanding areas of RNA biology that are not well understood, namely RNA editing and epigenetics.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

REFERENCES

Barrangou, R., Fremaux, C., Deveau, H., Richards, M., Boyaval, P., Moineau, S., . . . Horvath, P. (2007). CRISPR provides acquired resistance against viruses in prokaryotes. Science (New York, N.Y.), 315(5819), 1709-12. doi: 10.1126/science.1138140

Birmingham, A., Anderson, E. M., Reynolds, A., Ilsley-Tyree, D., Leake, D., Fedorov, Y., . . . Khvorova, A. (2006). 3' UTR seed matches, but not overall identity, are associated with RNAi off-targets. Nature methods, 3(3), 199-204. doi:10.1038/nmeth854

Brouns, S. J. J., Jore, M. M., Lundgren, M., Westra, E. R., Slijkhuis, R. J. H., Snijders, A. P. L., . . . van der Oost, J. (2008). Small CRISPR RNAs guide antiviral defense in prokaryotes. Science (New York, N.Y.), 321(5891), 960-4. doi:10.1126/science.1159689

Burnett, J. C., Rossi, J. J., & Tiemann, K. (2011). Current progress of siRNA/shRNA therapeutics in clinical trials. Biotechnology journal, 6(9), 1130-46. doi:10.1002/biot.201100054

Cheong, C.-G., & Hall, T. M. T. (2006). Engineering RNA sequence specificity of *Pumilio* repeats. Proceedings of the National Academy of Sciences of the United States of America, 103(37), 13635-9. doi:10.1073/pnas.0606294103

Cong, L., Ran, F. A., Cox, D., Lin, S., Barretto, R., Habib, N., . . . Zhang, F. (2013). Multiplex Genome Engineering Using CRISPR/Cas Systems. Science (New York, N.Y.). doi:10.1126/science.1231143

Elbashir, S. M., Harborth, J., Lendeckel, W., Yalcin, A., Weber, K., & Tuschl, T. (2001). Duplexes of 21-nucleotide RNAs mediate RNA interference in cultured mammalian cells. Nature, 411(6836), 494-8. doi:10.1038/35078107

Fire, A., Xu, S., Montgomery, M. K., Kostas, S. A., Driver, S. E., & Mello, C. C. (1998). Potent and specific genetic interference by double-stranded RNA in *Caenorhabditis elegans*. Nature, 391(6669), 806-11. doi:10.1038/35888

Hale, C., Kleppe, K., Terns, R. M., & Terns, M. P. (2008). Prokaryotic silencing (psi)RNAs in *Pyrococcus furiosus*. RNA (New York, N.Y.), 14(12), 2572-9. doi:10.1261/rna.1246808

Hale, C. R., Majumdar, S., Elmore, J., Pfister, N., Compton, M., Olson, S., . . . Terns, M. P. (2012). Essential features and rational design of CRISPR RNAs that function with the Cas RAMP module complex to cleave RNAs. Molecular cell, 45(3), 292-302. doi:10.1016/j.molcel.2011.10.023

Hale, C. R., Zhao, P., Olson, S., Duff, M. 0., Graveley, B. R., Wells, L., . . . Terns, M. P. (2009). RNA-guided RNA cleavage by a CRISPR RNA-Cas protein complex. Cell, 139(5), 945-956.

Hou, Z., Zhang, Y., Propson, N. E., Howden, S. E., Chu, L.-F., Sontheimer, E. J., & Thomson, J. A. (2013). Efficient genome engineering in human pluripotent stem cells using Cas9 from *Neisseria meningitidis*. Proceedings of the National Academy of Sciences of the United States of America, 110(39), 15644-9. doi:10.1073/pnas.1313587110

Ishino, Y., Shinagawa, H., Makino, K., Amemura, M., & Nakata, A. (1987). Nucleotide sequence of the iap gene, responsible for alkaline phosphatase isozyme conversion in *Escherichia coli*, and identification of the gene product. Journal of bacteriology, 169(12), 5429-33.

Jackson, A. L., Bartz, S. R., Schelter, J., Kobayashi, S. V, Burchard, J., Mao, M., . . . Linsley, P. S. (2003). Expression profiling reveals off-target gene regulation by RNAi. Nature biotechnology, 21(6), 635-7. doi:10.1038/nbt831

Jackson, A. L., Burchard, J., Leake, D., Reynolds, A., Schelter, J., Guo, J., . . . Linsley, P. S. (2006). Position-specific chemical modification of siRNAs reduces "off-target" transcript silencing. RNA (New York, N.Y.), 12(7), 1197-205. doi:10.1261/rna.30706

Jansen, R., Embden, J. D. A. van, Gaastra, W., & Schouls, L. M. (2002). Identification of genes that are associated with DNA repeats in prokaryotes. Molecular microbiology, 43(6), 1565-75.

Konermann, S., Brigham, M. D., Trevino, A. E., Hsu, P. D., Heidenreich, M., Cong, L., . . . Zhang, F. (2013). Optical control of mammalian endogenous transcription and epigenetic states. Nature, 500(7463), 472-6. doi:10.1038/nature12466

Mackay, J. P., Font, J., & Segal, D. J. (2011). The prospects for designer single-stranded RNA-binding proteins. Nature structural & molecular biology, 18(3), 256-61. doi:10.1038/nsmb.2005

Makarova, K. S., Haft, D. H., Barrangou, R., Brouns, S. J. J., Charpentier, E., Horvath, P., . . . Koonin, E. V. (2011). Evolution and classification of the CRISPR-Cas systems. Nature reviews. Microbiology, 9(6), 467-77. doi:10.1038/nrmicro2577

Mali, P., Yang, L., Esvelt, K. M., Aach, J., Guell, M., DiCarlo, J. E., . . . Church, G. M. (2013). RNA-guided human genome engineering via Cas9. Science (New York, N.Y.), 339(6121), 823-6. doi:10.1126/science.1232033

Marraffini, L. A., & Sontheimer, E. J. (2010). CRISPR interference: RNA-directed adaptive immunity in bacteria and archaea. Nature reviews. Genetics, 11(3), 181-90. doi:10.1038/nrg2749

Mojica, F. J., Diez-Villasdior, C., Soria, E., & Juez, G. (2000). Biological significance of a family of regularly spaced repeats in the genomes of Archaea, Bacteria and mitochondria. Molecular microbiology, 36(1), 244-6.

Mojica, F. J. M., Diez-Villasefior, C., Garcia-Martinez, J., & Soria, E. (2005). Intervening sequences of regularly spaced prokaryotic repeats derive from foreign genetic elements. Journal of molecular evolution, 60(2), 174-82. doi:10.1007/s00239-004-0046-3

Peabody, D. S. (1993). The RNA binding site of bacteriophage MS2 coat protein. The EMBO journal, 12(2), 595-600.

Qi, L. S., Larson, M. H., Gilbert, L. A., Doudna, J. A., Weissman, J. S., Arkin, A. P., & Lim, W. A. (2013). Repurposing CRISPR as an RNA-guided platform for sequence-specific control of gene expression. Cell, 152(5), 1173-83. doi:10.1016/j.cell.2013.02.022

Sapranauskas, R., Gasiunas, G., Fremaux, C., Barrangou, R., Horvath, P., & Siksnys, V. (2011). The *Streptococcus thermophilus* CRISPR/Cas system provides immunity in *Escherichia coli*. Nucleic acids research, 39(21), 9275-82. doi:10.1093/nar/gkr606

SenGupta, D. J., Zhang, B., Kraemer, B., Pochart, P., Fields, S., & Wickens, M. (1996). A three-hybrid system to detect RNA-protein interactions in vivo. Proceedings of the National Academy of Sciences, 93(16), 8496-8501. doi:10.1073/pnas.93.16.8496

Valencia-Burton, M., McCullough, R. M., Cantor, C. R., & Broude, N. E. (2007). RNA visualization in live bacterial cells using fluorescent protein complementation. Nature methods, 4(5), 421-7. doi:10.1038/nmeth1023

Wang, X., McLachlan, J., Zamore, P. D., & Hall, T. M. T. (2002). Modular Recognition of RNA by a Human *Pumilio*-Homology Domain. Cell, 110(4), 501-512.

Zhang, J., Rouillon, C., Kerou, M., Reeks, J., Brugger, K., Graham, S., . . . White, M. F. (2012). Structure and mechanism of the CMR complex for CRISPR-mediated antiviral immunity. Molecular cell, 45(3), 303-13. doi:10.1016/j.molcel.2011.12.013

What is claimed is:

1. A method of altering expression of at least one gene product comprising introducing into a eukaryotic cell containing a DNA molecule having a target sequence adjacent to a Protospacer Adjacent Motif (PAM) and encoding the gene product an engineered, non-naturally occurring Clustered Regularly Interspaced Short Palindromic Repeats (CRISPR)-CRISPR associated (Cas) system comprising one or more vectors comprising:
   a) a first regulatory element operable in a eukaryotic cell operably linked to at least one nucleotide sequence encoding a CRISPR-Cas system guide RNA that hybridizes with the target sequence, and
   b) a second regulatory element operable in a eukaryotic cell operably linked to a nucleotide sequence encoding a fusion of a Type-II Cas9 protein and one or more protein domains, wherein:
   components (a) and (b) are located on same or different vectors of the system, the Cas9 protein comprises one or more mutations in a catalytic domain,
   the guide RNA comprises a tracr sequence which is 30 or more nucleotides in length,
   whereby expression of the at least one gene product is altered; and, wherein the Cas9 protein and the guide RNA do not naturally occur together.

2. The method of claim 1, wherein the CRISPR-Cas system further comprises a flexible linker between the Cas9 protein and the one or more protein domains.

3. The method of claim 1, wherein the one or more protein domains comprises one or more nuclear localization signal(s) (NLS(s)).

4. The method of claim 1, wherein the CRISPR-Cas system comprises a trans-activating cr (tracr) sequence.

5. The method of claim 1, wherein the guide RNA comprises a guide sequence and a tracr sequence.

6. The method of claim 1, wherein the Cas9 protein is codon optimized for expression in the eukaryotic cell and/or the eukaryotic cell is a mammalian and/or human cell.

7. The method of claim 1, wherein the one or more protein domains comprises one or more activator(s).

8. The method of claim 1, wherein the expression of one or more gene products is increased.

9. The method of claim 1, wherein the expression of one or more gene products is decreased.

10. The method of claim 1, wherein the one or more vectors are viral vectors.

11. The method of claim 1, wherein the viral vectors are selected from the group consisting of retroviral, lentiviral, adenoviral, adeno-associated and herpes simplex viral vectors.

12. A CRISPR-Cas system-mediated genome targeting method comprising introducing into a eukaryotic cell containing a DNA molecule having a target sequence adjacent to a Protospacer Adjacent Motif (PAM) and encoding at least one gene product an engineered, non-naturally occurring CRISPR-Cas system comprising one or more vectors comprising:
   a) a first regulatory element operable in a eukaryotic cell operably linked to at least one nucleotide sequence encoding a CRISPR-Cas system guide RNA that hybridizes with the target sequence, and
   b) a second regulatory element operable in a eukaryotic cell operably linked to a nucleotide sequence encoding a fusion of a Type-II Cas9 protein and one or more protein domains,
   wherein components (a) and (b) are located on same or different vectors of the system, wherein the Cas9 protein comprises one or more mutations in a catalytic domain,
   wherein the guide RNA comprises a tracr sequence which is 30 or more nucleotides in length,
   whereby expression of the at least one gene product is altered through the CRISP R-Cas system acting as to the DNA molecule comprising the guide RNA directing sequence-specific binding of the CRISPR-Cas system and PAM recognition, whereby there is genome targeting; and, wherein the Cas9 protein and the guide RNA do not naturally occur together.

13. The method of claim 12, wherein the CRISPR-Cas system further comprises a flexible linker between the Cas9 protein and the one or more protein domains.

14. The method of claim 12, wherein the one or more protein domains comprises one or more NLS(s).

15. The method of claim 12, wherein the CRISPR-Cas system comprises a tracr sequence.

16. The method of claim 12, wherein the Cas9 protein is codon optimized for expression in the eukaryotic cell and/or the eukaryotic cell is a mammalian or human cell.

17. The method of claim 12, wherein the one or more protein domains comprises one or more activator(s).

18. The method of claim 12, wherein the expression of one or more gene products is increased.

19. The method of claim 12, wherein the expression of one or more gene products is decreased.

20. The method of claim 12, wherein the one or more vectors are viral vectors.

21. The method of claim 12, wherein the viral vectors are selected from the group consisting of retroviral, lentiviral, adenoviral, adeno-associated and herpes simplex viral vectors.

22. An engineered, programmable, non-naturally occurring Type II CRISPR-Cas system comprising a fusion of a Cas9 protein and one or more protein domains, and at least one guide RNA that targets and hybridizes to a target sequence of a DNA molecule adjacent to a Protospacer Adjacent Motif (PAM) in a eukaryotic cell, wherein the DNA molecule encodes at least one gene product, wherein the CRISPR-Cas system comprises a tracr sequence, wherein the Cas9 protein comprises one or more mutations in a catalytic domain, wherein the guide RNA comprises a tracr sequence which is 30 or more nucleotides in length, whereby when the CRISPR-Cas system is introduced into the eukaryotic cell expression of the at least one gene product is altered through the CRISPR-Cas system acting as to the DNA molecule comprising the guide RNA directing sequence-specific binding of the CRISPR-Cas system and PAM recognition; and, wherein the Cas9 protein and the guide RNA do not naturally occur together.

23. The CRISPR-Cas system of claim 22, wherein the CRISP R-Cas system further comprises a flexible linker between the Cas9 protein and the one or more protein domains.

24. The CRISPR-Cas system of claim 22, wherein the one or more protein domains comprises one or more NLS(s): or activator(s); or repressor(s).

25. The CRISPR-Cas system of claim 22, wherein the Cas9 protein is codon optimized for expression in the eukaryotic cell and/or the eukaryotic cell is a mammalian or human cell.

26. The CRISPR-Cas system of claim 22, wherein the one or more protein domains comprises one or more activator(s).

27. The CRISPR-Cas system of claim 22, wherein the expression of one or more gene products is increased.

28. The CRISP R-Cas system of claim 22, wherein the expression of one or more gene products is decreased.

* * * * *

SEQUENCE LISTING

<160> NUMBER OF SEQ ID NOS: 104

<210> SEQ ID NO 1
<211> LENGTH: 6
<212> TYPE: PRT

-continued

```
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
guuuuagagc ua                                                            12

<210> SEQ ID NO 3
<211> LENGTH: 7
<212> TYPE: PRT
<213> ORGANISM: Simian virus 40

<400> SEQUENCE: 3

Pro Lys Lys Lys Arg Lys Val
1               5

<210> SEQ ID NO 4
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 4

Lys Arg Pro Ala Ala Thr Lys Lys Ala Gly Gln Ala Lys Lys Lys Lys
1               5                   10                  15

<210> SEQ ID NO 5
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 5

Pro Ala Ala Lys Arg Val Lys Leu Asp
1               5

<210> SEQ ID NO 6
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 6

Arg Gln Arg Arg Asn Glu Leu Lys Arg Ser Pro
1               5                   10

<210> SEQ ID NO 7
<211> LENGTH: 38
```

```
<212> TYPE: PRT
<213> ORGANISM: Homo sapiens

<400> SEQUENCE: 7

Asn Gln Ser Ser Asn Phe Gly Pro Met Lys Gly Gly Asn Phe Gly Gly
1               5                   10                  15
Arg Ser Ser Gly Pro Tyr Gly Gly Gly Gln Tyr Phe Ala Lys Pro
            20                  25                  30
Arg Asn Gln Gly Gly Tyr
        35

<210> SEQ ID NO 8
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 8

Arg Met Arg Ile Glx Phe Lys Asn Lys Gly Lys Asp Thr Ala Glu Leu
1               5                   10                  15
Arg Arg Arg Arg Val Glu Val Ser Val Glu Leu Arg Lys Ala Lys Lys
            20                  25                  30
Asp Glu Gln Ile Leu Lys Arg Arg Asn Val
        35                  40

<210> SEQ ID NO 9
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 9

Val Ser Arg Lys Arg Pro Arg Pro
1               5

<210> SEQ ID NO 10
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 10

Pro Pro Lys Lys Ala Arg Glu Asp
1               5

<210> SEQ ID NO 11
<211> LENGTH: 8
<212> TYPE: PRT
<213> ORGANISM: Homo sapiens

<400> SEQUENCE: 11

Pro Gln Pro Lys Lys Lys Pro Leu
1               5

<210> SEQ ID NO 12
<211> LENGTH: 12
<212> TYPE: PRT
<213> ORGANISM: Mus musculus
```

```
<400> SEQUENCE: 12

Ser Ala Leu Ile Lys Lys Lys Lys Met Ala Pro
1               5                   10

<210> SEQ ID NO 13
<211> LENGTH: 5
<212> TYPE: PRT
<213> ORGANISM: Influenza virus

<400> SEQUENCE: 13

Asp Arg Leu Arg Arg
1               5

<210> SEQ ID NO 14
<211> LENGTH: 7
<212> TYPE: PRT
<213> ORGANISM: Influenza virus

<400> SEQUENCE: 14

Pro Lys Gln Lys Lys Arg Lys
1               5

<210> SEQ ID NO 15
<211> LENGTH: 10
<212> TYPE: PRT
<213> ORGANISM: Hepatitus delta virus

<400> SEQUENCE: 15

Arg Lys Leu Lys Lys Lys Ile Lys Lys Leu
1               5                   10

<210> SEQ ID NO 16
<211> LENGTH: 10
<212> TYPE: PRT
<213> ORGANISM: Mus musculus

<400> SEQUENCE: 16

Arg Glu Lys Lys Lys Phe Leu Lys Arg Arg
1               5                   10

<210> SEQ ID NO 17
<211> LENGTH: 20
<212> TYPE: PRT
<213> ORGANISM: Homo sapiens

<400> SEQUENCE: 17

Lys Arg Lys Gly Asp Glu Val Asp Gly Val Asp Glu Val Ala Lys Lys
1               5                   10                  15

Lys Ser Lys Lys
            20

<210> SEQ ID NO 18
<211> LENGTH: 17
<212> TYPE: PRT
<213> ORGANISM: Homo sapiens

<400> SEQUENCE: 18

Arg Lys Cys Leu Gln Ala Gly Met Asn Leu Glu Ala Arg Lys Thr Lys
1               5                   10                  15

Lys

<210> SEQ ID NO 19
<211> LENGTH: 27
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 19
nnnnnnnnnn nnnnnnnnnn nnagaaw                                           27

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 20
nnnnnnnnnn nnnnagaaw                                                    19

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 21
nnnnnnnnnn nnnnnnnnnn nnagaaw                                           27

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 22
```
nnnnnnnnnn nnnagaaw                                                    18

<210> SEQ ID NO 23
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 23
nnnnnnnnnn nnnnnnnnnn gttttgtac tctcaagatt tagaaataaa tcttgcagaa        60
gctacaaaga taaggcttca tgccgaaatc aacaccctgt cattttatgg cagggtgttt      120
tcgttattta attttt                                                     137

<210> SEQ ID NO 24
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 24
nnnnnnnnnn nnnnnnnnnn gttttgtac tctcagaaat gcagaagcta caaagataag        60
gcttcatgcc gaaatcaaca ccctgtcatt ttatggcagg gtgttttcgt tatttaattt      120
ttt                                                                   123

<210> SEQ ID NO 25
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 25
nnnnnnnnnn nnnnnnnnnn gttttgtac tctcagaaat gcagaagcta caaagataag        60
gcttcatgcc gaaatcaaca ccctgtcatt ttatggcagg gtgttttttt                 110

<210> SEQ ID NO 26
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 26
nnnnnnnnnn nnnnnnnnnn gtttagagc tagaaatagc aagttaaaat aaggctagtc        60

```
cgttatcaac ttgaaaaagt ggcaccgagt cggtgctttt tt                     102
```

<210> SEQ ID NO 27
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 27

```
nnnnnnnnnn nnnnnnnnnn gttttagagc tagaaatagc aagttaaaat aaggctagtc   60
cgttatcaac ttgaaaaagt gttttttt                                     88
```

<210> SEQ ID NO 28
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 28

```
nnnnnnnnnn nnnnnnnnnn gttttagagc tagaaatagc aagttaaaat aaggctagtc   60
cgttatcatt tttttt                                                  76
```

<210> SEQ ID NO 29
<211> LENGTH: 984
<212> TYPE: PRT
<213> ORGANISM: Campylobacter jejuni

<400> SEQUENCE: 29

```
Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Lys Glu Lys Gly Ala
    130                 135                 140

Ile Leu Lys Ala Ile Lys Gln Asn Glu Glu Lys Leu Ala Asn Tyr Gln
145                 150                 155                 160
```

Ser Val Gly Glu Tyr Leu Tyr Lys Glu Tyr Phe Gln Lys Phe Lys Glu
            165                 170                 175

Asn Ser Lys Glu Phe Thr Asn Val Arg Asn Lys Lys Glu Ser Tyr Glu
        180                 185                 190

Arg Cys Ile Ala Gln Ser Phe Leu Lys Asp Glu Leu Lys Leu Ile Phe
    195                 200                 205

Lys Lys Gln Arg Glu Phe Gly Phe Ser Phe Ser Lys Lys Phe Glu Glu
210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
    370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
        515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu

-continued

```
                580             585             590
Ala Phe Gly Asn Asp Ser Ala Lys Trp Gln Lys Ile Glu Val Leu Ala
            595             600             605
Lys Asn Leu Pro Thr Lys Lys Gln Lys Arg Ile Leu Asp Lys Asn Tyr
610             615             620
Lys Asp Lys Glu Gln Lys Asn Phe Lys Asp Arg Asn Leu Asn Asp Thr
625             630             635             640
Arg Tyr Ile Ala Arg Leu Val Leu Asn Tyr Thr Lys Asp Tyr Leu Asp
            645             650             655
Phe Leu Pro Leu Ser Asp Asp Glu Asn Thr Lys Leu Asn Asp Thr Gln
            660             665             670
Lys Gly Ser Lys Val His Val Glu Ala Lys Ser Gly Met Leu Thr Ser
            675             680             685
Ala Leu Arg His Thr Trp Gly Phe Ser Ala Lys Asp Arg Asn Asn His
            690             695             700
Leu His His Ala Ile Asp Ala Val Ile Ile Ala Tyr Ala Asn Asn Ser
705             710             715             720
Ile Val Lys Ala Phe Ser Asp Phe Lys Lys Glu Gln Glu Ser Asn Ser
            725             730             735
Ala Glu Leu Tyr Ala Lys Lys Ile Ser Glu Leu Asp Tyr Lys Asn Lys
            740             745             750
Arg Lys Phe Phe Glu Pro Phe Ser Gly Phe Arg Gln Lys Val Leu Asp
            755             760             765
Lys Ile Asp Glu Ile Phe Val Ser Lys Pro Glu Arg Lys Lys Pro Ser
770             775             780
Gly Ala Leu His Glu Glu Thr Phe Arg Lys Glu Glu Phe Tyr Gln
785             790             795             800
Ser Tyr Gly Gly Lys Glu Gly Val Leu Lys Ala Leu Glu Leu Gly Lys
            805             810             815
Ile Arg Lys Val Asn Gly Lys Ile Val Lys Asn Gly Asp Met Phe Arg
            820             825             830
Val Asp Ile Phe Lys His Lys Lys Thr Asn Lys Phe Tyr Ala Val Pro
            835             840             845
Ile Tyr Thr Met Asp Phe Ala Leu Lys Val Leu Pro Asn Lys Ala Val
850             855             860
Ala Arg Ser Lys Lys Gly Glu Ile Lys Asp Trp Ile Leu Met Asp Glu
865             870             875             880
Asn Tyr Glu Phe Cys Phe Ser Leu Tyr Lys Asp Ser Leu Ile Leu Ile
            885             890             895
Gln Thr Lys Asp Met Gln Glu Pro Glu Phe Val Tyr Tyr Asn Ala Phe
            900             905             910
Thr Ser Ser Thr Val Ser Leu Ile Val Ser Lys His Asp Asn Lys Phe
            915             920             925
Glu Thr Leu Ser Lys Asn Gln Lys Ile Leu Phe Lys Asn Ala Asn Glu
            930             935             940
Lys Glu Val Ile Ala Lys Ser Ile Gly Ile Gln Asn Leu Lys Val Phe
945             950             955             960
Glu Lys Tyr Ile Val Ser Ala Leu Gly Glu Val Thr Lys Ala Glu Phe
            965             970             975
Arg Gln Arg Glu Asp Phe Lys Lys
            980
```

<210> SEQ ID NO 30

```
<211> LENGTH: 91
<212> TYPE: DNA
<213> ORGANISM: Homo sapiens

<400> SEQUENCE: 30
tataatctca aagaaatttt aaaaagggac taaaataaag agtttgcggg actctgcggg      60
gttacaatcc cctaaaaccg cttttaaaat t                                    91

<210> SEQ ID NO 31
<211> LENGTH: 36
<212> TYPE: DNA
<213> ORGANISM: Homo sapiens

<400> SEQUENCE: 31
attttaccat aaagaaattt aaaaagggac taaaac                               36

<210> SEQ ID NO 32
<211> LENGTH: 95
<212> TYPE: RNA
<213> ORGANISM: Homo sapiens
<220> FEATURE:
<221> NAME/KEY: modified_base
<222> LOCATION: (1)..(20)
<223> OTHER INFORMATION: a, c, u, g, unknown or other

<400> SEQUENCE: 32
nnnnnnnnnn nnnnnnnnnn guuuuagucc cgaaagggac uaaaauaaag aguuugcggg      60
acucugcggg guuacaaucc ccuaaaaccg cuuuu                                95

<210> SEQ ID NO 33
<211> LENGTH: 1115
<212> TYPE: PRT
<213> ORGANISM: Homo sapiens

<400> SEQUENCE: 33

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190
```

Ala Leu Arg Ile Leu Gln Thr Gln Gln Glu Phe Asn Pro Gln Ile Thr
    195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Asn Gln Thr Thr Gln Lys Gly Gln Lys Asn Ser Arg Glu Arg Met
        515                 520                 525

Lys Arg Ile Glu Glu Gly Ile Lys Glu Leu Gly Ser Gln Ile Leu Lys
    530                 535                 540

Glu His Pro Val Glu Asn Thr Gln Leu Gln Asn Glu Lys Leu Tyr Leu
545                 550                 555                 560

Tyr Tyr Leu Gln Asn Gly Arg Asp Met Tyr Val Asp Gln Glu Leu Asp
                565                 570                 575

Ile Asn Arg Leu Ser Asp Tyr Asp Val Asp His Ile Val Pro Gln Ser
            580                 585                 590

Phe Leu Lys Asp Asp Ser Ile Asp Asn Lys Val Leu Thr Arg Ser Asp
        595                 600                 605

-continued

Lys Asn Arg Gly Lys Ser Asp Asn Val Pro Ser Glu Glu Val Val Lys
610                 615                 620

Lys Met Lys Asn Tyr Trp Arg Gln Leu Leu Asn Ala Lys Leu Ile Thr
625                 630                 635                 640

Gln Arg Lys Phe Asp Asn Leu Thr Lys Ala Glu Arg Gly Gly Leu Ser
        645                 650                 655

Glu Leu Asp Lys Ala Gly Phe Ile Lys Arg Gln Leu Val Glu Thr Arg
        660                 665                 670

Gln Ile Thr Lys His Val Ala Gln Ile Leu Asp Ser Arg Met Asn Thr
        675                 680                 685

Lys Tyr Asp Glu Asn Asp Lys Leu Ile Arg Glu Val Lys Val Ile Thr
690                 695                 700

Leu Lys Ser Lys Leu Val Ser Asp Phe Arg Lys Asp Phe Gln Phe Tyr
705                 710                 715                 720

Lys Val Arg Glu Ile Asn Asn Tyr His His Ala His Asp Ala Tyr Leu
                725                 730                 735

Asn Ala Val Val Gly Thr Ala Leu Ile Lys Lys Tyr Pro Lys Leu Glu
            740                 745                 750

Ser Glu Phe Val Tyr Gly Asp Tyr Lys Val Tyr Asp Val Arg Lys Met
        755                 760                 765

Ile Ala Lys Ser Glu Gln Glu Ile Gly Lys Ala Thr Ala Lys Tyr Phe
770                 775                 780

Phe Tyr Ser Asn Ile Met Asn Phe Phe Lys Thr Glu Ile Thr Leu Ala
785                 790                 795                 800

Asn Gly Glu Ile Arg Lys Arg Pro Leu Ile Glu Thr Asn Gly Glu Thr
                805                 810                 815

Gly Glu Ile Val Trp Asp Lys Gly Arg Asp Phe Ala Thr Val Arg Lys
            820                 825                 830

Val Leu Ser Met Pro Gln Val Asn Ile Val Lys Lys Thr Glu Val Gln
        835                 840                 845

Thr Gly Gly Phe Ser Lys Glu Ser Ile Leu Pro Lys Arg Asn Ser Asp
        850                 855                 860

Lys Leu Ile Ala Arg Lys Lys Asp Trp Asp Pro Lys Lys Tyr Gly Gly
865                 870                 875                 880

Phe Asp Ser Pro Thr Val Ala Tyr Ser Val Leu Val Val Ala Lys Val
                885                 890                 895

Glu Lys Gly Lys Ser Lys Lys Leu Lys Ser Val Lys Glu Leu Leu Gly
            900                 905                 910

Ile Thr Ile Met Glu Arg Ser Ser Phe Glu Lys Asn Pro Ile Asp Phe
        915                 920                 925

Leu Glu Ala Lys Gly Tyr Lys Glu Val Lys Lys Asp Leu Ile Ile Lys
        930                 935                 940

Leu Pro Lys Tyr Ser Leu Phe Glu Leu Glu Asn Gly Arg Lys Arg Met
945                 950                 955                 960

Leu Ala Ser Ala Gly Glu Leu Gln Lys Gly Asn Glu Leu Ala Leu Pro
                965                 970                 975

Ser Lys Tyr Val Asn Phe Leu Tyr Leu Ala Ser His Tyr Glu Lys Leu
            980                 985                 990

Lys Gly Ser Pro Glu Asp Asn Glu   Gln Lys Gln Leu Phe Val Glu Gln
        995                 1000                1005

His Lys  His Tyr Leu Asp Glu  Ile Ile Glu Gln Ile  Ser Glu Phe
    1010                1015                1020

Ser Lys  Arg Val Ile Leu Ala  Asp Ala Asn Leu Asp  Lys Val Leu

```
                1025                1030                1035

Ser Ala Tyr Asn Lys His Arg Asp Lys Pro Ile Arg Glu Gln Ala
        1040                1045                1050

Glu Asn Ile Ile His Leu Phe Thr Leu Thr Asn Leu Gly Ala Pro
1055                1060                1065

Ala Ala Phe Lys Tyr Phe Asp Thr Thr Ile Asp Arg Lys Arg Tyr
        1070                1075                1080

Thr Ser Thr Lys Glu Val Leu Asp Ala Thr Leu Ile His Gln Ser
        1085                1090                1095

Ile Thr Gly Leu Tyr Glu Thr Arg Ile Asp Leu Ser Gln Leu Gly
        1100                1105                1110

Gly Asp
    1115

<210> SEQ ID NO 34
<211> LENGTH: 1374
<212> TYPE: PRT
<213> ORGANISM: Homo sapiens

<400> SEQUENCE: 34

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270
```

```
Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
```

-continued

```
            690                 695                 700
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Thr Asn
                755                 760                 765

Glu Asp Asp Glu Lys Lys Ala Ile Gln Lys Ile Gln Lys Ala Asn Lys
770                 775                 780

Asp Glu Lys Asp Ala Ala Met Leu Lys Ala Ala Asn Gln Tyr Asn Gly
785                 790                 795                 800

Lys Ala Glu Leu Pro His Ser Val Phe His Gly His Lys Gln Leu Ala
                805                 810                 815

Thr Lys Ile Arg Leu Trp His Gln Gln Gly Glu Arg Cys Leu Tyr Thr
                820                 825                 830

Gly Lys Thr Ile Ser Ile His Asp Leu Ile Asn Asn Ser Asn Gln Phe
                835                 840                 845

Glu Val Asp His Ile Leu Pro Leu Ser Ile Thr Phe Asp Asp Ser Leu
850                 855                 860

Ala Asn Lys Val Leu Val Tyr Ala Thr Ala Asn Gln Glu Lys Gly Gln
865                 870                 875                 880

Arg Thr Pro Tyr Gln Ala Leu Asp Ser Met Asp Asp Ala Trp Ser Phe
                885                 890                 895

Arg Glu Leu Lys Ala Phe Val Arg Glu Ser Lys Thr Leu Ser Asn Lys
                900                 905                 910

Lys Lys Glu Tyr Leu Leu Thr Glu Glu Asp Ile Ser Lys Phe Asp Val
                915                 920                 925

Arg Lys Lys Phe Ile Glu Arg Asn Leu Val Asp Thr Arg Tyr Ala Ser
930                 935                 940

Arg Val Val Leu Asn Ala Leu Gln Glu His Phe Arg Ala His Lys Ile
945                 950                 955                 960

Asp Thr Lys Val Ser Val Val Arg Gly Gln Phe Thr Ser Gln Leu Arg
                965                 970                 975

Arg His Trp Gly Ile Glu Lys Thr Arg Asp Thr Tyr His His Ala
                980                 985                 990

Val Asp Ala Leu Ile Ile Ala Ala  Ser Ser Gln Leu Asn  Leu Trp Lys
                995                 1000                1005

Lys Gln  Lys Asn Thr Leu Val  Ser Tyr Ser Glu Asp  Gln Leu Leu
1010                 1015                 1020

Asp Ile  Glu Thr Gly Glu Leu  Ile Ser Asp Asp Glu  Tyr Lys Glu
1025                 1030                 1035

Ser Val  Phe Lys Ala Pro Tyr  Gln His Phe Val Asp  Thr Leu Lys
1040                 1045                 1050

Ser Lys  Glu Phe Glu Asp Ser  Ile Leu Phe Ser Tyr  Gln Val Asp
1055                 1060                 1065

Ser Lys  Phe Asn Arg Lys Ile  Ser Asp Ala Thr Ile  Tyr Ala Thr
1070                 1075                 1080

Arg Gln  Ala Lys Val Gly Lys  Asp Lys Ala Asp Glu  Thr Tyr Val
1085                 1090                 1095

Leu Gly  Lys Ile Lys Asp Ile  Tyr Thr Gln Asp Gly  Tyr Asp Ala
1100                 1105                 1110
```

Phe Met Lys Ile Tyr Lys Lys Asp Lys Ser Lys Phe Leu Met Tyr
1115                1120                1125

Arg His Asp Pro Gln Thr Phe Glu Lys Val Ile Glu Pro Ile Leu
1130                1135                1140

Glu Asn Tyr Pro Asn Lys Gln Ile Asn Glu Lys Gly Lys Glu Val
1145                1150                1155

Pro Cys Asn Pro Phe Leu Lys Tyr Lys Glu Glu His Gly Tyr Ile
1160                1165                1170

Arg Lys Tyr Ser Lys Lys Gly Asn Gly Pro Glu Ile Lys Ser Leu
1175                1180                1185

Lys Tyr Tyr Asp Ser Lys Leu Gly Asn His Ile Asp Ile Thr Pro
1190                1195                1200

Lys Asp Ser Asn Asn Lys Val Val Leu Gln Ser Val Ser Pro Trp
1205                1210                1215

Arg Ala Asp Val Tyr Phe Asn Lys Thr Thr Gly Lys Tyr Glu Ile
1220                1225                1230

Leu Gly Leu Lys Tyr Ala Asp Leu Gln Phe Glu Lys Gly Thr Gly
1235                1240                1245

Thr Tyr Lys Ile Ser Gln Glu Lys Tyr Asn Asp Ile Lys Lys Lys
1250                1255                1260

Glu Gly Val Asp Ser Asp Ser Glu Phe Lys Phe Thr Leu Tyr Lys
1265                1270                1275

Asn Asp Leu Leu Leu Val Lys Asp Thr Glu Thr Lys Glu Gln Gln
1280                1285                1290

Leu Phe Arg Phe Leu Ser Arg Thr Met Pro Lys Gln Lys His Tyr
1295                1300                1305

Val Glu Leu Lys Pro Tyr Asp Lys Gln Lys Phe Glu Gly Gly Glu
1310                1315                1320

Ala Leu Ile Lys Val Leu Gly Asn Val Ala Asn Ser Gly Gln Cys
1325                1330                1335

Lys Lys Gly Leu Gly Lys Ser Asn Ile Ser Ile Tyr Lys Val Arg
1340                1345                1350

Thr Asp Val Leu Gly Asn Gln His Ile Ile Lys Asn Glu Gly Asp
1355                1360                1365

Lys Pro Lys Leu Asp Phe
    1370

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Glu Ala Ala Ala Lys Glu Ala Ala Ala Lys Glu Ala Ala Ala Lys
1               5                   10                  15
```

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Gly Gly Gly Gly Gly Ser Gly Gly Gly Gly Ser Gly Gly Gly Gly
1               5                   10                  15

Gly Ser
```

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tggttcagtg gctgcgtgtc                                             20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgttttcttg gtggtatata                                             20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atacgatgaa aagaataagc                                             20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gggggagagg gactaaagaa                                             20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
gggcggggga agggtaggtg                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
attagataaa gggggggacgg                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cggctttaac tggagtgcct                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtggctggca ggctggctct                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggcctccccc gcgcggccgg                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 gcccccttc atgcaaaacc                                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gacagccccc gtcacatgga                                        20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggcaggcgag gagggggagg                                        20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggcggggcct cccgcgccgc                                        20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gctgccgggt tttgcatgaa                                        20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggggctgtca gggaataaat                                        20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gagagaacga acgtgtctgc                                        20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 54
gagggtcact cggcggctcc                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcgcgctcca cacaactcac                                                    20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggggctgtgg ccggggcggt                                                    20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggcgaccgcg acagtggtgg                                                    20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gcaaaaatag acaatcagca                                                    20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gaaggatctc ggccaatttg                                                    20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
```
gtgggggccc agaaggtcct                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gccacggcct cccaatttac                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggaatatggt tcaacaggaa                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gctgcagagt aacccagact                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gccttggtga gactggtaga                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gattaactga gaattcacaa                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gtgtgcccgc caggaggggt                                               20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gttgcctgca taataacatg                                               20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggaggaaaaa atttaagagg                                               20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggaccgggat tgtccagcca                                               20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gagtgataag acacccgctt                                               20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gcagctggcc attgtgctta                                               20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggagaggggg tcaagcacct                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcgggttggg agttgaaagt                                                    20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gctccagcct cctaagtggc                                                    20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggaggtgggg ggagaaactg                                                    20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggtgaaatga gggcttgcga                                                    20

<210> SEQ ID NO 77
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gttttagagc tatgctgttt tgaatggtcc caaaacggaa gggcctgagt ccgagcagaa        60
gaagaagttt tagagctatg ctgttttgaa tggtcccaaa ac                          102

<210> SEQ ID NO 78
<211> LENGTH: 100
<212> TYPE: DNA
<213> ORGANISM: Homo sapiens

<400> SEQUENCE: 78
cggaggacaa agtacaaacg gcagaagctg gaggaggaag ggcctgagtc cgagcagaag        60
aagaagggct cccatcacat caaccggtgg cgcattgcca                             100

<210> SEQ ID NO 79
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agctggagga ggaagggcct gagtccgagc agaagaagaa gggctcccac          50

<210> SEQ ID NO 80
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gaguccgagc agaagaagaa guuuuagagc                                 30

<210> SEQ ID NO 81
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
agctggagga ggaagggcct gagtccgagc agaagagaag ggctcccat            49

<210> SEQ ID NO 82
<211> LENGTH: 53
<212> TYPE: DNA
<213> ORGANISM: Homo sapiens

<400> SEQUENCE: 82
ctggaggagg aagggcctga gtccgagcag aagaagaagg gctcccatca cat       53

<210> SEQ ID NO 83
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctggaggagg aagggcctga gtccgagcag aagagaaggg ctcccatcac at        52

<210> SEQ ID NO 84
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ctggaggagg aagggcctga gtccgagcag aagaaagaag gctcccatc acat       54

<210> SEQ ID NO 85
<211> LENGTH: 50

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctggaggagg aagggcctga gtccgagcag aagaagggct cccatcacat            50

<210> SEQ ID NO 86
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctggaggagg aagggcctga gcccgagcag aagggctccc atcacat               47

<210> SEQ ID NO 87
<211> LENGTH: 48
<212> TYPE: DNA
<213> ORGANISM: Unknown
<220> FEATURE:
<223> OTHER INFORMATION: Description of Unknown:
      Importin alpha NLS sequence

<400> SEQUENCE: 87
aaaaggccgg cggccacgaa aaaggccggc caggcaaaaa agaaaaag             48

<210> SEQ ID NO 88
<211> LENGTH: 215
<212> TYPE: DNA
<213> ORGANISM: Homo sapiens

<400> SEQUENCE: 88
gtggctggca ggctggctct gggagcctcc tcccctcct cgcctgcccc ctcctccccc   60
ggcctccccc gcgcggccgg cggcgcggga ggccccgccc cctttcatgc aaaacccggc  120
agcgaggctg ggctcgagtg gaggagccgc cgcgcgctga ttggtcgcta gaaacccatt  180
tattccctga cagcccccgt cacatggatg gttgt                            215

<210> SEQ ID NO 89
<211> LENGTH: 23
<212> TYPE: DNA
<213> ORGANISM: Homo sapiens

<400> SEQUENCE: 89 gcccccttc atgcaaaacc cgg                                          23

<210> SEQ ID NO 90
<211> LENGTH: 276
<212> TYPE: DNA
<213> ORGANISM: Homo sapiens

<400> SEQUENCE: 90
cgcccatggc cgcgcgcgct ccacacaact caccggagtc cgcgccttgc gccgccgacc   60
agttcgcagc tccgcgccac ggcagccagt ctctgagtgg aagagagcgc agcccggcca  120
ccggacctac ttactcgcct tgctgattgt ctattttgc gtttacaact tttctaagaa   180
cttttgtata caaaggaact ttttaaaaaa gacgcttcca agttatattt aatccaaaga  240
agaaggatct cggccaattt ggggttttgg gttttg                           276
```

<210> SEQ ID NO 91
<211> LENGTH: 151
<212> TYPE: DNA
<213> ORGANISM: Homo sapiens

<400> SEQUENCE: 91
tcccccgcgc ggccggcggc gcgggaggcc ccgccccctt tcatgcaaaa cccggcagcg      60
aggctgggct cgagtggagg agccgccgcg cgctgattgg tcgctagaaa cccatttatt     120
ccctgacagc ccccgtcaca tggatggttg t                                    151

<210> SEQ ID NO 92
<211> LENGTH: 30
<212> TYPE: DNA
<213> ORGANISM: Homo sapiens

<400> SEQUENCE: 92
gaagccgccg ggcccgcagc aaacttcggg                                       30

<210> SEQ ID NO 93
<211> LENGTH: 1453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn

-continued

```
               225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
```

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

Asn Gly Glu Ile Arg Lys Arg Pro Leu Ile Glu Thr Asn Gly Glu
            1055                1060                1065

```
Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

Ser Ala Gly Gly Gly Ser Gly Gly Gly Gly Ser Gly Gly Gly
    1370            1375            1380

Gly Ser Gly Pro Lys Lys Lys Arg Lys Val Ala Ala Ala Gly Ser
    1385            1390            1395

Gly Arg Ala Asp Ala Leu Asp Asp Phe Asp Leu Asp Met Leu Gly
    1400            1405            1410

Ser Asp Ala Leu Asp Asp Phe Asp Leu Asp Met Leu Gly Ser Asp
    1415            1420            1425

Ala Leu Asp Asp Phe Asp Leu Asp Met Leu Gly Ser Asp Ala Leu
    1430            1435            1440

Asp Asp Phe Asp Leu Asp Met Leu Ile Asn
    1445            1450
```

<210> SEQ ID NO 94
<211> LENGTH: 1569
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Met Gly Ser Gly Met Asn Ile Gln Met Leu Leu Glu Ala Ala Asp Tyr
1               5                   10                  15

Leu Glu Arg Arg Glu Arg Glu Ala Glu His Gly Tyr Ala Ser Met Leu
            20                  25                  30

Pro Gly Ser Gly Met Asn Ile Gln Met Leu Leu Glu Ala Ala Asp Tyr
        35                  40                  45

Leu Glu Arg Arg Glu Arg Glu Ala Glu His Gly Tyr Ala Ser Met Leu
    50                  55                  60

Pro Gly Ser Gly Met Asn Ile Gln Met Leu Leu Glu Ala Ala Asp Tyr
65                  70                  75                  80

Leu Glu Arg Arg Glu Arg Glu Ala Glu His Gly Tyr Ala Ser Met Leu
                85                  90                  95

Pro Gly Ser Gly Met Asn Ile Gln Met Leu Leu Glu Ala Ala Asp Tyr
            100                 105                 110

Leu Glu Arg Arg Glu Arg Glu Ala Glu His Gly Tyr Ala Ser Met Leu
        115                 120                 125

Pro Ser Arg Ser Ala Gly Pro Lys Lys Arg Lys Val Ala Ala Ala
    130                 135                 140

Asp Tyr Lys Asp Asp Asp Lys Ser Arg Leu Glu Pro Gly Glu Lys
145                 150                 155                 160

Pro Tyr Lys Cys Pro Glu Cys Gly Lys Ser Phe Ser Gln Ser Gly Ala
                165                 170                 175

Leu Thr Arg His Gln Arg Thr His Thr Arg Asp Lys Lys Tyr Ser Ile
            180                 185                 190

Gly Leu Ala Ile Gly Thr Asn Ser Val Gly Trp Ala Val Ile Thr Asp
        195                 200                 205

Glu Tyr Lys Val Pro Ser Lys Lys Phe Lys Val Leu Gly Asn Thr Asp
    210                 215                 220

Arg His Ser Ile Lys Lys Asn Leu Ile Gly Ala Leu Leu Phe Asp Ser
225                 230                 235                 240

Gly Glu Thr Ala Glu Ala Thr Arg Leu Lys Arg Thr Ala Arg Arg Arg
                245                 250                 255

Tyr Thr Arg Arg Lys Asn Arg Ile Cys Tyr Leu Gln Glu Ile Phe Ser
            260                 265                 270

Asn Glu Met Ala Lys Val Asp Asp Ser Phe Phe His Arg Leu Glu Glu
        275                 280                 285

Ser Phe Leu Val Glu Glu Asp Lys Lys His Glu Arg His Pro Ile Phe
    290                 295                 300

Gly Asn Ile Val Asp Glu Val Ala Tyr His Glu Lys Tyr Pro Thr Ile
305                 310                 315                 320

Tyr His Leu Arg Lys Lys Leu Val Asp Ser Thr Asp Lys Ala Asp Leu
                325                 330                 335

Arg Leu Ile Tyr Leu Ala Leu Ala His Met Ile Lys Phe Arg Gly His
            340                 345                 350

Phe Leu Ile Glu Gly Asp Leu Asn Pro Asp Asn Ser Asp Val Asp Lys
        355                 360                 365
```

```
Leu Phe Ile Gln Leu Val Gln Thr Tyr Asn Gln Leu Phe Glu Glu Asn
        370                 375                 380

Pro Ile Asn Ala Ser Gly Val Asp Ala Lys Ala Ile Leu Ser Ala Arg
385                 390                 395                 400

Leu Ser Lys Ser Arg Arg Leu Glu Asn Leu Ile Ala Gln Leu Pro Gly
                405                 410                 415

Glu Lys Lys Asn Gly Leu Phe Gly Asn Leu Ile Ala Leu Ser Leu Gly
            420                 425                 430

Leu Thr Pro Asn Phe Lys Ser Asn Phe Asp Leu Ala Glu Asp Ala Lys
                435                 440                 445

Leu Gln Leu Ser Lys Asp Thr Tyr Asp Asp Leu Asp Asn Leu Leu
450                 455                 460

Ala Gln Ile Gly Asp Gln Tyr Ala Asp Leu Phe Leu Ala Ala Lys Asn
465                 470                 475                 480

Leu Ser Asp Ala Ile Leu Leu Ser Asp Ile Leu Arg Val Asn Thr Glu
                485                 490                 495

Ile Thr Lys Ala Pro Leu Ser Ala Ser Met Ile Lys Arg Tyr Asp Glu
                500                 505                 510

His His Gln Asp Leu Thr Leu Leu Lys Ala Leu Val Arg Gln Gln Leu
            515                 520                 525

Pro Glu Lys Tyr Lys Glu Ile Phe Phe Asp Gln Ser Lys Asn Gly Tyr
        530                 535                 540

Ala Gly Tyr Ile Asp Gly Gly Ala Ser Gln Glu Glu Phe Tyr Lys Phe
545                 550                 555                 560

Ile Lys Pro Ile Leu Glu Lys Met Asp Gly Thr Glu Glu Leu Leu Val
                565                 570                 575

Lys Leu Asn Arg Glu Asp Leu Leu Arg Lys Gln Arg Thr Phe Asp Asn
            580                 585                 590

Gly Ser Ile Pro His Gln Ile His Leu Gly Glu Leu His Ala Ile Leu
        595                 600                 605

Arg Arg Gln Glu Asp Phe Tyr Pro Phe Leu Lys Asp Asn Arg Glu Lys
610                 615                 620

Ile Glu Lys Ile Leu Thr Phe Arg Ile Pro Tyr Tyr Val Gly Pro Leu
625                 630                 635                 640

Ala Arg Gly Asn Ser Arg Phe Ala Trp Met Thr Arg Lys Ser Glu Glu
                645                 650                 655

Thr Ile Thr Pro Trp Asn Phe Glu Glu Val Val Asp Lys Gly Ala Ser
            660                 665                 670

Ala Gln Ser Phe Ile Glu Arg Met Thr Asn Phe Asp Lys Asn Leu Pro
        675                 680                 685

Asn Glu Lys Val Leu Pro Lys His Ser Leu Leu Tyr Glu Tyr Phe Thr
690                 695                 700

Val Tyr Asn Glu Leu Thr Lys Val Lys Tyr Val Thr Glu Gly Met Arg
705                 710                 715                 720

Lys Pro Ala Phe Leu Ser Gly Glu Gln Lys Lys Ala Ile Val Asp Leu
                725                 730                 735

Leu Phe Lys Thr Asn Arg Lys Val Thr Val Lys Gln Leu Lys Glu Asp
            740                 745                 750

Tyr Phe Lys Lys Ile Glu Cys Phe Asp Ser Val Glu Ile Ser Gly Val
        755                 760                 765

Glu Asp Arg Phe Asn Ala Ser Leu Gly Thr Tyr His Asp Leu Leu Lys
770                 775                 780

Ile Ile Lys Asp Lys Asp Phe Leu Asp Asn Glu Glu Asn Glu Asp Ile
```

-continued

```
            785                 790                 795                 800
Leu Glu Asp Ile Val Leu Thr Leu Thr Leu Phe Glu Asp Arg Glu Met
                    805                 810                 815
Ile Glu Glu Arg Leu Lys Thr Tyr Ala His Leu Phe Asp Asp Lys Val
                    820                 825                 830
Met Lys Gln Leu Lys Arg Arg Tyr Thr Gly Trp Gly Arg Leu Ser
                835                 840                 845
Arg Lys Leu Ile Asn Gly Ile Arg Asp Lys Gln Ser Gly Lys Thr Ile
            850                 855                 860
Leu Asp Phe Leu Lys Ser Asp Gly Phe Ala Asn Arg Asn Phe Met Gln
865                 870                 875                 880
Leu Ile His Asp Asp Ser Leu Thr Phe Lys Glu Asp Ile Gln Lys Ala
                        885                 890                 895
Gln Val Ser Gly Gln Gly Asp Ser Leu His Glu His Ile Ala Asn Leu
                    900                 905                 910
Ala Gly Ser Pro Ala Ile Lys Lys Gly Ile Leu Gln Thr Val Lys Val
                915                 920                 925
Val Asp Glu Leu Val Lys Val Met Gly Arg His Lys Pro Glu Asn Ile
                930                 935                 940
Val Ile Glu Met Ala Arg Glu Asn Gln Thr Thr Gln Lys Gly Gln Lys
945                 950                 955                 960
Asn Ser Arg Glu Arg Met Lys Arg Ile Glu Glu Gly Ile Lys Glu Leu
                    965                 970                 975
Gly Ser Gln Ile Leu Lys Glu His Pro Val Glu Asn Thr Gln Leu Gln
                980                 985                 990
Asn Glu Lys Leu Tyr Leu Tyr Tyr  Leu Gln Asn Gly Arg  Asp Met Tyr
        995                 1000                1005
Val Asp  Gln Glu Leu Asp Ile  Asn Arg Leu Ser Asp  Tyr Asp Val
    1010                1015                1020
Asp Ala  Ile Val Pro Gln Ser  Phe Leu Lys Asp Asp  Ser Ile Asp
    1025                1030                1035
Asn Lys  Val Leu Thr Arg Ser  Asp Lys Asn Arg Gly  Lys Ser Asp
    1040                1045                1050
Asn Val  Pro Ser Glu Glu Val  Val Lys Lys Met Lys  Asn Tyr Trp
    1055                1060                1065
Arg Gln  Leu Leu Asn Ala Lys  Leu Ile Thr Gln Arg  Lys Phe Asp
    1070                1075                1080
Asn Leu  Thr Lys Ala Glu Arg  Gly Gly Leu Ser Glu  Leu Asp Lys
    1085                1090                1095
Ala Gly  Phe Ile Lys Arg Gln  Leu Val Glu Thr Arg  Gln Ile Thr
    1100                1105                1110
Lys His  Val Ala Gln Ile Leu  Asp Ser Arg Met Asn  Thr Lys Tyr
    1115                1120                1125
Asp Glu  Asn Asp Lys Leu Ile  Arg Glu Val Lys Val  Ile Thr Leu
    1130                1135                1140
Lys Ser  Lys Leu Val Ser Asp  Phe Arg Lys Asp Phe  Gln Phe Tyr
    1145                1150                1155
Lys Val  Arg Glu Ile Asn Asn  Tyr His His Ala His  Asp Ala Tyr
    1160                1165                1170
Leu Asn  Ala Val Val Gly Thr  Ala Leu Ile Lys Lys  Tyr Pro Lys
    1175                1180                1185
Leu Glu  Ser Glu Phe Val Tyr  Gly Asp Tyr Lys Val  Tyr Asp Val
    1190                1195                1200
```

```
Arg Lys Met Ile Ala Lys Ser Glu Gln Glu Ile Gly Lys Ala Thr
1205                1210                1215

Ala Lys Tyr Phe Phe Tyr Ser Asn Ile Met Asn Phe Phe Lys Thr
1220                1225                1230

Glu Ile Thr Leu Ala Asn Gly Glu Ile Arg Lys Arg Pro Leu Ile
1235                1240                1245

Glu Thr Asn Gly Glu Thr Gly Glu Ile Val Trp Asp Lys Gly Arg
1250                1255                1260

Asp Phe Ala Thr Val Arg Lys Val Leu Ser Met Pro Gln Val Asn
1265                1270                1275

Ile Val Lys Lys Thr Glu Val Gln Thr Gly Gly Phe Ser Lys Glu
1280                1285                1290

Ser Ile Leu Pro Lys Arg Asn Ser Asp Lys Leu Ile Ala Arg Lys
1295                1300                1305

Lys Asp Trp Asp Pro Lys Lys Tyr Gly Gly Phe Asp Ser Pro Thr
1310                1315                1320

Val Ala Tyr Ser Val Leu Val Ala Lys Val Glu Lys Gly Lys
1325                1330                1335

Ser Lys Lys Leu Lys Ser Val Lys Glu Leu Leu Gly Ile Thr Ile
1340                1345                1350

Met Glu Arg Ser Ser Phe Glu Lys Asn Pro Ile Asp Phe Leu Glu
1355                1360                1365

Ala Lys Gly Tyr Lys Glu Val Lys Lys Asp Leu Ile Ile Lys Leu
1370                1375                1380

Pro Lys Tyr Ser Leu Phe Glu Leu Glu Asn Gly Arg Lys Arg Met
1385                1390                1395

Leu Ala Ser Ala Gly Glu Leu Gln Lys Gly Asn Glu Leu Ala Leu
1400                1405                1410

Pro Ser Lys Tyr Val Asn Phe Leu Tyr Leu Ala Ser His Tyr Glu
1415                1420                1425

Lys Leu Lys Gly Ser Pro Glu Asp Asn Glu Gln Lys Gln Leu Phe
1430                1435                1440

Val Glu Gln His Lys His Tyr Leu Asp Glu Ile Ile Glu Gln Ile
1445                1450                1455

Ser Glu Phe Ser Lys Arg Val Ile Leu Ala Asp Ala Asn Leu Asp
1460                1465                1470

Lys Val Leu Ser Ala Tyr Asn Lys His Arg Asp Lys Pro Ile Arg
1475                1480                1485

Glu Gln Ala Glu Asn Ile Ile His Leu Phe Thr Leu Thr Asn Leu
1490                1495                1500

Gly Ala Pro Ala Ala Phe Lys Tyr Phe Asp Thr Thr Ile Asp Arg
1505                1510                1515

Lys Arg Tyr Thr Ser Thr Lys Glu Val Leu Asp Ala Thr Leu Ile
1520                1525                1530

His Gln Ser Ile Thr Gly Leu Tyr Glu Thr Arg Ile Asp Leu Ser
1535                1540                1545

Gln Leu Gly Gly Asp Lys Arg Pro Ala Ala Thr Lys Lys Ala Gly
1550                1555                1560

Gln Ala Lys Lys Lys Lys
1565

<210> SEQ ID NO 95
<211> LENGTH: 43
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (41)..(43)
<223> OTHER INFORMATION: a, c, u, g, unknown or other

<400> SEQUENCE: 95
nnncugaagu gcucucagcc gcaaggaccg cauacuacaa nnn              43

<210> SEQ ID NO 96
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
auugaaaguu guaguaugcg guccuugcgg cugagagcac uucag             45

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 97
nnnnnnnnnn nnnnnnnnnn ngg                                    23

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 98
nnnnnnnnnn nnngg                                             15

<210> SEQ ID NO 99
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 99
nnnnnnnnnn nnnnnnnnnn ngg                                            23

<210> SEQ ID NO 100
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 100
nnnnnnnnnn nngg                                                      14

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 101
nnnnnnnnnn nnnnnnnnnn nggng                                          25

<210> SEQ ID NO 102
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
```

```
<222> LOCATION: (16)..(16)
<223> OTHER INFORMATION: a, c, t, g, unknown or other

<400> SEQUENCE: 102
nnnnnnnnnn nnnggng                                                   17

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 103
nnnnnnnnnn nnnnnnnnnn nggng                                          25

<210> SEQ ID NO 104
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 104
nnnnnnnnnn nnggng                                                    16
```